US009809861B2

(12) United States Patent
Mitani et al.

(10) Patent No.: US 9,809,861 B2
(45) Date of Patent: Nov. 7, 2017

(54) METHOD OF EVALUATING INHIBITORY EFFECT ON DAMP-DRY MALODOR

(71) Applicant: Kao Corporation, Chuo-ku, Tokyo (JP)

(72) Inventors: Asako Mitani, Tokyo (JP); Hiromi Kubota, Tochigi (JP); Yu Niwano, Wakayama (JP); Kohei Takeuchi, Funabashi (JP); Atsushi Tanaka, Hannan (JP); Noriko Yamaguchi, Wakayama (JP)

(73) Assignee: Kao Corporation, Tokyo (JP)

( * ) Notice: Subject to any disclaimer, the term of this patent is extended or adjusted under 35 U.S.C. 154(b) by 426 days.

(21) Appl. No.: 14/375,998

(22) PCT Filed: May 28, 2013

(86) PCT No.: PCT/JP2013/065306
§ 371 (c)(1),
(2) Date: Jul. 31, 2014

(87) PCT Pub. No.: WO2013/180302
PCT Pub. Date: Dec. 5, 2013

(65) Prior Publication Data
US 2015/0031041 A1 Jan. 29, 2015

(30) Foreign Application Priority Data

May 29, 2012 (JP) ................. 2012-122032
May 23, 2013 (JP) ................. 2013-109303

(51) Int. Cl.
*C12P 19/34* (2006.01)
*C12Q 1/68* (2006.01)

(52) U.S. Cl.
CPC ........... *C12Q 1/6897* (2013.01); *C12Q 1/689* (2013.01); *C12Q 2600/136* (2013.01); *C12Q 2600/158* (2013.01)

(58) Field of Classification Search
USPC .............................. 435/6.12, 91.2
See application file for complete search history.

(56) References Cited

U.S. PATENT DOCUMENTS

| | | | |
|---|---|---|---|
| 6,673,910 B1 * | 1/2004 | Breton | C07K 14/212 435/320.1 |
| 8,771,660 B2 | 7/2014 | Mitani et al. | |
| 2013/0210061 A1 | 8/2013 | Mitani et al. | |

FOREIGN PATENT DOCUMENTS

| | | | |
|---|---|---|---|
| JP | 1981-124387 A | 9/1981 | |
| JP | 2004-262900 A | 9/2004 | |
| JP | 2004-263102 A | 9/2004 | |
| JP | 2009-507477 A | 2/2009 | |
| JP | 2009-244094 A | 10/2009 | |
| JP | 2011-075385 A | 4/2011 | |
| JP | 2011-177401 A | 9/2011 | |
| JP | 2011-254807 A | 12/2011 | |
| JP | 2012-088297 A | 5/2012 | |
| WO | WO 2007/031300 A1 | 3/2007 | |
| WO | WO 2012/039261 A1 | 3/2012 | |

OTHER PUBLICATIONS

Rychlik et al., Nucleic Acids Research 17(21), 8543-8551 (1989).*
International Search Report (ISR) for PCT/JP2013/065306; I.A. fd: May 28, 2013, dated Jul. 24, 2013 from the European Patent Office, Rijswijk, Netherlands.
Written Opinion of the International Searching Authority (PCT Rule 43bis.1) for PCT/JP2013/065306; I.A. fd: May 28, 2013, completed Jul. 24, 2013, by the European Patent Office, Munich Germany.
Database Geneseq [Online]: accession No. AFB15923, "SARS coronavirus related nucleic acid probe SEQ ID No. 198334," Oct. 4, 2007 (first entry) retrieved from EBI accession No. GSN:AFB15923, with Annex 1: European Patent Office IBIS alignment.
Database EMBL [Online]: accession No. EC565652, "1T257498_1542_3796 LNCAP + R1881 synthetic Androgen human prostate library *Homo sapiens* cDNA similar to ENSG00000166451-ENST00000305850, mRNA sequence," Jun. 23, 2006 (Rel. 88, last update, version 1) retrieved from EBI accession No. EM_EST:EC565652, with Annex 2: European Patent Office IBIS alignment.
Database EMBL [Online]: accession No. GV773355, "Sequence 80913 from patent U.S. Pat. No. 7,312,035," Jun. 10, 2010 (Rel. 105, last update, version 1) retrieved from EBI accession No. EM_Pat:GV773355, with Annex 3: European Patent Office IBIS alignment.
Database Geneseq [Online]: accession No. AJK18084, "Viral regulatory miRNA SEQ ID No. 270403," Dec. 28, 2007 (first entry) retrieved from EBI accession No. GSN:AJK18084, with Annex 4: European Patent Office IBIS alignment.
Hanihara H et al., "The Detergent Curbing Malodor in Indoor Laundry Drying," Fragrance, No. 223, Sep. 2004, pp. 109-116.
Miyasato, H. et al., "Study on fragrance ingredient (III) of Citrus junos Tanaka," 53rd Symposium on the Chemistry of Terpenes, Essential Oils, and Aromatics, Nov. 7, 2009, No. 1A I-2, Symposium papers pp. 4-6, Nara, Japan.
Kubota, H et al., "Moraxella Species Are Primarily Responsible for Generating Malodor in Laundry," Appl. Envir. Microbiol., May 2012; 78: 3317-3324, (published ahead of print Feb. 24, 2012) Am. Soc. for Microbiology, Washington, DC.
Sugimoto, C et al, "Cellular Fatty Acid Composition Comparisons of *Haemophilus equigenitalis* and *Moraxella* Species," Int. J. Syst. Bacteriol., Apr. 1983; 33: 181-187, Society for General Microbiology, Reading, UK.
Takeuchi, K. et al., "The analysis of the half-dried smell of the wearing apparel." ("Irui no Namakawakishu no Kaiseki"), Japan Society for Bioscience, Biotechnology, and Agrochemistry 2010 (Nendo Taikai Koen Yoshishu), Mar. 2010, abstract 3ACp23, p. 149, Tokyo, Japan.

(Continued)

*Primary Examiner* — Kenneth Horlick
(74) *Attorney, Agent, or Firm* — Sterne, Kessler, Goldstein & Fox, P.L.L.C.

(57) ABSTRACT

A method of evaluating inhibitory effect on damp-dry malodor, containing the steps of: bringing microorganisms which produce damp-dry malodor-causing substances and a test substance into contact with each other in the presence of a sebaceous dirt component; detecting expression of at least one kind of gene selected from a fatty acid desaturase gene and a β oxidation-related enzyme gene derived from the microorganisms; and thereby evaluating a damp-dry malodor inhibitory function of the test substance based on a change in expression amount of the at least one kind of gene.

35 Claims, No Drawings

(56) References Cited

OTHER PUBLICATIONS

Niwano, Y. et al., "Analysis of microorganisms causing of laundry at daily wash cycle," ("Sentaku Cycle ni Okeru Irui no Namakawakishu Gen' in Kin Kaiseki") Fiber Preprints, Japan, vol. 66, No. 1 (Annual Meeting) abstract 2B03, p. 32, Jun. 2011.

Yoshizumi, A. et al., "Causative microorganisms for malodor generation from laundry," ("Irui no Namakawakishu Gen' in Biseibutsu no Kaiseki,") Japan Society for Bioscience, Biotechnology, and Agrochemistry 2011 meeting, (Nendo Taikai Koen Yoshishu), Mar. 2011, p. 102, abstract 2C25p02, Kyoto, Japan.

Munk, S. et al., "Microbial survival and odor in laundry," J. Surfactants and Detergents 4(4): 385-394 (Oct. 2001), AOCS Press, Champaign, IL.

Takeuchi, K. et al., "Identification of novel malodour compounds in laundry," Flavour and Fragrance Journal 27(1):89-94 (2012), published online Sep. 22, 2011, John Wiley & Sons, Ltd., New York, NY.

Takeuchi, K et al., "Review of odorants in human axillary odour and laundry malodour: The importance of branched C7 chain analogues in malodours perceived by humans," Flavour and Fragrance Journal 28(4):223-230 (2013), published online Nov. 28, 2012, John Wiley & Sons, Ltd., New York, NY.

Excerpted file history, U.S. Appl. No. 13/823,851, Mitani et al., (assigned to Kao Corporation), including preliminary amendment filed Mar. 15, 2013, Restriction Requirement dated Nov. 12, 2013, reply to Restriction Requirement filed Dec. 4, 2013, Non-final Rejection dated Dec. 26, 2013, Amendment and Reply filed Mar. 26, 2014, Notice of Allowance dated Apr. 10, 2014, and Issue Notification dated Jun. 18, 2014, downloaded Aug. 19, 2014 from the United States Patent and Trademark Office, Alexandria, VA.

\* cited by examiner

SEQUENCE LISTING

<160> NUMBER OF SEQ ID NOS: 44

<210> SEQ ID NO 1
<211> LENGTH: 1170
<212> TYPE: DNA
<213> ORGANISM: Enhydrobacter aerosaccus SK60

<400> SEQUENCE: 1

```
tatggcacaa cctcaatctt tgaaaacgc gcccatcaat tggatccctg cgtttgtctt      60
aattagcacg cctttggcgg ctttattgat tgtaccttat tacttgtgga cacatagcgt     120
cagttggcaa gtttgggcaa ttttcgcatt ctttatggct tggaatgggt taagtattac     180
cgtcggttat caccgtttat ggtcacatcg tacttaccaa gcgcatccga ttgtcaaatg     240
gttccttctg attggcggca ccttagctgt tcaaggctcg gtatttgact ggtgtgcagg     300
acaccgttta caccaccgcc atgtcgatga tatctatcaa gaccccctact ctgccaagcg    360 tggcttttgg ttctcacata tcgggtggat gctcaaaaac tacccaagcg gccattatga    420
ctacaaaaat atcccagatt taaaagctga tcctgtgtta gtggcgcaag ataaatatta     480
tgccctgtgg attttattgg ccaatattgg cttgccagcg ttgtttggtt ggatggtggg     540
tgatattgca ggtaccttag tacttgcagg gctactgcgt ttggtgttaa gccatcattt     600
tactttcttt atcaactcgc tttgccatat gtttggtacc cgtccttata ccgataccaa     660
caccgcgcgt gataatccga ttctggcgat tttcacttgg ggcgaaggct atcataacta     720
ccaccacttt ttccaatacg actatcgcaa tggggtaaaa tggtggcaat atgatcctag    780
caaatggatt atttatggct tgtcaaaaat cggtttgact tgggatttaa aacgtgtccc     840
agacgtcacc attcagcatg cacaaacaga aatggcattc aaacgtgctg agaaaaaagt     900 tgcgacttt tcagggaatt taaccagcga tttccaagtg ataaagatc gtttaaacag       960 tgaacaacaa gccttcaaac aaacgattgc agaatggcaa gcgttaaaaa cgcaagccat    1020
tgagatgaaa aaaatgagt ttgcccagcg tattcatgaa gtcgatgata agctaaaaga     1080
ccagtttagt ggcattgagg ataaacttcg caatcatgcg cagcaaattg aaaatttggt    1140
taatcattta aaaggtaagc atgtttgatt                                     1170
```

<210> SEQ ID NO 2
<211> LENGTH: 1179
<212> TYPE: DNA
<213> ORGANISM: Moraxella catarrhalis RH4

<400> SEQUENCE: 2

```
atgagtattg agcgtaattc tgaagcgttt gagcaagcac ccatcaactg ggtacctgcc      60
attgtgctgt tatccacctt gtttcttgcc attactatcg tgccttggta tctatggacg     120
catggtgtgg gcatgggcgt ttgggtggct tttgctattt taatggcttg gacgggtctg     180
tctatcactg ctggctacca tcgtttgtgg tcacataaat cctatgaagc ccatcctgtt     240
gtcaaatata ttttattact tggtgcgact ttggcggttg aaagctcagt atttgactgg     300
tgttcagggc atcgctcaca ccatcgccat gttgatgatg aatatgacga cccgtattct     360
tctcgtcgtg gttttggtt tagccacatg ggctggatgc tacgcaaata cccaagcggt     420
caatatgatt acaaaaatat ccccgaccta aaaaaagata agctacttgc cctacaacac     480
aagtattatg gttttgggt aattgccact aatgttgtta ttctagcgat gattggctgg     540
atcacagggg atatgctggg tacatttta gttgcaggtc ttctacgctt ggtattgacg     600 catcattta ccttttttat caactcgctg tgccatatgt ttggtacacg cccttatacc     660
```

```
gatgagaata ccgcacggga caatggccta cttgccatcg tgacttgggg tgaaggttat    720
cataattatc atcactattt tcaatatgac taccgtaatg gcgtcaaatg gtggcaatat    780
gacccaacca aatggatcat cggtctgctt gccaaagtag gcttggccag taatttaaag    840
cgtgtcgatg atttgaccat caaacatgca gagctgacca tgcagtttaa acgcgcccaa    900
gaacgcatcg taacaggggg cgaaccaagt ttagatgagc gtttggccgc ctttaaagag    960
cgtatcagtg ccgagtatga tgaatttacc aaaacggttg aagaatggca taccctaaag   1020
gccaaagcga ttgagctaaa gcgtgcagaa ttagctgacc gattaaatga agcagatgaa   1080
aagctcaaag cacagcttgc ccaaattgaa actaaaatct tagagcaaag taagcgtgtt   1140
gaacaggcat atctacaact caaaggtaaa gccatctga                          1179

<210> SEQ ID NO 3
<211> LENGTH: 1173
<212> TYPE: DNA
<213> ORGANISM: Acinetobacter sp. DR1

<400> SEQUENCE: 3
atgacttccg ccccactcaa agccccaatt aactggaccg ctagcattac cttaattggt     60
ttaccaattc ttgccgcaat cataatcccg atttacgcgt attattatga ttttagtgta    120
agcgcatggg taagcttatt ttttctttta gctctaagta gtatgggat tactgctggt    180 tatcaccgcc tgtgggctca ccgagcttat gaagcgtcgt taccgcttaa aattctttta    240
atgatcggtg aacttttgc cgtacaaaat agtattttgt tctgggcatc tggtcaccgt    300
actcaccaca gacatgttga tcatgtcgat gaagatccat attcaattga gcgtggtttt    360
tggtatgccc atatggggttg gatgatccgt gatcattcgc catctgagcc agactttaaa    420
aatgcacctg acttgctcaa tgataaattg gttatgttcc agcataaata ctatgcttta    480
ctcgtagttg cagttcatgt tggaattttta ggtttaattg gttgggcaac tggcgattta    540
tggggtgtgg tcctcatagg tggtctctta cgattaatca ttagccatca agtgactttc    600
tttattaact cactttgtca tatgtttggt aaacgtcctt atacagacga aaactcggca    660
cgtgataatt tctggttagc tatcgccact tggggcgagg gttaccacaa ctatcaccat    720
atcttccaat acgattatcg taatggtgtg aaatggtggc aatatgaccc aacaaaatgg    780
ttgatttggt cttgttctaa acttggttta gctaaaaatt tacgtcgtat tccaagcttt    840
aatattaaaa aagcagaact ggcgatgaag tttaaatatg ccgagcaaga tcttgctatc    900
tatggtcatg atgtaaatgc tgacattagt caaatgaaac aacgtattgc acaagaatac    960
gaagcattta cccatacttt aaatgattgg gcaaaactta agaacaaga gttacaagcg   1020 aaaaaagcag caatggctga aaagattcat agaatggatc acaagcttaa agttgatttt   1080
cagttgcttg aacaccgttt aagtcatcac cgtgaatgct tagaaacact tatgcgtagt   1140
gttaaaaaga ataccaacgt ggtgtcagac taa                                1173

<210> SEQ ID NO 4
<211> LENGTH: 1533
<212> TYPE: DNA
<213> ORGANISM: Saccharomyces cerevisiae YGL055W

<400> SEQUENCE: 4
atgccaactt ctggaactac tattgaattg attgacgacc aatttccaaa ggatgactct     60
gccagcagtg gcattgtcga cgaagtcgac ttaacggaag ctaatatttt ggctactggt    120
```

-continued

```
ttgaataaga aagcaccaag aattgtcaac ggttttggtt ctttaatggg ctccaaggaa      180
atggtttccg tggaattcga caagaaggga acgaaaaga agtccaattt ggatcgtctg       240
ctagaaaagg acaaccaaga aaaagaagaa gctaaaacta aaattcacat ctccgaacaa      300
ccatggactt tgaataactg caccaacat ttgaactggt tgaacatggt tcttgtttgt       360
ggtatgccaa tgattggttg gtactttgct ctctctggta aagtgccttt gcatttaaac      420
gttttccttt tctccgtttt ctactacgct gtcggtggtg tttctattac tgccggttac      480
catagattat ggtctcacag atcttactcc gctcactggc cattgagatt attctacgct      540
atcttcggtt gtgcttccgt tgaagggtcc gctaaatggt ggggccactc tcacagaatt      600
caccatcgtt acactgatac cttgagagat ccttatgacg ctcgtagagg tctatggtac      660
tcccacatgg gatggatgct tttgaagcca atccaaaat acaaggctag agctgatatt       720
accgatatga ctgatgattg gaccattaga ttccaacaca gacactacat cttgttgatg      780
ttgttaaccg ctttcgtcat tccaactctt atctgtggtt acttttttcaa cgactatatg     840
ggtggtttga tctatgccgg ttttattcgt gtctttgtca ttcaacaagc taccttttgc      900
attaactcct tggctcatta catcggtacc caaccattcg atgacagaag aaccctcgt       960
gacaactgga ttactgccat tgttactttc ggtgaaggtt accataactt ccaccacgaa     1020
ttcccaactg attacagaaa cgctattaag tggtaccaat cgacccaac taaggttatc      1080
atctatttga cttctttagt tggtctagca tacgacttga agaaattctc tcaaaatgct     1140
attgaagaag ccttgattca acaagaacaa aagaagatca ataaaaagaa ggctaagatt     1200
aactggggtc cagttttgac tgatttgcca atgtgggaca acaaaccctt cttggctaag     1260
tctaaggaaa acaagggttt ggttatcatt tctggtattg ttcacgacgt atctggttat     1320
atctctgaac atccaggtgg tgaaacttta attaaaactg cattaggtaa ggacgctacc     1380
aaggctttca gtggtggtgt ctaccgtcac tcaaatgccg ctcaaaatgt cttggctgat     1440
atgagagtgg ctgttatcaa ggaaagtaag aactctgcta ttagaatggc tagtaagaga     1500
ggtgaaatct acgaaactgg taagttcttt taa                                  1533
```

<210> SEQ ID NO 5
<211> LENGTH: 2157
<212> TYPE: DNA
<213> ORGANISM: Enhydrobacter aerosaccus SK60

<400> SEQUENCE: 5

```
atgatttatc aaggaaatag catctcggta tcgctactcg aagacggtat tgctaaatta       60
aactacgata atcaaactga gagcgttaat aaatttgacc aaaccaccat caaagaattt      120
ggcgaagcag tcacggcatt agaacaatct tcagacgtta aggtctcat cgttacttca       180
ggaaaaaaag ttttcatcgc tggtgcggac atcactgaat tgttggtaa cttcaaaaaa       240
ccagaaggcg agattgcttc ttgggtactt gacatcaaca aaacattcaa ccgttttgaa      300
gacctgcctt tcccaaaagt tgccgcaatc aatggtgcat ccatgggcgg tggtacagag      360
atgacgttgg tgtgtgatta ccgtgtcatg agtgacaaag cgagcatcgg tttgcccgaa      420
gttaaattgg gtatcttccc aggctttggt ggttcagtgc gtttgccacg tatcatcggt      480
atcgataacg cttttagaaat catcgcaact ggcgaggcac aaaaaccagc cgctgcattg     540
aaagtcggta tggtggatgc ggttgttgcc gctgaccagt tagaagcttc agcgattgat      600
ttagtcaaaa aatgtatcgc aggcgatcta gattggaaag cacgccatga cgaaaaaatc      660
aatccagtca aattaaacgc cctagaacaa accatggcat ttaactcagc caaaggtgta     720
```

```
ctgttctcaa aagccaatcc agcgcagtac ccagcgccaa aaatcgcctt agagtctatc    780
gaaagacacg tgaacctacc acgtgacaaa gctttagaaa ttgaatctgc aggttttgca    840
aaagcagcaa aaaccccaca agcagaaagc ctagtcggtc tattcttaaa cgaccaagcc    900
gttcgcaaac tcgctaaaac tcacagcgcc aaagcgcatg atattaaaga agctgctgta    960
ttgggcgcag gtatcatggg tggcggtatc gcttaccaag ctgcctcaaa aggcttgccc   1020
atcatcatga agacatcaa ggcagagcaa cttgacttag gtatgagcga ggccagcaaa    1080
cacctatcaa gtggtatggc acgcggtaaa gtaaccccag cacaaatggg cgaaacttta   1140
agccgtatcc gtcctacgct caactacggt gattttggtg agactgacat cgtgattgaa   1200
gcggttgttg aaaatccaaa agttaaacac gcggtattaa agaagttga agggctagtt    1260 aaagacaact gtattctagc atctaacact tcgaccatct ctatcaccta cttagcttcg   1320
gtactagagc gcccagaaaa cttcgtcggc atgcacttct ttaatccagt ccatcgtatg   1380
ccgctggttg aagtaattcg tggtgaaaaa tcaagcgaag aagcggtagc gactacggta   1440
gcgttagcag aaaaaatggg taaagtgccc gtggtggtaa atgactgccc aggcttctta   1500
gtaaaccgcg tattattccc ttacttcggt gcctttgact tattgatcaa caaggcgct    1560 gattttgttc aaattgacaa agtcatggaa aaatttggct ggccaatggg tcctgcttac   1620
ttgatggacg ttgtgggtat tgacacaggc gttcatgggg cagaagtcat ggcggaaggc   1680
ttcccagacc gtatgaaacc agactacaaa gtgagcggtc agatattgtt tgaagccaat   1740
cgcttaggtc aaaaaaatgg cgttggtttc tacaaatacg aaacggataa aaaaggtaag   1800
ccagttaaaa ctgccgatcc acaaaccgtt gaattattaa aaccatttat cgatgcgcca   1860
aaacagtttg aagaccaaga aatcatcgat cgtctgatga ttgcattatg taatgaaacg   1920
gttcgctgtt tagaagataa catcgtatcg accccctgcag aagcagacat ggcgatgatt   1980
atgggtattg gcttcccgcc attccgtggt ggcccatgtc gttacatcga ccaaatcggt   2040
ctacaaaatt acctagccct tgcgacaaa tacgcaagct taggtaaagc ctatgaagcg    2100
ccacaaatga ttcgtgatat ggcggcaaat ggtaaaactt tttacccaca agcgtaa      2157
```

<210> SEQ ID NO 6
<211> LENGTH: 2154
<212> TYPE: DNA
<213> ORGANISM: Moraxella catarrhalis RH4

<400> SEQUENCE: 6

```
atgatttatc aaggaaaaaa tattcaggtc gatttttttg accaaacaca aggtatcgtg     60
cagtttcatt ttaatgccac tgatgaaagc gttaataaat ttgatcgcaa aaccactcaa    120
gaatatcaag aagcggtaac agtacttgaa accgtgatg atattcaagg cttaattgtc     180
acttcaggta atcggtgtt tattgctggt gcggatatta ctgagtttac cgaatatttt    240
agtcgctcta aagatgaaat tgaggcatgg cttttggata tcaatcatat ttttaatcgc    300
tttgaggatt tgcccttccc aaaagtggcg gcgattaatg gtgcagcgtt aggcggtggc    360
tgtgagatgg ctttggtatg cgattaccgt gtggcgggta tttctgccca aattggtttg    420
cctgaaacta agcttggtat ttttccaggt tttggtggtt cagtgcgtct gccacgcctg    480
attggcattg ataacgccct tgaggccatt gcgacaggta aggcttatcg acctgatgaa    540
gcacttaaat tgggattggt tgatgcgtg gtggctgatg agctgcttga gcaggcagcg    600
gctgattggg tcaaaaaatg cttattaggc aagtttgatt ggcaggcgaa agcgtcaagaa   660
```

-continued

```
aaacaagtac cagttaagct caatcagctg gagcaggcaa tggcatttaa ttcggctaag      720
ggtgtcattt ttgccaaagc caatccaaaa cattatcctg cggtggcgat tgcccttgag      780
accatcgaaa aacacgccaa tttaaaccgt gatgatgcga ttgcccttga agccaaaggt      840
tttacaaaag ctgcaacaac cccacaagcg gccgccttgg tcggcttatt tttaaatgac      900
caaacagtta aaaaacttgc caaaaagcac agtcaaaatg cacaaaccat caagcaagca      960
gctgtacttg gtgcaggtat catgggtggc ggtatcgctt atcaggcagc ggtcaagggc     1020
ttgccaatta ttatgaaaga cattcaagcc aagcagttag accttggcat gaatgaagct     1080
ggtaaactgt tatcaaaaga ggttttgcgt ggtaaatcaa cgccagctaa gatggctcaa     1140
accttaagcc acattcgccc aaccttaaac tatggcgatt ttggtgaagt tgatattgtg     1200
attgaggcgg tcgttgaaaa tcctacaatc aaagaagcgg tattgtctga ggtgagggc      1260
ttggtaaaac aagagaccat tttggcctca aatacctcaa cgatttctat cactcgcttg     1320
gcgaatgccc taaaacgccc cgaaaacttt gtgggtatgc actttttta cccagtacat      1380
cgcatgccat tagttgaggt gattcgtggc gagaagacca cgcgatatcgc cattgcaaca    1440
acggttgcat ggcacaaaaa aatgggcaaa actccaattg tcgtcaatga ctgcccagga    1500
tttttggtga atcgtgtgtt atttccttat tttggtgcgt tcgatttgct ggtcaaagaa     1560
ggtgccgatt tgttagtat tgataagacc atggaaaaat ttggctggcc gatgggtcct     1620
gcgtatcttt tggatgttgt gggtatggat acaggcgtgc atgctgccaa ggtgatggca    1680
gagggtttcc ctgatcgtat gaagccagat tataaaggtg caacgcagct gatgtttgag    1740
catgagcgtt tgggtcaaaa aaatggtgtt ggttttatc aatatgaaac tgataagcgt     1800
ggcaaaccta aaaaattgc cgatagtacc acttatgagc tgttaaactt ggttcaaact     1860
ggcgatcaga cttttgatga gcaagaaatt atcgaccgca tgatgattgc attttgcaat    1920
gaaaccgtac gctgcttgga agataatatc gtcgcaagcc tgctgaagc tgatatggcg     1980
atgattatgg gcgtaggttt cccaccattt cgtggcggcc cttgccgata tatcgaccaa    2040
atcggtgtcg caaactatgt tgcattgtgc gataagtacg catatttagg taaggcatat    2100
gaagcacctg ccaaattgcg tgatatggct caaaatggcg agacttttta ctaa          2154
```

<210> SEQ ID NO 7
<211> LENGTH: 2154
<212> TYPE: DNA
<213> ORGANISM: Acinetobacter sp. DR1

<400> SEQUENCE: 7

```
atgatccacg ctggcaatgc cattaccgtc caaatgcttt cggacggaat tgcagaattc       60
cgctttgact acaaggtga gtcggtcaat aaatttaacc gtgcaacaat tgaagatttc      120
caagctgcta ttgctgcggt aaaagcaaat aatgatatta aaggcttagt tgttacgtcg      180
ggcaaatcaa catttattgt tggggcagac attaccgaat ttggtgaaaa cttcgctcaa      240
ggcgaaaaag cgattgttga ctggcttatg cctgttcacg aaatcttcaa tagctttgaa      300
gatttagaaa ttccaaaagt tgttgctatt aacggtatgg cgttaggcgg cggttttgaa      360
atgtgtttag tgtgtgacta tcgtgtgatg tcagaagctg cgcaagtggg cttaccagaa      420
attaaacttg gtatttaccc aggttttggc ggtagcgtac gtttaagccg tcttattggt      480
atcgacaacg cggttgaatg gatggcgatg gctgctccta aaaaccagc tgctgcacta     540
aaagatggtg ctgtagatgc ggttgtagct gctgataaat tacttgaagc tgcaactgac      600
ttagttaagc aagcaatttc tggtcgtttg aactggaaag cgaaacgcca agaaaaactt      660
```

```
gatgctgtaa aattgaaccc acttgaacaa atgatggcgt tcaacacagc aaaaggtgct      720
gtacttgcta aagcaaatcc tgctcaatac cctgctccaa aattattact tgattcatta      780
caagcaggtg caagccttgc gcgtgacgaa gcattaaaag ctgaagctga aggttttgca      840
aaagctgcga ttactccaca agctggtgca ttgattggtt tattcctcaa tgaccaagtt      900
gttaagaaaa ctgctaaaaa acatgaaaaa ggtgctcacc ctgtaaacca agcagctgta      960
cttggcgctg gtatcatggg tggtggtatt gcttaccaag cggcaagcaa aggcactcca     1020
attatcatga aagatattgg taacccacaa cttgcactag gtatgtcaga agcgaacagc     1080
ttgttaacta aacaagttga acgtaagaaa atgaaacctg cgcaaatggg tgaaacccct     1140
gcacgtatcc gtcctacttt aagctacgat gagtttaaag aagtcgacat cgtgatcgaa     1200
gcggttacag aaaatccaaa agttaaagaa atcgttcttg cagacactga aaagcatgtt     1260
cgtgaaaaca cgattattgc gtctaacacg tctacaattt caattacacg tttagcgaaa     1320
gctttacaac gtcctgaaaa ctttgtaggt atgcacttct tcaacccagt tcacatgatg     1380
ccgcttgtag aagtcattcg tggtgaaaag acttctgaag aagcgattgc aactactgtt     1440
gttcttgctc aaaaaatggg taaaacacca atcgttgtaa acgactgccc agggttcttg     1500
gttaaccgtg tattgttccc ttactttggt gcatttgacc ttcttgtaaa agacggcgca     1560
gacttccagc aagttgacaa tgtaatgtct aagtttggct ggccaatggg tcctgcttac     1620
ctcatcgacg ttgttggtat cgacactggt gtacacggtg cagaagtcat ggctgaaggt     1680
ttcccagacc gcatgaagcc agactacaaa ggttcaatcc aagcaatgta cgaagctaaa     1740
cgtcttggtc aaaagaatga cgttggtttc tacaaatacg aactcgataa gaaaggcaag     1800
aaagcaaaaa ctgttgatcc aacagcgtat gaaatcattg ctcctttcgt aacgggtgaa     1860
aaacgcgagt ttgataacca agaaatcatt gaccgcatga tgcttgcttt ctgtaacgaa     1920
acagttcgtt gcttagaaga caacatcgtt gcaactgctg ctgaagcaga catggcaatg     1980
attatgggtg taggtttccc tccattccgt ggtggtccat gtcgttatat cgaccagaca     2040
ggtgttgctg aatatgttgc gctttgcgac aaatatgcac acttaggtaa ggcttatgaa     2100
gcgccacaaa tgttgcgtga catggctgct aacaacaaaa aattctacgg ttaa            2154
```

<210> SEQ ID NO 8
<211> LENGTH: 2190
<212> TYPE: DNA
<213> ORGANISM: Escherichia coli K12 MG1655

<400> SEQUENCE: 8

```
atgctttaca aaggcgacac cctgtacctt gactggctgg aagatggcat tgccgaactg       60
gtatttgatg ccccaggttc agttaataaa ctcgacactg cgaccgtcgc cagcctcggc      120
gaggccatcg gcgtgctgga acagcaatca gatctaaaag ggctgctgct gcgttcgaac      180
aaagcagcct ttatcgtcgg tgctgatatc accgaatttt tgtccctgtt cctcgttcct      240
gaagaacagt taagtcagtg gctgcacttt gccaatagcg tgtttaatcg cctggaagat      300
ctgccggtgc cgaccattgc tgccgtcaat ggctatgcgc tgggcggtgg ctgcgaatgc      360
gtgctggcga ccgattatcg tctggcgacg ccggatctgc gatcggtct gccggaaacc      420 aaactgggca tcatgcctgg ctttggcggt tctgtacgta tgccacgtat gctgggcgct      480
gacagtgcgc tggaaatcat tgccgccggt aaagatgtcg cgcgcgatca ggcgctgaaa      540
atcggtctgg tggatggcgt agtcaaagca gaaaaactgg ttgaaggcgc aaaggcggtt      600
```

```
ttacgccagg ccattaacgg cgacctcgac tggaaagcaa acgtcagcc gaagctggaa    660 ccactaaaac tgagcaagat tgaagccacc atgagcttca ccatcgctaa agggatggtc   720
gcacaaacag cggggaaaca ttatccggcc cccatcaccg cagtaaaaac cattgaagct   780
gcggcccgtt ttggtcgtga agaagcctta aacctggaaa acaaaagttt tgtcccgctg   840
gcgcatacca acgaagcccg cgcactggtc ggcattttcc ttaacgatca atatgtaaaa   900
ggcaaagcga gaaactcac caaagacgtt gaaaccccga acaggccgc ggtgctgggt     960 gcaggcatta tgggcggcgg catcgcttac cagtctgcgt ggaaaggcgt gccggttgtc  1020
atgaaagata tcaacgacaa gtcgttaacc ctcggcatga ccgaagccgc gaaactgctg  1080
aacaagcagc ttgagcgcgg caagatcgat ggtctgaaac tggctggcgt gatctccaca  1140
atccacccaa cgctcgacta cgccggattt gaccgcgtgg atattgtggt agaagcggtt  1200
gttgaaaacc cgaaagtgaa aaaagccgta ctggcagaaa ccgaacaaaa agtacgccag  1260
gataccgtgc tggcgtctaa cacttcaacc attcctatca gcgaactggc caacgcgctg  1320
gaacgcccgg aaaacttctg cgggatgcac ttctttaacc cggtccaccg aatgccgttg  1380
gtagaaatta ttcgcggcga gaaaagctcc gacgaaacca tcgcgaaagt tgtcgcctgg  1440
gcgagcaaga tgggcaagac gccgattgtg gttaacgact gccccggctt ctttgttaac  1500
cgcgtgctgt tcccgtattt cgccggtttc agccagctgc tgcgcgacgg cgcggatttc  1560
cgcaagatcg acaaagtgat ggaaaaacag tttggctggc cgatgggccc ggcatatctg  1620
ctggacgttg tgggcattga taccgcgcat cacgctcagg ctgtcatggc agcaggcttc  1680
ccgcagcgga tgcagaaaga ttaccgcgat gccatcgacg cgctgtttga tgccaaccgc  1740
tttggtcaga gaacggcct cggtttctgg cgttataaag aagacagcaa aggtaagccg   1800
aagaaagaag aagacgccgc cgttgaagac ctgctggcag aagtgagcca gccgaagcgc  1860
gatttcagcg aagaagagat tatcgcccgc atgatgatcc cgatggtcaa cgaagtggtg  1920
cgctgtctgg aggaaggcat tatcgccact ccggcggaag cggatatggc gctggtctac  1980
ggcctgggct ccctccgtt ccacggcggc gcgttccgct ggctggacac cctcggtagc   2040
gcaaaatacc tcgatatggc acagcaatat cagcaccctcg gcccgctgta tgaagtgccg  2100
gaaggtctgc gtaataaagc gcgtcataac gaaccgtact atcctccggt tgagccagcc  2160
cgtccggttg cgacctgaa aacggcttaa                                    2190
```

<210> SEQ ID NO 9
<211> LENGTH: 1686
<212> TYPE: DNA
<213> ORGANISM: Enhydrobacter aerosaccus SK60

<400> SEQUENCE: 9

```
atggaaaatt tttggacaaa atttttatgac cctgccaccg ccgcacacat tcccgcttta    60
acagatcaat cgttaataga attttttgat gatcgtttaa cggcctttgc ctcccgagaa   120
ttcaccagca atatggagcg agctatcagc tacaaagaag tggataacgt cgcacgccta   180
gtcagccgct ggctacaagc ccaatcctta agcgcaaatg ccagtgtcgc tatcatgctg   240
cctaatgtac aagcgtattt accggtcatg ataggtgcga ttcgctcagg gtatgttttg   300
acgccgatta atccgctaca taccgctcgt gaattagagt ttcagttgat tgatgccaat   360
accgaagtta ttttttatttt agaaaatttt gctcacactt tacaaaaaat cattgataaa   420 acccccagtga aaaagtcgt gattatccgt ttaggagact tgttaggatt aaagggtaaa   480
atagtcgata tcgctgtaaa atatgtcaag aatatggtag cgccttacca aattgaccaa   540
```

-continued

```
aagtatcagc cattacgatt gggtcaagtg atgaaaaccg ctaaatccat gccttaccaa      600
aagccatcca aatcacttga tgatgttgcc tttatccaat acaccggcgg caccactggc      660
agacccaaag gcatcttgct gacccatcga aatattttga cagcagttga gcaatactat      720
cagtggtttt tgccggtact caaccaacaa aaaaatgtcg aacaagtatt ccatagtatc      780
ctagcgttgc cgctatatca tatctttgcg tttatctttt ccatgttagg catgaaatct      840
ggcatgcgca tgaccttggt gaccaaccct aaagacattg ccagttttat caaaatatta      900
tctgctaagc cgtttcacat tcttcctggg gttaatacct tgtttcaggc attagttaac      960
caccccgatt ttaaaagtgt cgatacccgt gaactaaaat tatcaatcgc cggcggtatg     1020
gcagccaccc ccgccacggc caaggcttgg cttgagctta caggctgccc cttaatagaa     1080
ggatggggca tgtccgaaac tatcggtgca ggcacgtgta acccgctcac caatcatgag     1140
tacactggcg atattggcct acctttaccg agtatcaata tcaaaatctg tgatgatgtg     1200
ggcaacgaag tggcgttagg cgaagtgggt gagatctgta tcaaaggtga taatgtgact     1260
ataggttatc ataacattga caataccgat tatttcttac ctgaaggcca tttaaagaca     1320
ggcgacattg ggatgatgat gcaaaacggg catatcaaat taatggatcg caaaaaagat     1380
atgctgattg tcagtggctt taatgtctat ccaaccgaaa ttgaagcggt gctgttaaat     1440
cacccgaaag tccaagaatg tgccgtgatt ggcgttgaag atgcgcttca agggcaatcg     1500
gttaaagcct atattgtcaa atcagatgac agtttgacga tagatgagct taaagccttt     1560
agtcatgagc aattaaccgg gtataaacga ccacgtcaat atacgtttat tgagcaatta     1620
cccaaaaccg cggttggcaa aattcaaaaa actgaactgc ggttacttga aaaaatagt     1680 aaataa                                                                1686
```

<210> SEQ ID NO 10
<211> LENGTH: 1707
<212> TYPE: DNA
<213> ORGANISM: Moraxella catarrhalis RH4

<400> SEQUENCE: 10

```
atgagtaaca tgactgattt taccgtttca acggatgcac cttggtataa aacctatcaa       60
gaacatggtc ttgattttaa cttttgatttg cctgacaata tcaattcact catggatatt      120
tttgatcagg catttgcacg cttcggtaat caagttgcgt ttacttgcat ggataaatct      180
atcacctatc gacaactgga taactatagt cgtcaaatgg cggcatattt acaatcgcta      240
ggcttggtca aggtgataaa agtagcggtc atgatgccaa atattttgca atatccgatt      300
gcgatgattg cgattgtgcg tgccggattg acattggtga atgtcaaccc tttgtatacc      360
tcgaatgagc ttgaacatca gctcaatgac tcagaagcta aagcgttatt tattgtagaa      420
aattttgctc atacttttga aaagtggtt aataaaggtc aagttcgcca tgtaattgtt       480
gcatctttgg gcgatatgct tggcttaaaa ggcttttttgg tcaatgcagt ggtgcgtcat      540
gttaaaaaaa tggtgcctga atggaatatc cctggtcatg tatcatttaa agacgcactc      600
aacaaagtgc cgataggtaa ctacaatcgc cctaatttgg ctttggatga tattgctgta      660
ttgcagtata caggcggtac aacaggcgtg gcaaaaggtg cgatgctcac ccatcgtaat      720
cttgcttcaa atgttgagca gtgtgcgcca tttcttagct tggtattttc taaagacaat      780
ctatctggtc agtatatcgc agttgcctta ccgctttacc atattttttc attcacagcg      840
tgtggtttgt tggggatgaa gatgggtttt agtatgttat taattaccaa cccaagagat      900
```

| | |
|---|---|
| tttccagcac tgtgtaaaga ttatgccaaa tataagcctg cattttttcc tgcagtgaat | 960 |
| actttattta atggtttggt gcatcatgaa ggatttcggt cacttgacca tagtaattta | 1020 |
| aaattatcat taggcggtgg catgtcagtt ttatccgata ctgccaaagc atgggagcgt | 1080 |
| ttgacgggta attatatcat cgaaggctat ggtttatctg aaacctcgcc tgttttgacc | 1140 |
| ctaaatccac caggtggata cacaggtaag attggcattc caattcctgc caccgacatt | 1200 |
| aaaattttgg atgatgaggg caacgagttg gcgatgggcg aggctggtga atttgtgcc | 1260 |
| aaaggtccac aaatcatggt cggctactgg aatcgccttg atgaaaccga aaaggttatg | 1320 |
| accaaagatg ggttttttcg tacaggcgat attggtgtga tggatgatcg tggctttatt | 1380 |
| aaaattgttg atcgcaaaaa agatatgatt ttggtgtctg gatttaatgt ctatcccaat | 1440 |
| gaggttgaag atatcattac tgcccatcca aaagtcattg aatgtggcgt gattggtgtg | 1500 |
| cctgatgatc acagtggtga agtggttaag gtctttgtgg tcaaaaaaga tccctccttg | 1560 |
| accgccgacg aggtgcgtgc ttgggcaaaa gaaaacctaa caggttacaa acgccccaaa | 1620 |
| tatattgagt ttatcagtga gcttcccaaa tctaatgttg gtaaaatttt gcgtaaggaa | 1680 |
| ttaagagtac ttgagcaaag caaataa | 1707 |

<210> SEQ ID NO 11
<211> LENGTH: 1680
<212> TYPE: DNA
<213> ORGANISM: Acinetobacter sp. DR1

<400> SEQUENCE: 11

| | |
|---|---|
| atggaaaaaa tttggtttgc agaataccaa aaaacaggga ttccagaaac agtagcattg | 60 |
| cctgcggaaa atacttcact tgttgatatt tttgagagta atttccaaaa atttggttct | 120 |
| cgcgatgcct ttatctttat ggataaagcg atgtcattta atgagttaga gcttgcaagc | 180 |
| cgtaagttcg cgacctattt gcaaaatttg gggttagcaa aaggaactcg tgtggcagtg | 240 |
| atgatgccga atgtattgca gtatcctgta gttgcattag ctgtgttacg tgcaggtttg | 300 |
| gtgttagtaa acgttaaccc actttatact gcgcgtgaac ttgagcatca attaaatgac | 360 |
| tcaggtgcag aagtccttgt gattatcgaa aactttgcca gtgtttacca agcattttta | 420 |
| ggtaaaactc cagtgaagca tgttgtagtt gcatcagtag agacatgctc ggtacactc | 480 |
| aaaggtactc tggtgaattt tgtactacgt aaagtacgta aacaaattcc agcttggaat | 540 |
| attccagggc acgttaaatt taactcagca ttaaataaag aaaatgcgag taattataag | 600 |
| cgtccgactt taactttaag tgatactgct gtacttcaat acactggtgg tacaacaggc | 660 |
| gtttcaaaag gtgcagagct tactcatcgt aatcttgtag caaacttact tcagtgtgat | 720 |
| ggtatttttcc aaagtaaatt tggagcaaat gatggcgcta aaggcgaccg tattgtttgt | 780 |
| gcattaccgc tttatcatat ttttgcgttc atggtttgcg cgatgtacgg tatgtataaa | 840 |
| ggtcaggcaa atatcttgat tccgaaccct cgtgatttac cagctgttat taacgaatta | 900 |
| cgtaaatatc aaccatcatt cttcccagcg gtaaacacat tgtttaatgc tttagtgaac | 960 |
| aatgaagaat tcaaacaact tgaccatagc aatttaaaaa tggcgatggg cggtggtatg | 1020 |
| gccgttttac cttctacagc agaagcgtgg aagaaaatta ctggtacaac cattattgaa | 1080 |
| ggttatggct tgtcagaaac ttcaccggta gcaactgcaa atccacctgc ttctactgaa | 1140 |
| tttagcggca ctattggtat tccgttacct ttaactgaag ttgctatttt agatgatgat | 1200 |
| ggtaaagaag ttgctttagg tgaacaaggc gaaatctcga ttcgtggtcc tcaagtgatg | 1260 |
| aagggttact ggaatcgtcc tgatgagaca gctaaagtca tgacagcaga tggtttcttc | 1320 |

| | |
|---|---|
| cgtacgggtg acatcggcgt gatggatagt cgtggatata caaaaattgt agaccgtaaa | 1380 |
| aaggatatga ttttggtttc tggctttaac gtttacccaa gtgaaatcga agaagttatt | 1440 |
| gctaaacatc caaaagtatt ggaagttgca gcgattggtg ttccagatga aaaatcaggt | 1500 |
| gaagtgccaa aactctttat tgtgaaaaaa gatcaaagct taacgactga agaagttttg | 1560 |
| agcttcgcta aagaaaactt aacaggctat aaacgccctc gttatgttga gtttatggat | 1620 |
| gaattaccaa atcaaatgt aggcaaaatt ttacggaaag acttacgtaa accagcctaa | 1680 |

<210> SEQ ID NO 12
<211> LENGTH: 1686
<212> TYPE: DNA
<213> ORGANISM: Escherichia coli K12 MG1655

<400> SEQUENCE: 12

| | |
|---|---|
| ttgaagaagg tttggcttaa ccgttatccc gcggacgttc cgacggagat caaccctgac | 60 |
| cgttatcaat ctctggtaga tatgtttgag cagtcggtcg cgcgctacgc cgatcaacct | 120 |
| gcgtttgtga atatggggga ggtaatgacc ttccgcaagc tggaagaacg cagtcgcgcg | 180 |
| tttgccgctt atttgcaaca agggttgggg ctgaagaaag gcgatcgcgt tgcgttgatg | 240 |
| atgcctaatt tattgcaata tccggtggcg ctgtttggca ttttgcgtgc cgggatgatc | 300 |
| gtcgtaaacg ttaacccgtt gtataccccg cgtgagcttg agcatcagct taacgatagc | 360 |
| ggcgcatcgg cgattgttat cgtgtctaac tttgctcaca cactggaaaa agtggttgat | 420 |
| aaaaccgccg ttcagcacgt aattctgacc cgtatgggcg atcagctatc tacggcaaaa | 480 |
| ggcacggtag tcaatttcgt tgttaaatac atcaagcgtt tggtgccgaa ataccatctg | 540 |
| ccagatgcca tttcatttcg tagcgcactg cataacggct accggatgca gtacgtcaaa | 600 |
| cccgaactgg tgccggaaga tttagctttt ctgcaataca ccggcggcac cactggtgtg | 660 |
| gcgaaaggcg cgatgctgac tcaccgcaat atgctggcga acctggaaca ggttaacgcg | 720 |
| acctatggtc cgctgttgca tccgggcaaa gagctggtgg tgacggcgct gccgctgtat | 780 |
| cacattttg ccctgaccat taactgcctg ctgtttatcg aactgggtgg gcagaacctg | 840 |
| cttatcacta cccgcgcga tattccaggg ttggtaaaag agttagcgaa atatccgttt | 900 |
| accgctatca cgggcgttaa caccttgttc aatgcgttgc tgaacaataa agagttccag | 960 |
| cagctggatt tctccagtct gcatctttcc gcaggcggtg ggatgccagt gcagcaagtg | 1020 |
| gtggcagagc gttgggtgaa actgaccgga cagtatctgc tggaaggcta tggccttacc | 1080 |
| gagtgtgcgc cgctggtcag cgttaaccca tatgatattg attatcatag tggtagcatc | 1140 |
| ggtttgccgg tgccgtcgac ggaagccaaa ctggtggatg atgatgataa tgaagtacca | 1200 |
| ccaggtcaac cgggtgagct ttgtgtcaaa ggaccgcagg tgatgctggg ttactggcag | 1260 |
| cgtcccgatg ctaccgatga aatcatcaaa atggctggt tacacaccgg cgacatcgcg | 1320 |
| gtaatggatg aagaaggatt cctgcgcatt gtcgatcgta aaaaagacat gattctggtt | 1380 |
| tccggtttta acgtctatcc caacgagatt gaagatgtcg tcatgcagca tcctggcgta | 1440 |
| caggaagtcg cggctgttgg cgtaccttcc ggctccagtg gtgaagcggt gaaaatcttc | 1500 |
| gtagtgaaaa aagatccatc gcttaccgaa gagtcactgg tgacttttg ccgccgtcag | 1560 |
| ctcacgggat acaaagtacc gaagctggtg gagtttcgtg atgagttacc gaaatctaac | 1620 |
| gtcgaaaaaa ttttgcgacg agaattacgt gacgaagcgc gcggcaaagt ggacaataaa | 1680 |
| gcctga | 1686 |

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide for amplifying a part of the
      nucleotide sequence of the delta9desaturase gene, primer des_F1

<400> SEQUENCE: 13
cgctgtgcca tatgtttggt                                                20

<210> SEQ ID NO 14
<211> LENGTH: 19
<212> TYPE: DNA
<213> ORGANISM: Artificial Sequence
<220> FEATURE:
<223> OTHER INFORMATION: Oligonucleotide for amplifying a part of the
      nucleotide sequence of the delta9desaturase gene, primer des_R1

<400> SEQUENCE: 14
tgccaccatt tgacgccat                                                 19

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the delta9desaturase gene, primer des_F2

<400> SEQUENCE: 15
gatggtgggt gatattgcag gta                                            23

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the delta9desaturase gene, primer des_R2

<400> SEQUENCE: 16
atcggtataa ggacgggtac caa                                            23

<210> SEQ ID NO 17
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the delta9desaturase gene, primer des_F3

<400> SEQUENCE: 17
cccgtcctta taccgatacc aac                                            23

<210> SEQ ID NO 18
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the delta9desaturase gene, primer des_R3

<400> SEQUENCE: 18
ccattttacc ccattgcgat agt                                            23

```
<210> SEQ ID NO 19
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the delta9desaturase gene, primer des_F4

<400> SEQUENCE: 19
acccgtcctt ataccgatac caa                                              23

<210> SEQ ID NO 20
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the delta9desaturase gene, primer des_R4

<400> SEQUENCE: 20
ccattttacc ccattgcgat agt                                              23

<210> SEQ ID NO 21
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the delta9desaturase gene, primer des_F5

<400> SEQUENCE: 21
gatggtgggt gatattgcag gta                                              23

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the delta9desaturase gene, primer des_R5

<400> SEQUENCE: 22
cggtataagg acgggtacca aac                                              23

<210> SEQ ID NO 23
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the delta9desaturase gene, primer des_F6

<400> SEQUENCE: 23
ggtatttgac tggtgtgcag gac                                              23

<210> SEQ ID NO 24
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the delta9desaturase gene, primer des_R6

<400> SEQUENCE: 24
gcttgggtag tttttgagca tcc                                              23

<210> SEQ ID NO 25
```

<210> SEQ ID NO 25
<211> LENGTH: 23
<212> TYPE: DNA
<213> ORGANISM: Artificial Sequence
<220> FEATURE:
<223> OTHER INFORMATION: Oligonucleotide for amplifying a part of the nucleotide sequence of the fadB gene, primer fadB_F6

<400> SEQUENCE: 25
tgaaacggtt cgctgtttag aag                                    23

<210> SEQ ID NO 26
<211> LENGTH: 23
<212> TYPE: DNA
<213> ORGANISM: Artificial Sequence
<220> FEATURE:
<223> OTHER INFORMATION: Oligonucleotide for amplifying a part of the nucleotide sequence of the fadB gene, primer fadB_R6

<400> SEQUENCE: 26
gaatcatttg tggcgcttca tag                                    23

<210> SEQ ID NO 27
<211> LENGTH: 23
<212> TYPE: DNA
<213> ORGANISM: Artificial Sequence
<220> FEATURE:
<223> OTHER INFORMATION: Oligonucleotide for amplifying a part of the nucleotide sequence of the fadB gene, primer fadB_F7

<400> SEQUENCE: 27
cgactacggt agcgttagca gaa                                    23

<210> SEQ ID NO 28
<211> LENGTH: 23
<212> TYPE: DNA
<213> ORGANISM: Artificial Sequence
<220> FEATURE:
<223> OTHER INFORMATION: Oligonucleotide for amplifying a part of the nucleotide sequence of the fadB gene, primer fadB_R7

<400> SEQUENCE: 28
catcaagtaa gcaggaccca ttg                                    23

<210> SEQ ID NO 29
<211> LENGTH: 23
<212> TYPE: DNA
<213> ORGANISM: Artificial Sequence
<220> FEATURE:
<223> OTHER INFORMATION: Oligonucleotide for amplifying a part of the nucleotide sequence of the fadB gene, primer fadB_F8

<400> SEQUENCE: 29
ctttaagccg tatccgtcct acg                                    23

<210> SEQ ID NO 30
<211> LENGTH: 23
<212> TYPE: DNA
<213> ORGANISM: Artificial Sequence
<220> FEATURE:
<223> OTHER INFORMATION: Oligonucleotide for amplifying a part of the nucleotide sequence of the fadB gene, primer fadB_R8

<400> SEQUENCE: 30
ggcgctctag taccgaagct aag                                    23

<210> SEQ ID NO 31
<211> LENGTH: 23

```
<212> TYPE: DNA
<213> ORGANISM: Artificial Sequence
<220> FEATURE:
<223> OTHER INFORMATION: Oligonucleotide for amplifying a part of the
      nucleotide sequence of the fadB gene, primer fadB_F9

<400> SEQUENCE: 31
cattcaaccg ttttgaagac ctg                                          23

<210> SEQ ID NO 32
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the fadB gene, primer fadB_R9

<400> SEQUENCE: 32
gataccgatg atacgtggca aac                                          23

<210> SEQ ID NO 33
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the fadD gene, primer fadD_F1

<400> SEQUENCE: 33
cacattcccg ctttaacaga tca                                          23

<210> SEQ ID NO 34
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the fadD gene, primer fadD_R1

<400> SEQUENCE: 34
tgcgacgtta tccacttctt tgt                                          23

<210> SEQ ID NO 35
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the fadD gene, primer fadD_F2

<400> SEQUENCE: 35
cacattcccg ctttaacaga tca                                          23

<210> SEQ ID NO 36
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the fadD gene, primer fadD_R2

<400> SEQUENCE: 36
gtgcgacgtt atccacttct ttg                                          23

<210> SEQ ID NO 37
<211> LENGTH: 23
<212> TYPE: DNA
```

```
<213> ORGANISM: Artificial Sequence
<220> FEATURE:
<223> OTHER INFORMATION: Oligonucleotide for amplifying a part of the
      nucleotide sequence of the fadD gene, primer fadD_F3

<400> SEQUENCE: 37
accagcaata tggagcgagc tat                                              23

<210> SEQ ID NO 38
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the fadD gene, primer fadD_R3

<400> SEQUENCE: 38
attaggcagc atgatagcga cac                                              23

<210> SEQ ID NO 39
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the fadD gene, primer fadD_F4

<400> SEQUENCE: 39
cgccttacca aattgaccaa aag                                              23

<210> SEQ ID NO 40
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the fadD gene, primer fadD_R4

<400> SEQUENCE: 40
cggtgtattg gataaaggca aca                                              23

<210> SEQ ID NO 41
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the fadD gene, primer fadD_F5

<400> SEQUENCE: 41
cgagaattca ccagcaatat gga                                              23

<210> SEQ ID NO 42
<211> LENGTH: 23
<212> TYPE: DNA
<213> ORGANISM: Artificial Sequence
<220> FEATURE:
<223> OTHER INFORMATION: Oligonucleotide for amplifying a part of the
      nucleotide sequence of the fadD gene, primer fadD_R5

<400> SEQUENCE: 42
ttaggcagca tgatagcgac act                                              23

<210> SEQ ID NO 43
<211> LENGTH: 1492
<212> TYPE: DNA
<213> ORGANISM: Moraxella sp. KMC 4-1
```

<400> SEQUENCE: 43

```
gagtttgatc ctggctcaga ttgaacgctg gcggcaggct taacacatgc aagtcgaacg    60
atgattatct agcttgctag atatgattag tggcggacgg gtgagtaaca tttaggaatc   120
tgcctagtag tgggggatag ctcggggaaa ctcgaattaa taccgcatac gacctacggg   180
tgaaaggggg cgcaagctct tgctattaga tgagcctaaa tcagattagc tagttggtgg   240
ggtaaaggcc caccaaggcg acgatctgta actggtctga gaggatgatc agtcacaccg   300
gaactgagac acggtccgga ctcctacggg aggcagcagt ggggaatatt ggacaatggg   360
ggcaaccctg atccagccat gccgcgtgtg tgaagaaggc cttttggttg taaagcactt   420
taagcaggga ggagaggcta atggttaata cccattagat tagacgttac ctgcagaata   480
agcaccggct aactctgtgc cagcagccgc ggtaatacag agggtgcgag cgttaatcgg   540
aattactggg cgtaaagcga gtgtaggtgg ctcattaagt cacatgtgaa atccccgggc   600
ttaacctggg aactgcatgt gatactggtg gtgctagaat atgtgagagg gaagtagaat   660
tccaggtgta gcggtgaaat gcgtagagat ctggaggaat accgatggcg aaggcagctt   720
cctggcataa tattgacact gagattcgaa agcgtgggta gcaaacagga ttagataccc   780
tggtagtcca cgccgtaaac gatgtctact agccgttggg gtccttgaga ctttagtggc   840
gcagttaacg cgataagtag accgcctggg gagtacggcc gcaaggttaa aactcaaatg   900
aattgacggg ggcccgcaca gcggtggag catgtggttt aattcgatgc aacgcgaaga   960
accttacctg gtcttgacat agtgagaatc ctgcagagat gcgggagtgc cttcgggaat  1020
tcacatacag gtgctgcatg gctgtcgtca gctcgtgtcg tgagatgttg ggttaagtcc  1080
cgcaacgagc gcaacccttt tccttatttg ccagcgggtt aagccgggaa ctttaaggat  1140
actgccagtg acaaactgga ggaaggcggg gacgacgtca agtcatcatg gcccttacga  1200
ccagggctac acacgtgcta caatggtagg tacagagggt tgctacacag cgatgtgatg  1260
ctaatctcaa aaagcctatc gtagtccgga ttggagtctg caactcgact ccatgaagtc  1320
ggaatcgcta gtaatcgcag atcagaatgc tgcggtgaat acgttcccgg gccttgtaca  1380
caccgcccgt cacaccatgg gagtctattg caccagaagt aggtagccta acgmaagagg  1440
gcgcttacca cggtgtggtc gatgactggg gtgaagtcgt aacaaggtag cc           1492
```

<210> SEQ ID NO 44
<211> LENGTH: 1483
<212> TYPE: DNA
<213> ORGANISM: Moraxella osloensis ATCC19976

<400> SEQUENCE: 44

```
gagtttgatc ctggctcaga ttgaacgctg gcggcaggct taacacatgc aagtcgaacg    60
atgactctct agcttgctag agatgattag tggcggacgg gtgagtaaca tttaggaatc   120
tacctagtag tgggggatag ctcggggaaa ctcgaattaa taccgcatac gacctacggg   180
tgaaaggggg cgcaagctct tgctattaga tgagcctaaa tcagattagc tagttggtgg   240
ggtaaaggcc caccaaggcg acgatctgta actggtctga gaggatgatc agtcacaccg   300
gaactgagac acggtccgga ctcctacggg aggcagcagt ggggaatatt ggacaatggg   360
ggcaaccctg atccagccat gccgcgtgtg tgaagaaggc cttttggttg taaagcactt   420
taagcaggga ggagaggcta atggttaata cccattagat tagacgttac ctgcagaata   480
agcaccggct aactctgtgc cagcagccgc ggtaatacag agggtgcgag cgttaatcgg   540
```

```
aattactggg cgtaaagcga gtgtaggtgg ctcattaagt cacatgtgaa atccccgggc    600
ttaacctggg aactgcatgt gatactggtg gtgctagaat atgtgagagg gaagtagaat    660
tccaggtgta gcggtgaaat gcgtagagat ctggaggaat accgatggcg aaggcagctt    720
cctggcataa tattgacact gagattcgaa agcgtgggta gcaaacagga ttagataccc    780
tggtagtcca cgccgtaaac gatgtctact agccgttggg gtccttgaga ctttagtggc    840
gcagttaacg cgataagtag accgcctggg gagtacggcc gcaaggttaa aactcaaatg    900
aattgacggg ggcccgcaca agcggtggag catgtggttt aattcgatgc aacgcgaaga    960
accttacctg gtcttgacat agtgagaatc tytcagagat gagagagtgc cttcgggaac   1020
tcacatacag gtgctgcatg gctgtcgtca gctcgtgtcg tgagatgttg ggttaagtcc   1080
cgcaacgagc gcaacccttt tccttatttg ccagcgggtt aagccgggaa ctttaaggat   1140
actgccagtg acaaactgga ggaaggcggg gacgacgtca agtcatcatg gcccttacga   1200
ccagggctac acacgtgcta caatggtagg tacagagggt tgctacacag cgatgtgatg   1260
ctaatctcaa aaagcctatc gtagtccgga ttggagtctg caactcgact ccatgaagtc   1320
ggaatcgcta gtaatcgcgg atcagaatgc cgcggtgaat acgttccgg gccttgtaca   1380 caccgcccgt cacaccatgg gagtctattg caccagaagt aggtagccta acgaaagagg   1440
gcgcttacca cggtgtggtc gatgactggg gtgaagtcgt aac                   1483
```

METHOD OF EVALUATING INHIBITORY EFFECT ON DAMP-DRY MALODOR

REFERENCE TO SEQUENCE LISTING SUBMITTED ELECTRONICALLY

The content of the electronically submitted substitute sequence listing, file name 2537_1010002_SequenceListing_ST25.txt, size 40,966 bytes; and date of creation Jun. 26, 2014, filed herewith, is incorporated herein by reference in its entirety.

FIELD OF THE INVENTION

The present invention relates to a method of evaluating inhibitory effect on damp-dry malodor.

BACKGROUND OF THE INVENTION

Fabric products, for example, sanitary products (such as underclothes, towels, handkerchiefs, and bedclothes), and garments (hereinafter, in the present specification, also simply referred to as "fabric products") provide a comfortable sense of use and wear sensation when the fabric products are kept clean. Furthermore, fabric products such as garments are materials that are put on human bodies, and sanitary products such as towels and bedclothes are used by being brought into direct contact with human bodies. Therefore, it is important even from the viewpoint of hygiene to keep these fabric products clean. Along the enhanced recent social requirements for hygiene, the public interest in keeping these fabric products clean has increased.

In recent years, as consumers build up more interest in the living environment, it is desired more than ever to remove any unpleasant odors of personal belongings. The odors that cling to fabric products, for example, sanitary products and garments, include external factors such as cigarettes, as well as internal factors that are originated from human body, which are produced by repeated use of fabric products.

Since the above-described fabric products are brought into direct contact with human skin, the fabric products have a potential to absorb or attach sweat containing sebum, corneous substances and the like. For this reason, the fabric products may produce a characteristic malodor in a case where after laundry, laundered fabric products are left untouched in a damp place such as the inside of a laundering machine tub for a long time, in the case of having been dried indoors, in the case of having gotten wet with rain or sweat, or in the case of insufficiently dried fabric products. This malodor is generally called a damp-dry malodor, and this odor can be prevented from occurring by sufficiently drying the fabric products in some cases. However, even for fabric products which have been sufficiently dried and from which no damp-dry malodor is sensed, wet-and-dirty dustcloth-malodor-like damp-dry malodor may be produced when the fabric products become damp due to sweat, rain or the like. That is, if fabric products once produce this damp-dry malodor, the wet-and-dirty dustcloth-like damp-dry malodor is likely to recur at the time of use even when the damp-dry malodor can be temporarily eliminated by laundry. Such a damp-dry malodor that is prone to recur may be produced not only in a case where fabric products are dried indoors, but also in a case where a dryer or a washing machine having a low temperature drying function is used, and even in the case of fabric products that have been dried outdoors, if the fabric products become damp.

A feature of the recurrent damp-dry malodor lies in that the fabric product produces the malodor only by becoming damp. The recurrent damp-dry malodor is produced in some cases when fabric products are stored in a wardrobe or the like for a long time. Fabric products (such as underclothes, handkerchiefs or towels), which are frequently brought into contact with human skin and are used with a high use frequency and a short period of the wash-use cycle, are in many cases such that once this damp-dry malodor is produced, the malodor comes to recur during use. In order to inhibit this damp-dry malodor, it is important to treat fabric products so as not to produce such damp-dry malodor-causing substances. As a method for that purpose, there is a demand for a base material or a material which inhibits the damp-dry malodor. Also, there is a demand for the development of a method of evaluating inhibitory effect on damp-dry malodor for screening a damp-dry malodor inhibitor.

It has been hitherto reported that the damp-dry malodor is a complex odor composed of the "mold-like malodor" of medium-chain aldehydes, medium-chain alcohols, ketones and the like, the "sour malodor" of short-chain fatty acids, medium-chain fatty acids and the like, the "fishy malodor" of nitrogen compounds, and sulfur compounds (see Patent Literature 1). Patent Literature 1 also reports that the medium-chain fatty acids in particular have a high degree of contribution, and that a major component of the damp-dry malodor is speculated to be "a mixture of unsaturated fatty acids having a branched structure with 7 to 9 carbon atoms," which are also contained in the foul odor of human sweat or the like. Further, as indicator substances for the damp-dry malodor, various kinds of fatty acids including 4-methyl-3-hexenoic acid have been hitherto suggested (see Patent Literature 1). The 4-methyl-3-hexenoic acid is naturally known as a component of citrons (see Non-Patent Literature 2), and it is also known that the 4-methyl-3-hexenoic acid is produced from terpenes by microorganisms (see Patent Literature 2). However, these literatures do not describe or suggest the mechanism of the production of the damp-dry malodor. Furthermore, there is no instance of devising a method of evaluating inhibitory effect on damp-dry malodor and a method of screening a damp-dry malodor inhibitor based on such a mechanism.

PRIOR ART LITERATURE

Patent Literatures

Patent Literature 1: JP-A-2009-244094 ("JP-A" means unexamined published Japanese patent application)
Patent Literature 2: JP-A-56-124387

Non-Patent Literatures

Non-Patent Literature 1: Hanihara, Sonoda, "The Detergent Curbing Malodor in Indoor Laundry Drying," Fragrances, September 2004, No. 223, p. 109-116
Non-Patent Literature 2: Proceedings of the 53$^{rd}$ Forum on Fragrances/Terpenes, and Oil Refinery Chemistry (2009), p. 4-6

SUMMARY OF THE INVENTION

The present invention relates to a method of evaluating inhibitory effect on damp-dry malodor, containing the steps of: bringing microorganisms which produce damp-dry malodor-causing substances and a test substance into contact with each other in the presence of a sebaceous dirt component; detecting expression of at least one kind of gene selected from a fatty acid desaturase gene and a β oxidation-related enzyme gene derived from the microorganisms; and thereby evaluating a damp-dry malodor inhibitory function of the test substance based on a change in expression amount of the at least one kind of gene;

wherein the expression of the at least one kind of gene is detected by using at least one kind of oligonucleotide pair selected from an oligonucleotide pair containing oligonucleotides (a) and (b) described below, an oligonucleotide pair containing oligonucleotides (c) and (d) described below, an oligonucleotide pair containing oligonucleotides (e) and (f) described below, an oligonucleotide pair containing oligonucleotides (g) and (h) described below, an oligonucleotide pair containing oligonucleotides (i) and (j) described below, an oligonucleotide pair containing oligonucleotides (k) and (l) described below, an oligonucleotide pair containing oligonucleotides (m) and (n) described below, an oligonucleotide pair containing oligonucleotides (o) and (p) described below, an oligonucleotide pair containing oligonucleotides (q) and (r) described below, an oligonucleotide pair containing oligonucleotides (s) and (t) described below, an oligonucleotide pair containing oligonucleotides (u) and (v) described below, an oligonucleotide pair containing oligonucleotides (w) and (x) described below, an oligonucleotide pair containing oligonucleotides (y) and (z) described below, an oligonucleotide pair containing oligonucleotides (a1) and (b1) described below, and an oligonucleotide pair containing oligonucleotides (c1) and (d1) described below:

(a) an oligonucleotide having the base sequence set forth in SEQ ID NO: 13, an oligonucleotide having a base sequence set forth in SEQ ID NO: 13 with a substitution, deletion, insertion, or addition of 1 or several nucleotides which can be used for detecting the fatty acid desaturase gene;

(b) an oligonucleotide having the base sequence set forth in SEQ ID NO: 14, an oligonucleotide having a base sequence set forth in SEQ ID NO: 14 with a substitution, deletion, insertion, or addition of 1 or several nucleotides which can be used for detecting the fatty acid desaturase gene;

(c) an oligonucleotide having the base sequence set forth in SEQ ID NO: 15, an oligonucleotide having a base sequence set forth in SEQ ID NO: 15 with a substitution, deletion, insertion, or addition of 1 or several nucleotides which can be used for detecting the fatty acid desaturase gene;

(d) an oligonucleotide having the base sequence set forth in SEQ ID NO: 16, an oligonucleotide having a base sequence set forth in SEQ ID NO: 16 with a substitution, deletion, insertion, or addition of 1 or several nucleotides which can be used for detecting the fatty acid desaturase gene;

(e) an oligonucleotide having the base sequence set forth in SEQ ID NO: 17, an oligonucleotide having a base sequence set forth in SEQ ID NO: 17 with a substitution, deletion, insertion, or addition of 1 or several nucleotides which can be used for detecting the fatty acid desaturase gene;

(f) an oligonucleotide having the base sequence set forth in SEQ ID NO: 18, an oligonucleotide having a base sequence set forth in SEQ ID NO: 18 with a substitution, deletion, insertion, or addition of 1 or several nucleotides which can be used for detecting the fatty acid desaturase gene;

(g) an oligonucleotide having the base sequence set forth in SEQ ID NO: 19, an oligonucleotide having a base sequence set forth in SEQ ID NO: 19 with a substitution, deletion, insertion, or addition of 1 or several nucleotides which can be used for detecting the fatty acid desaturase gene;

(h) an oligonucleotide having the base sequence set forth in SEQ ID NO: 20, an oligonucleotide having a base sequence set forth in SEQ ID NO: 20 with a substitution, deletion, insertion, or addition of 1 or several nucleotides which can be used for detecting the fatty acid desaturase gene;

(i) an oligonucleotide having the base sequence set forth in SEQ ID NO: 21, an oligonucleotide having a base sequence set forth in SEQ ID NO: 21 with a substitution, deletion, insertion, or addition of 1 or several nucleotides which can be used for detecting the fatty acid desaturase gene;

(j) an oligonucleotide having the base sequence set forth in SEQ ID NO: 22, an oligonucleotide having a base sequence set forth in SEQ ID NO: 22 with a substitution, deletion, insertion, or addition of 1 or several nucleotides which can be used for detecting the fatty acid desaturase gene;

(k) an oligonucleotide having the base sequence set forth in SEQ ID NO: 23, an oligonucleotide having a base sequence set forth in SEQ ID NO: 23 with a substitution, deletion, insertion, or addition of 1 or several nucleotides which can be used for detecting the fatty acid desaturase gene;

(l) an oligonucleotide having the base sequence set forth in SEQ ID NO: 24, an oligonucleotide having a base sequence set forth in SEQ ID NO: 24 with a substitution, deletion, insertion, or addition of 1 or several nucleotides which can be used for detecting the fatty acid desaturase gene;

(m) an oligonucleotide having the base sequence set forth in SEQ ID NO: 25, an oligonucleotide having a base sequence set forth in SEQ ID NO: 25 with a substitution, deletion, insertion, or addition of 1 or several nucleotides which can be used for detecting the β oxidation-related enzyme gene;

(n) an oligonucleotide having the base sequence set forth in SEQ ID NO: 26, an oligonucleotide having a base sequence set forth in SEQ ID NO: 26 with a substitution, deletion, insertion, or addition of 1 or several nucleotides which can be used for detecting the β oxidation-related enzyme gene;

(o) an oligonucleotide having the base sequence set forth in SEQ ID NO: 27, an oligonucleotide having a base sequence set forth in SEQ ID NO: 27 with a substitution, deletion, insertion, or addition of 1 or several nucleotides which can be used for detecting the β oxidation-related enzyme gene;

(p) an oligonucleotide having the base sequence set forth in SEQ ID NO: 28, an oligonucleotide having a base sequence set forth in SEQ ID NO: 28 with a substitution, deletion, insertion, or addition of 1 or several nucleotides which can be used for detecting the β oxidation-related enzyme gene;

(q) an oligonucleotide having the base sequence set forth in SEQ ID NO: 29, an oligonucleotide having a base sequence set forth in SEQ ID NO: 29 with a substitution, deletion, insertion, or addition of 1 or several nucleotides which can be used for detecting the β oxidation-related enzyme gene;

(r) an oligonucleotide having the base sequence set forth in SEQ ID NO: 30, an oligonucleotide having a base sequence set forth in SEQ ID NO: 30 with a substitution, deletion, insertion, or addition of 1 or several nucleotides which can be used for detecting the β oxidation-related enzyme gene;

(s) an oligonucleotide having the base sequence set forth in SEQ ID NO: 31, an oligonucleotide having a base sequence set forth in SEQ ID NO: 31 with a substitution, deletion, insertion, or addition of 1 or several nucleotides which can be used for detecting the β oxidation-related enzyme gene;

(t) an oligonucleotide having the base sequence set forth in SEQ ID NO: 32, an oligonucleotide having a base sequence set forth in SEQ ID NO: 32 with a substitution, deletion, insertion, or addition of 1 or several nucleotides which can be used for detecting the β oxidation-related enzyme gene;

(u) an oligonucleotide having the base sequence set forth in SEQ ID NO: 33, an oligonucleotide having a base sequence set forth in SEQ ID NO: 33 with a substitution, deletion, insertion, or addition of 1 or several nucleotides which can be used for detecting the β oxidation-related enzyme gene;
(v) an oligonucleotide having the base sequence set forth in SEQ ID NO: 34, an oligonucleotide having a base sequence set forth in SEQ ID NO: 34 with a substitution, deletion, insertion, or addition of 1 or several nucleotides which can be used for detecting the β oxidation-related enzyme gene;
(w) an oligonucleotide having the base sequence set forth in SEQ ID NO: 35, an oligonucleotide having a base sequence set forth in SEQ ID NO: 35 with a substitution, deletion, insertion, or addition of 1 or several nucleotides which can be used for detecting the β oxidation-related enzyme gene;
(x) an oligonucleotide having the base sequence set forth in SEQ ID NO: 36, an oligonucleotide having a base sequence set forth in SEQ ID NO: 36 with a substitution, deletion, insertion, or addition of 1 or several nucleotides which can be used for detecting the β oxidation-related enzyme gene;
(y) an oligonucleotide having the base sequence set forth in SEQ ID NO: 37, an oligonucleotide having a base sequence set forth in SEQ ID NO: 37 with a substitution, deletion, insertion, or addition of 1 or several nucleotides which can be used for detecting the β oxidation-related enzyme gene;
(z) an oligonucleotide having the base sequence set forth in SEQ ID NO: 38, an oligonucleotide having a base sequence set forth in SEQ ID NO: 38 with a substitution, deletion, insertion, or addition of 1 or several nucleotides which can be used for detecting the β oxidation-related enzyme gene;
(a1) an oligonucleotide having the base sequence set forth in SEQ ID NO: 39, an oligonucleotide having a base sequence set forth in SEQ ID NO: 39 with a substitution, deletion, insertion, or addition of 1 or several nucleotides which can be used for detecting the β oxidation-related enzyme gene;
(b1) an oligonucleotide having the base sequence set forth in SEQ ID NO: 40, an oligonucleotide having a base sequence set forth in SEQ ID NO: 40 with a substitution, deletion, insertion, or addition of 1 or several nucleotides which can be used for detecting the β oxidation-related enzyme gene;
(c1) an oligonucleotide having the base sequence set forth in SEQ ID NO: 41, an oligonucleotide having a base sequence set forth in SEQ ID NO: 41 with a substitution, deletion, insertion, or addition of 1 or several nucleotides which can be used for detecting the β oxidation-related enzyme gene; and
(d1) an oligonucleotide having the base sequence set forth in SEQ ID NO: 42, an oligonucleotide having a base sequence set forth in SEQ ID NO: 42 with a substitution, deletion, insertion, or addition of 1 or several nucleotides which can be used for detecting the β oxidation-related enzyme gene.

Further, the present invention relates to a method of screening a damp-dry malodor inhibitor, which contains selecting a test substance capable of reducing the expression amount of the at least one kind of gene described above based on the evaluation method described above.

Further, the present invention relates to a method of detecting microorganisms which produce damp-dry malodor-causing substances, containing the steps of: amplifying at least one kind of fragment of gene selected from a fatty acid desaturase gene and a β oxidation-related enzyme gene that are derived from microorganisms which produce damp-dry malodor-causing substances; determining the presence or absence of an amplified fragment; and thereby detecting the microorganisms which produce damp-dry malodor-causing substances,
wherein the detection of the microorganisms which produce damp-dry malodor-causing substances is performed by using at least one kind of oligonucleotide pair selected from an oligonucleotide pair containing the oligonucleotides (a) and (b) described above, an oligonucleotide pair containing the oligonucleotides (c) and (d) described above, an oligonucleotide pair containing the oligonucleotides (e) and (f) described above, an oligonucleotide pair containing the oligonucleotides (g) and (h) described above, an oligonucleotide pair containing the oligonucleotides (i) and (j) described above, an oligonucleotide pair containing the oligonucleotides (k) and (l) described above, an oligonucleotide pair containing the oligonucleotides (m) and (n) described above, an oligonucleotide pair containing the oligonucleotides (o) and (p) described above, an oligonucleotide pair containing the oligonucleotides (q) and (r) described above, an oligonucleotide pair containing the oligonucleotides (s) and (t) described above, an oligonucleotide pair containing the oligonucleotides (u) and (v) described above, an oligonucleotide pair containing the oligonucleotides (w) and (x) described above, an oligonucleotide pair containing the oligonucleotides (y) and (z) described above, an oligonucleotide pair containing the oligonucleotides (a1) and (b1) described above, and an oligonucleotide pair containing the oligonucleotides (c1) and (d1) described above.

Further, the present invention relates to an oligonucleotide selected from the above-described oligonucleotides (a) to (z) and (a1) to (d1); or an oligonucleotide pair selected from a pair of the above-described oligonucleotides (a) and (b), a pair of the above-described oligonucleotides (c) and (d), a pair of the above-described oligonucleotides (e) and (f), a pair of the above-described oligonucleotides (g) and (h), a pair of the above-described oligonucleotides (i) and (j), a pair of the above-described oligonucleotides (k) and (l), a pair of the above-described oligonucleotides (m) and (n), a pair of the above-described oligonucleotides (o) and (p), a pair of the above-described oligonucleotides (q) and (r), a pair of the above-described oligonucleotides (s) and (t), a pair of the above-described oligonucleotides (u) and (v), a pair of the above-described oligonucleotides (w) and (x), a pair of the above-described oligonucleotides (y) and (z), a pair of the above-described oligonucleotides (a1) and (b1), and a pair of the above-described oligonucleotides (c1) and (d1).

Further, the present invention relates to a kit for evaluating inhibitory effect on damp-dry malodor or a kit for screening of a damp-dry malodor inhibitor, containing microorganisms which produce damp-dry malodor-causing substances, a sebaceous dirt component, and the oligonucleotide or oligonucleotide pair described above.

Further, the present invention relates to a kit for detecting microorganisms which produce damp-dry malodor-causing substances, containing the oligonucleotide or oligonucleotide pair described above.

DETAILED DESCRIPTION OF THE INVENTION

The present invention resides in to provide a method of evaluating inhibitory effect on damp-dry malodor, by which the damp-dry malodor inhibitory function of a test substance can be evaluated conveniently with high accuracy. Further, the present invention resides in to provide a method of screening a damp-dry malodor inhibitor, by which a damp-dry malodor inhibitor can be screened conveniently with high accuracy. Further, the present invention resides in to provide a method of detecting microorganisms which produce damp-dry malodor-causing substances, by which microorganisms which produce damp-dry malodor-causing substances present in an environment can be detected quickly with high accuracy. Further, the present invention resides in to provide an oligonucleotide or oligonucleotide pair, which can be preferably used in the evaluating method, the screening method and the detection method described above.

In view of the points described above, the inventors of the present invention conducted a thorough investigation from the viewpoints of the causative substances of the damp-dry malodor, causative bacteria generating damp-dry malodor-causing substances, and the mechanism of occurrence of the damp-dry malodor. As a result, it was found that fatty acid desaturase or β oxidation-related enzymes of microorganisms which produce damp-dry malodor-causing substances are related to production of 4-methyl-3-hexenoic acid as one kind of damp-dry malodor-causing substance. It was also found that evaluation of inhibitory effect on damp-dry malodor and screening of a damp-dry malodor inhibitor can be achieved, by analyzing a change in expression amount of the genes of those enzymes in the presence of a test substance. It was also found that microorganisms which produce damp-dry malodor-causing substances present in an environment including towels and clothes can be detected by using a pair of oligonucleotides designed based on base sequence of the gene of a fatty acid desaturase or β oxidation-related enzymes of specific microorganisms which produce damp-dry malodor-causing substances.

The present invention has been completed based on the findings.

The fatty acid desaturase and the β oxidation-related enzyme derived from microorganisms which produce damp-dry malodor-causing substances are related to production of the medium-chain branched fatty acids including mainly 4-methyl-3-hexenoic acid as a damp-dry malodor-causing substance. Moreover, it is now possible to amplify a part of each gene of the fatty acid desaturase or the β oxidation-related enzyme by using the oligonucleotide pair described above.

Therefore, according to the method of evaluating inhibitory effect on damp-dry malodor using the above-described oligonucleotide pair of the present invention, the damp-dry malodor inhibitory function of a test substance can be evaluated conveniently with high accuracy. Furthermore, according to the method of screening a damp-dry malodor inhibitor of the present invention utilizing the evaluating method described above, a damp-dry malodor inhibitor can be screened conveniently with high accuracy. Moreover, according to the method of the present invention to detect microorganisms which produce damp-dry malodor-causing substances by using the oligonucleotide pair described above, the microorganisms which produce damp-dry malodor-causing substances present in an environment can be detected quickly and accurately. Moreover, the oligonucleotide or oligonucleotide pair of the present invention can be preferably used for the evaluation method, the screening method and the detection method described above.

Other and further features and advantages of the invention will appear more fully from the following description.

The method of evaluating inhibitory effect on damp-dry malodor of the present invention contains the steps of: bringing microorganisms which produce damp-dry malodor-causing substances and a test substance into contact with each other in the presence of a sebaceous dirt component; detecting expression of at least one kind of gene selected from a fatty acid desaturase gene and a β oxidation-related enzyme gene derived from the microorganisms; and thereby evaluating a damp-dry malodor inhibitory function of the test substance based on a change in expression amount of the at least one kind of gene. Herein, the expression of the at least one kind of gene is detected by using at least one kind of oligonucleotide pair selected from an oligonucleotide pair containing the above-described oligonucleotides (a) and (b), an oligonucleotide pair containing the above-described oligonucleotides (c) and (d), an oligonucleotide pair containing the above-described oligonucleotides (e) and (f), an oligonucleotide pair containing the above-described oligonucleotides (g) and (h), an oligonucleotide pair containing the above-described oligonucleotides (i) and (j), an oligonucleotide pair containing the above-described oligonucleotides (k) and (l), an oligonucleotide pair containing the above-described oligonucleotides (m) and (n), an oligonucleotide pair containing the above-described oligonucleotides (o) and (p), an oligonucleotide pair containing the above-described oligonucleotides (q) and (r), an oligonucleotide pair containing the above-described oligonucleotides (s) and (t), an oligonucleotide pair containing the above-described oligonucleotides (u) and (v), an oligonucleotide pair containing the above-described oligonucleotides (w) and (x), an oligonucleotide pair containing the above-described oligonucleotides (y) and (z), an oligonucleotide pair containing the above-described oligonucleotides (a1) and (b1), and an oligonucleotide pair containing the above-described oligonucleotides (c1) and (d1). According to the method of evaluating inhibitory effect on damp-dry malodor of the present invention, for example, as for a substance that has been selected as a candidate for a damp-dry malodor inhibitor, a high accuracy evaluation of the damp-dry malodor inhibitory function of the substance can be conveniently carried out.

Moreover, the method of screening a damp-dry malodor inhibitor of the present invention contains selecting a test substance capable of reducing the expression amount of the at least one kind of gene described above based on the evaluation method described above. According to the method of screening a damp-dry malodor inhibitor of the present invention, it is possible to simply perform screening of a damp-dry malodor inhibitor with high accuracy without depending on a means such as sterilization of causative microorganisms.

In the present specification, the term "damp-dry malodor-causing substances" means medium-chain branched fatty acids that are described in Patent Literature 1 as an indicator substance of the damp-dry malodor. Examples thereof include 4-methyl-3-hexanoic acid, 4-methyl-3-hexenoic acid, 5-methyl-2-hexanoic acid, and 5-methyl-2-hexenoic acid. Of those, it particularly means the 4-methyl-3-hexenoic acid (in the present specification, it is also referred to as "4M3H").

In the present specification, the term "microorganisms which produce damp-dry malodor-causing substances" includes any microorganisms of the following (1) to (3).

(1) Microorganisms which can produce an intermediate from a substrate, during a process of producing damp-dry malodor-causing substances like 4M3H from a precursor (in the specification, it is also referred to as a "substrate") of the damp-dry malodor-causing substances [for example, microorganisms relating only to desaturation of sebaceous dirt components]

(2) Microorganisms which can produce damp-dry malodor-causing substances like 4M3H from an intermediate [for example, microorganisms relating only to β oxidation of unsaturated fatty acids]

(3) Microorganisms which can produce damp-dry malodor-causing substances like 4M3H from a substrate via an intermediate [for example, microorganisms relating to the desaturation of sebaceous dirt components and the β oxidation of unsaturated fatty acids]

In the present specification, the term "damp-dry malodor" means odor generated from a fabric product when a fabric product after use is washed and under drying or remains in insufficiently dry state even after drying, or a fabric product contains moisture. Even in a case in which damp-dry malodor is not felt temporarily by sufficient drying of the fabric product, wet- and dirty dustcloth-malodor-like damp-dry malodor may recur from the fabric product due to rain, sweat, moisture in the air, or the like, if the fabric product is used again right after drying or after storage. Further, even in a case in which the damp-dry malodor is not felt temporarily by sufficient drying of a fabric product, damp-dry malodor may recur during storage due to moisture in the air. As such, the wet-and-dirty dustcloth-malodor-like damp-dry malodor that recurs when a fabric product from which a damp-dry malodor has been temporarily eliminated by sufficient drying becomes damp, is also included in "damp-dry malodor" in the present specification.

The damp-dry malodor that is produced because of insufficient drying after laundering of a fabric product even during drying or after drying, is a complex odor of a S (sulfur) odor, a N (nitrogen) odor, an aldehyde odor, a lower fatty acid odor, wet-and-dirty dustcloth-malodor-like malodor, and a medium-chain branched fatty acid odor containing the 4M3H odor as a main component. Meanwhile, for the fabric products which give no feeling of damp-dry malodor by sufficient drying, the wet-and-dirty dustcloth-malodor-like damp-dry malodor which recurs from the fabric product due to rain, sweat, moisture in the air or the like is mostly odor derived from the medium-chain branched fatty acids mainly containing 4M3H odor. To the contrary, other highly volatile malodor such as the S odor, the N odor and the aldehyde odor is hardly produced.

Furthermore, the term "inhibitory effect on damp-dry malodor" includes inhibitory effect of something on malodor, prevention of the production of a damp-dry malodor, and the prevention of the production of damp-dry malodor-causing substances. In the present invention, the term is defined to characteristically refer to the inhibitory effect on the wet-and-dirty dustcloth-malodor-like damp-dry malodor, particularly the 4M3H odor, as the damp-dry malodor. Further, in the present specification, the term "inhibitory effect on damp-dry malodor" means, as the prevention of the production of damp-dry malodor-causing substances, includes any one of the following (1) to (3).

(1) Prevention of production of an intermediate from a precursor of damp-dry malodor-causing substances [for example, prevention of desaturation of sebaceous dirt components]

(2) Prevention of production of damp-dry malodor-causing substances like 4M3H from an intermediate [for example, prevention of β oxidation of unsaturated fatty acids]

(3) Prevention of production of damp-dry malodor-causing substances like 4M3H from a substrate [for example, prevention of desaturation of sebaceous dirt components and β oxidation of unsaturated fatty acids]

Meanwhile, "4M3H" has cis- and trans-isomers as described below. In the present invention, the compound is intended to include compounds of both the cis-structure and the trans-structure.

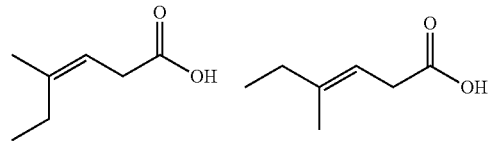

The "microorganisms which produce damp-dry malodor-causing substances" in the present invention includes the microbial cells themselves of microorganisms which produce damp-dry malodor-causing substances, as well as crushed cells, a microbial cell culture fluid, a crude extract originating from microorganisms which produce damp-dry malodor-causing substances, and a processed product of microbial cells, such as a purified enzyme.

A method of obtaining microorganisms which produce damp-dry malodor-causing substances that is used in the present invention will be described. Any methods of obtaining microorganisms which produce damp-dry malodor causing substances may be used, but examples thereof include methods (1) to (4) described below.

(1) A method of performing a sensory evaluation of fabric products, and consequently isolating a microbial strain from a fabric product that emits a damp-dry malodor.

(2) A method of isolating microorganisms that exist in a fabric product, measuring the production capacity of damp-dry malodor-causing substances, such as 4M3H, of the isolated microorganisms, and selecting a microbial strain which produce damp-dry malodor-causing substances.

(3) A method of measuring the production capacity of damp-dry malodor-causing substances, such as 4M3H, of microorganisms that have been isolated from the environment or acquired from a microorganism depository, and selecting a microbial strain which produce damp-dry malodor-causing substances.

(4) A method of comparing the sequence similarity of a particular gene sequence with the gene sequence of a microbial strain which produce damp-dry malodor-causing substances, and selecting a microbial strain having higher sequence similarity.

Microorganisms which produce damp-dry malodor-causing substances may be selected by any one method among the methods described above, or microorganisms which produce damp-dry malodor-causing substances may be also selected by combining two, or more of the methods.

Further, a method of detecting microorganisms which produce damp-dry malodor-causing substances such as 4M3H in which 4M3H or the like is specified as damp-dry malodor-causing substances, is described in JP-A-2011-254807. The present invention may refer to the descriptions of the publication.

The method of obtaining microorganisms which produce damp-dry malodor-causing substances to be used in the present invention will be specifically described. However, the present invention is not intended to be limited to these.

First, the outline of the method (1) (a method of performing a sensory evaluation of fabric products, and isolating a microbial strain from a fabric product that emits a damp-dry malodor) will be explained.

At home or the like, fabric products (for example, towels, T-shirts, pillow covers, and underclothes) that have been used after being laundered, or stored after being laundered (unused after being laundered) are collected, and fabric products from which a strong damp-dry malodor can be perceived by a sensory evaluation are selected. The selected fabric products are cut out to a certain size (for example, 5×5 cm, 2×2 cm). The cut fabric products are added to a lecithin polysorbate (also referred to as LP in the present specification) dilution (manufactured by Nihon Pharmaceutical Co., Ltd.), physiological saline or the like. Subsequently, an extract liquid obtained by stirring is plated on an agar medium such as a lecithin polysorbate-added soybean casein digest (also referred to as SCD-LP in the present specification) agar medium (manufactured by Nihon Pharmaceutical Co., Ltd.) or a potato dextrose agar (also referred to as PDA in the present specification) medium (manufactured by Becton Dickinson Co.), and cultured for a certain time (for example, 35° C., 24 hours). After the cultivation, microorganisms are isolated from the colonies thus obtained.

The various microbial strains thus isolated are inoculated and cultured on a fabric product that has been used and sterilized, for example, a fabric product obtained by cutting a towel or the like which has been recognized for the production of a damp-dry malodor, to a certain size (for example, 5×5 cm, 2×2 cm) and sterilizing the cut pieces, and then microbial strains producing damp-dry malodor are selected by a sensory evaluation. Alternatively, the isolated microbial strains are subjected to solid culture or liquid culture in the presence of a sebaceous dirt component, and then microbial strains producing damp-dry malodor are selected by a sensory evaluation. In the case where identification of the various microbial strains that have been selected is required, there are no limitations on the identification method. However, the identification can be carried out by determining a base sequence having a length of about 500 bp in the upstream region of 16S rRNA gene in a bacterium, and a base sequence having a length of about 200 bp or more and about 500 bp or less in the D2 region of LSU (Large Subunit) in a fungus; and analyzing the sequence similarity of the base sequence with the corresponding base sequence of a reference strain. Meanwhile, the sequence similarity of base sequences may be also calculated by using a genetic information processing software, Clustal W (http://clustalw.ddbj.nig.ac.jp/top-j.html), or the like.

Next, the outline of the method (2) (a method of isolating microorganisms that exist in a fabric product, measuring the production capacity of damp-dry malodor-causing substances, such as 4M3H, of the isolated microorganisms, and selecting a microbial strain which produce damp-dry malodor-causing substances) will be explained.

At home or the like, fabric products (for example, towels, T-shirts, pillow covers and underclothes) that have been used after being laundered, or stored after being laundered (unused after being laundered) are collected and cut out to a certain size (for example, 5×5 cm, 2×2 cm). The cut fabric products are added to a LP dilution (manufactured by Nihon Pharmaceutical Co., Ltd.), physiological saline or the like. Subsequently, an extract liquid obtained by stirring is plated on an agar medium such as a SCD-LP agar medium (manufactured by Nihon Pharmaceutical Co., Ltd.) or a PDA medium (manufactured by Becton Dickinson Co.), and cultured for a certain time (for example, 35° C., 24 hours), and then microorganisms are isolated from the colonies thus obtained.

The various microbial strains thus isolated are inoculated and cultured on a fabric product that has been used and sterilized, for example, a fabric product obtained by cutting a towel or the like which has been recognized for the production of a damp-dry malodor, to a certain size (for example, 5×5 cm, 2×2 cm) and sterilizing the cut pieces, and then microbial strains producing damp-dry malodor are selected by a sensory evaluation. Alternatively, the isolated microbial strains are subjected to solid culture or liquid culture in the presence of a sebaceous dirt component and then sensory evaluation is carried out, and thereby microbial strains which are recognized to produce damp-dry malodor are selected. In the case where identification of the various microbial strains that have been selected is required, there are no limitations on the identification method. However, for example, the identification can be carried out by determining a base sequence having a length of about 500 bp in the upstream region of 16S rRNA gene in a bacterium, and a base sequence having a length of about 200 bp or more and about 500 bp or less in the D2 region of LSU in a fungus; and analyzing the sequence similarity of the base sequence with the corresponding base sequence of a reference strain. Meanwhile, the sequence similarity of base sequences may be also calculated by using a genetic information processing software, Clustal W, or the like.

Next, the method (3) (a method of measuring the production capacity of damp-dry malodor-causing substances of microorganisms that have been isolated from the environment or acquired from a microorganism depository, and selecting a microbial strain which produce damp-dry malodor-causing substances) will be explained.

Microbial strains are purchased from institutions for microorganism distribution such as ATCC (American Type Culture Collection), NBRC (NITE Biological Resource Center), JCM (Japan Collection of Microorganisms), and NCIMB (National Collection of Industrial Marine and Food Bacteria). Alternatively, microbial strains are isolated using a SCD-LP agar medium (manufactured by Nihon Pharmaceutical Co., Ltd.), a PDA medium (manufactured by Becton Dickinson Co.) or the like by a routine method from various environments such as soils, plants, river water, and inside dwellings; and then microbial strains are isolated. Meanwhile, any medium can be used herein.

The various microbial strains that have been purchased or isolated are inoculated and cultured on a fabric product that has been used and sterilized, for example, a fabric product obtained by cutting a towel or the like which has been recognized for the production of a damp-dry malodor, to a certain size (for example, 5×5 cm, 2×2 cm) and sterilizing the cut pieces. Then, production of damp-dry malodor-causing substances, such as 4M3H, is detected, and thereby microbial strains which are recognized to produce damp-dry malodor-causing substances are selected. Alternatively, the purchased or isolated microbial strains are subjected to solid culture or liquid culture in the presence of a sebaceous dirt component. Subsequently, production of damp-dry malodor-causing substances is detected, and thereby microbial strains which are recognized to produce damp-dry malodor-causing substances, such as 4M3H, are selected. In the case where identification is required to the various microbial strains that have been selected from the microorganisms isolated from the environment, there are no limitations on the identification method. For example, identification can be carried out by determining a base sequence having a length of about 500 bp in the upstream region of 16S rRNA gene in a bacterium, and a base sequence having a length of about 200 bp or more and about 500 bp or less in the D2 region of LSU in a fungus; and analyzing the sequence similarity of the base sequence with the corresponding base sequence of a reference strain. Meanwhile, the sequence similarity of base sequences may be also calculated by using a genetic information processing software, Clustal W, or the like.

Next, the outline of the method (4) (a method of comparing the sequence similarity of a particular gene sequence with the gene sequence of a microbial strain which produce damp-dry malodor-causing substances, such as 4M3H, and selecting a microbial strain having higher sequence similarity) will be explained.

First, the base sequence of a particular gene of the microbial strain which produce damp-dry malodor-causing substances, such as 4M3H, that has been selected by the method (1), method (2), and/or method (3) as described above, is determined. Then, microorganisms having a base sequence having high sequence similarity with the base sequence thus determined are selected, and thereby a microbial strain which produce damp-dry malodor-causing substances, such as 4M3H, to be used in the present invention can be obtained. For example, since *Moraxella* sp. 4-1 is one kind of causative bacteria of a damp-dry malodor, it can be selected as reference microbial strains. Next, the base sequence of the 16S rRNA gene or the like of the reference samples is determined. Then, a microbial strain having a base sequence having high sequence similarity with the entirety or a portion of the base sequence of the reference samples thus determined is selected. Here, the term "having high sequence similarity" implies that the sequence similarity with the base sequence of a reference sample is preferably 95% or more, more preferably 97% or more, further preferably 98% or more, and particularly preferably 99% or more.

The base sequence of microorganisms can be determined by an ordinary method. Furthermore, the sequence similarity of a base sequence is calculated by the Lipman-Pearson method (Science, 227, p. 1435 (1985)) or the like. Specifically, the sequence similarity of a base sequence can be calculated by using a sequence similarity analysis (Search Homology) program of a genetic information processing software, Genetyx-Win (manufactured by Software Development, Inc.), and carrying out an analysis by taking the Unit size to compare (ktup) parameter as 2.

The microorganisms that are used in the present invention may be microorganisms which produce damp-dry malodor-causing substances, such as 4M3H, in the presence of a sebaceous component. For example, the microorganisms are preferably the genus *Moraxella*, and particularly preferably at least one kind of microbial strain selected from the species of *Moraxella* sp. and *Moraxella osloensis*.

Meanwhile, in the present invention, "*Moraxella* sp." means a microbial species having a base sequence in which the base sequence of 16S rRNA gene has a sequence similarity of 95% or more, more preferably 97% or more, further preferably 98% or more, further preferably 99% or more, and particularly preferably 99.2% or more, with the base sequence set forth in SEQ ID NO: 43 or 44. Alternatively, it means microorganisms which have 16S rRNA gene having a base sequence set forth in SEQ ID NO: 43 or 44 with a deletion, substitution, insertion, or addition of 1 to 75 bases, preferably 1 to 45 bases, more preferably 1 to 30 bases, and most preferably 1 to 15 bases. Herein, the base sequence set forth in SEQ ID NO: 43 represents a base sequence of the 16S rRNA gene of *Moraxella* sp. KMC4-1. Further, the base sequence set forth in SEQ ID NO: 44 represents a base sequence of the 16S rRNA gene of *Moraxella osloensis* ATCC19976.

Regarding the test substance that is used in the evaluation method and the screening method of the present invention, any substance may be used, and the test substance may be any of a low molecular weight compound and a high molecular weight compound. Specific examples of the test substance include, for example, inorganic salts, surfactants, proteins, antibodies, peptides, polypeptides, oligonucleotides, polynucleotides, DNAs, RNAs, lipids, sugars, polysaccharides, natural extracts, and combinations thereof. Further, the test substance described above also includes fiber product (textile product) obtained by treating (e.g. adsorption, coating, or kneading) with a substance (e.g. the above-described examples of the test substance) of which inhibitory effect on damp-dry malodor can be expected; fibers or a fabric obtained by weaving the fibers, which can inhibit the production of a damp-dry malodor by inhibiting metabolism of microorganisms which produce damp-dry malodor-causing substances through having extremely fine fibers, having different shape of fiber cross section, providing a groove on later surface of a fiber, or a research for method of weaving; and the like.

In the method of evaluating inhibitory effect on damp-dry malodor and the method of screening a damp-dry malodor inhibitor of the present invention, the microorganisms which produce damp-dry malodor-causing substances as described above are brought into contact with a test substance in the presence of a sebaceous dirt component, and the microorganisms are incubated together with the test substance and the sebaceous dirt component. In the present invention, any incubation conditions may be used. In the present invention, it is preferable to carry out the incubation under humidified conditions at 25° C. or more and 35° C. or less for 3 hours or more (preferably 8 hours or more) and 72 hours or less. Furthermore, when microorganisms are brought into contact with a test substance, and/or when microorganisms are incubated, sterilized water or a buffer solution may be added to the microorganisms, or medium components such as sugars, peptones produced from casein, peptones produced from soybean, a yeast extract, inorganic salts, a pH adjusting agent, and agar may be also added to those sterilized water and buffer solution. Alternatively, a commercially available medium may be also used directly or after diluting. Also, when incubation is carried out in the liquid state, it is preferable to shake the medium, and when incubation is carried out in the solid state, it is preferable to leave the medium to stand still.

In the present specification, the term "sebaceous dirt" means the most representative dirt that clings to fabric products such as garments. The sebaceous dirt contains large amounts of oil components such as free fatty acids and glycerides. Those components trapping carbon in dust, clay, or peeled keratin or the like, or those extracted from a fabric product after use or a fabric product after repeated wearing and washing may be used as a sebaceous dirt component.

As the sebaceous dirt component that can be preferably used in the present invention, a component of sebaceous dirt that can be usually seen in a fabric product such as garments can be used. However, a substance which has a potential to be a precursor of a damp-dry malodor-causing substance that is produced from fabric products, is preferred. Examples of the substance which has a potential to be a precursor of a damp-dry malodor-causing substance that is produced from fabric products, include anteiso fatty acids having 9 or more carbon atoms (preferably 11 or more carbon atoms, and more preferably 17 or more carbon atoms) and 21 or less carbon atoms (preferably 19 or less carbon atoms). Among these, compounds that are not actually present in the sebaceous dirt are also included. However, in the present specification, it is intended that these anteiso fatty acids are also included in the sebaceous dirt component. In the present invention, the sebaceous dirt component is preferably an anteiso fatty acid. The anteiso fatty acid that is preferably used in the present invention may be any of a saturated fatty acid and an unsaturated fatty acid, and it is defined that salts and esters of anteiso fatty acids are also included in the anteiso fatty acid. Specific examples thereof include 6-methyloctanoic acid, 8-methyldecanoic acid, 12-methyltetradecanoic acid, 14-methylhexadecanoic acid, 16-methyloctadecanoic acid, 14-methylhexadecenoic acid, and 16-methyloctadecenoic acid, and salts, esters and the like of these acids. In the present invention, the sebaceous dirt component is more preferably 14-methylhexadecanoic acid or 16-methyloctadecanoic acid.

The anteiso fatty acid that is preferably used in the present invention can be synthesized by an ordinary method (see, for example, JP-A-2009-149546). Furthermore, commercially available products can be also obtained from Sigma-Aldrich Company or the like and used.

In the present invention, the contact ratio (mixing ratio) of the microorganisms which produce damp-dry malodor-causing substances and the sebaceous dirt component can be appropriately determined. For example, 0.1 mg or more and 10 mg or less of the sebaceous dirt component such as an anteiso fatty acid may be preferably brought into contact with the microorganisms at a final concentration of $10^4$ CFU or more and $10^8$ CFU or less.

In the present invention, microorganisms which produce damp-dry malodor-causing substances and a test substance that are used in the present invention may be added to a fabric product to which a sebaceous dirt component is clung for bringing the microorganisms and the test substance into contact with each other, and the microorganisms may be incubated together with the test substance and the sebaceous dirt component. In this case, any incubation conditions for incubation may be used. In the present invention, it is preferable to carry out the incubation by allowing the system to stand still at 25° C. or more and 35° C. or less for 3 hours or more (preferably 8 hours or more) and 48 hours or less. Furthermore, the sebaceous dirt component may have clung to the fabric product from the beginning, or a sebaceous dirt component such as an anteiso fatty acid may be caused to cling to the fabric product. In the case of causing the sebaceous dirt component to cling to the fabric product, it is preferable to cause the sebaceous dirt component to cling to a fabric product having a size of 2×2 cm at a proportion of 0.1 mg or more and 1 mg or less.

The amount of addition of the microorganisms to a fabric product can be appropriately determined. For example, a microorganism suspension is preferably added to a fabric product to obtain a microbial population of $10^2$ CFU/cm$^2$ or more and $10^5$ CFU/cm$^2$ or less.

As the material of the fabric product, any material may be used, and the material may be any of natural materials such as wool, silk and cotton; chemical fabrics such as polyester and polyamide; and combinations thereof. In the present invention, the material of the fabric product is preferably cotton. Further, when a sebaceous dirt component is added and used, the fabric product may be in un-used state or after use of one or more times (that is, a fabric product after use but without washing, a fabric product after use and completed washing, or the like).

Regarding the evaluation method and the screening method of the present invention, the fatty acid desaturase and the β oxidation related enzyme, of which gene expression is determined, are explained herein below.

The fatty acid desaturase is an enzyme which produces an unsaturated fatty acid by eliminating two hydrogen atoms from a fatty acid and forming a carbon-carbon double bond in the fatty acid. In the present invention, the fatty acid desaturase is preferably an enzyme which is related to production of damp-dry malodor-causing substances such as 4M3H, more preferably an enzyme responsible for desaturation of a precursor of damp-dry malodor-causing substances, and further preferably an enzyme responsible for desaturation of a sebaceous dirt component such as anteisofatty acids. Examples of the fatty acid desaturase include Δ9desaturase, Δ5desaturase and Δ6desaturase. Among these, Δ9desaturase is particularly preferable.

With regard to the Δ9desaturase among the fatty acid desaturase, the amino acid sequence thereof and the base sequence of Δ9desaturase gene encoding the Δ9desaturase have been reported and described by Human Microbiome project (HMP, http://hmp.jcvi.org/jumpstart/hmp047/index.shtml). Of those, the base sequence of the Δ9desaturase gene of *Enhydrobacter aerosaccus* SK60 (accession No: NZ_ACYI01000046, gene No: ENHAE0001_1102) is set forth in SEQ ID NO: 1. Further, based on the result of comparing the gene sequences of 16S rRNA between *Enhydrobacter aerosaccus* SK60 and *Moraxella osloensis* ATCC19976, which exhibits 99.1% sequence similarity, and the report by Y. Kawamura et al. (Microbiology and Immunology, 2012, vol. 56, p. 21-26), possibility of re-classifying *Enhydrobacter aerosaccus* SK60 as *Moraxella osloensis* was strongly demonstrated. Moreover, from fatty acid composition analysis, it has been suggested that *Moraxella osloensis* may have Δ9desaturase (see, C. Sugimoto et al., International journal of systematic bacteriology, 1983, p. 181-187).

In the present invention, the base sequence of the Δ9desaturase gene may be a base sequence which has 70% or more sequence similarity to the base sequence set forth in SEQ ID NO: 1 or a complementary sequence thereof, and the sequence similarity is preferably 80% or more, more preferably 90% or more, still more preferably 95% or more, even more preferably 96.1% or more, even more preferably 97% or more, and particularly preferably 99% or more. Further, the Δ9desaturase gene may be a gene which has a base sequence set forth in SEQ ID NO: 1 with a deletion, a substitution, an insertion, or an addition of 1 to 351 bases (preferably 1 to 234 bases, more preferably 1 to 117 bases, and particularly preferably 1 to 59 bases), and encodes an enzyme having a fatty acid desaturation activity. The base sequence similarity is calculated, for example, by Lipman-Pearson method (Science, 227, p. 1435 (1985)). Specifically, it can be calculated by performing analysis using a homology analysis (Search homology) program of genetic information processing software Genetyx-Win (Software Development) while the unit size to compare (ktup) parameter is set to 2. Further, as for an example of the Δ9desaturase gene other than the base sequence set forth in SEQ ID NO: 1, which is a base sequence of the Δ9desaturase gene preferred in the present invention, the sequence similarities among the base sequence of Δ9desaturase gene from *Moraxella catarrhalis* RH4 (SEQ ID NO: 2, accession No: CP002005, gene No: MCR_0449, see Kyoto encyclopedia of genes and genomes (KEGG, http://www.genome.jp/kegg/kegg2.html)), the base sequence of Δ9desaturase gene from *Acinetobacter* sp. DR1 (SEQ ID NO: 3, accession No: CP002080, gene No: AOLE_06035), and the base sequence of Δ9desaturase gene from *Saccaromyces cerevisiae* YGL055W (SEQ ID NO: 4, accession No: Z72577, gene No: YGL055W) are shown in Table 1.

TABLE 1

| SEQ ID NO: | Sequence similarity to the base sequence set forth in SEQ ID NO: 1 |
|---|---|
| 2 | 63.7% |
| 3 | 56.0% |
| 4 | 49.0% |

The β oxidation-related enzyme is an enzyme which is involved with oxidation of the carbon at the β-position of an fatty acid. As a result of repeated β oxidation by the β oxidation-related enzyme, degradation of the carbon chain in the fatty acid progresses. In the present invention, the β oxidation-related enzyme is preferably an enzyme which is involved with production of damp-dry malodor-causing substances, such as 4M3H. More preferably, it is an enzyme responsible for β oxidation of an unsaturated fatty acid produced by the fatty acid desaturase. Still more preferably, it is an enzyme responsible for β oxidation of an unsaturated fatty acid as a desaturation product of a sebaceous dirt component such as an anteiso-fatty acid by the fatty acid desaturase. Specific examples of the β oxidation-related enzyme include the following enzymes (1) to (4).

(1) fadD for converting a fatty acid into acyl CoA in ATP dependent manner
(2) fadE for forming α,β-trans double bond based on dehydrogenation
(3) fadB for producing L-3-hydroxy acyl CoA by hydration of double bond and producing 3-oxoacyl CoA by dehydrogenation in NAD dependent manner
(4) fadA for producing acetyl CoA and acyl CoA with two less carbon atoms by breaking the carbon-carbon bond between the α-position and the β-position via reaction with CoA.

Among these enzymes, fadB and fadD are preferable.

With regard to the fadB among the β oxidation-related enzyme, the amino acid sequence thereof and the base sequence of fadB gene encoding the fadB have been reported and described by HMP (http://hmp.jcvi.org/jump-start/hmp047/index.shtml). Of those, the base sequence of the fadB gene of *Enhydrobacter aerosaccus* SK60 (accession No: NZ_ACYI01000046, gene No: ENHAE0001_0891) is set forth in SEQ ID NO: 5.

In the present invention, the base sequence of the fadB gene may be a base sequence which has 70% or more sequence similarity to the base sequence set forth in SEQ ID NO: 5 or a complementary sequence thereof, and the sequence similarity is preferably 80% or more, more preferably 90% or more, still more preferably 95% or more, even more preferably 95.2% or more, even more preferably 97% or more, and particularly preferably 99% or more. Further, the fadB gene may be a gene which has a base sequence set forth in SEQ ID NO: 5 with a deletion, a substitution, an insertion, or an addition of 1 to 647 bases (preferably 1 to 431 bases, more preferably 1 to 216 bases, and particularly preferably 1 to 108 bases), and encodes an enzyme having a β oxidation activity of an unsaturated fatty acid. The base sequence similarity is calculated, for example, by Lipman-Pearson method (Science, 227, p. 1435 (1985)). Specifically, it can be calculated by performing analysis using a homology analysis (Search homology) program of genetic information processing software Genetyx-Win (Software Development) while the unit size to compare (ktup) parameter is set to 2. Further, as for an example of the fadB gene other than the base sequence set forth in SEQ ID NO: 5, which is a base sequence of the fadB gene preferred in the present invention, the sequence similarities among the base sequence of fadB gene from *Moraxella catarrhalis* RH4 (SEQ ID NO: 6, accession No: CP002005, gene No: MCR_0091, see KEGG (http://www.genome.jp/kegg/kegg2.html)), the base sequence of fadB gene from *Acinetobacter* sp. DR1 (SEQ ID NO: 7, accession No: CP002080, gene No: AOLE_17905), and the base sequence of fadB gene from *Escherichia coli* K12 MG1655 (SEQ ID NO: 8, accession No: AP012306, gene No: b3846) are shown in Table 2.

TABLE 2

| SEQ ID NO: | Sequence similarity to the base sequence set forth in SEQ ID NO: 5 |
|---|---|
| 6 | 68.5% |
| 7 | 67.5% |
| 8 | 56.7% |

With regard to the fadD among the β oxidation-related enzyme, the amino acid sequence thereof and the base sequence of fadD gene encoding the fadD have been reported and described by HMP (http://hmp.jcvi.org/jump-start/hmp047/index.shtml). Of those, the base sequence of the fadD gene of *Enhydrobacter aerosaccus* SK60 (accession No: NZ_ACYI01000046, gene No: ENHAE0001_2256) is set forth in SEQ ID NO: 9.

In the present invention, the base sequence of the fadD gene may be a base sequence which has 70% or more sequence similarity to the base sequence set forth in SEQ ID NO: 9 or a complementary sequence thereof, and the sequence similarity is preferably 80% or more, more preferably 90% or more, still more preferably 95% or more, even more preferably 95.4% or more, even more preferably 97% or more, and particularly preferably 99% or more. Further, the fadD gene may be a gene which has a base sequence set forth in SEQ ID NO: 9 with a deletion, a substitution, an insertion, or an addition of 1 to 506 bases (preferably 1 to 377 bases, more preferably 1 to 169 bases, and particularly preferably 1 to 84 bases), and encodes an enzyme having a β oxidation activity of an unsaturated fatty acid. The base sequence similarity is calculated, for example, by Lipman-Pearson method (Science, 227, p. 1435 (1985)). Specifically, it can be calculated by performing analysis using a homology analysis (Search homology) program of genetic information processing software Genetyx-Win (Software Development) while the unit size to compare (ktup) parameter is set to 2. Further, as for an example of the fadD gene other than the base sequence set forth in SEQ ID NO: 9, which is a base sequence of the fadD gene preferred in the present invention, the sequence similarities among the base sequence of fadD gene from *Moraxella catarrhalis* RH4 (SEQ ID NO: 10, accession No: CP002005, gene No: MCR_1388, see KEGG (http://www.genome.jp/kegg/kegg2.html)), the base sequence of fadD gene from *Acinetobacter* sp DR1 (SEQ ID NO: 11, accession No: CP002080, gene No: AOLE_18375), and the base sequence of fadD gene from *Escherichia coli* K12 MG1655 (SEQ ID NO: 8, accession No: AP012306, gene No: b1805) are shown in Table 3.

TABLE 3

| SEQ ID NO: | Sequence similarity to the base sequence set forth in SEQ ID NO: 9 |
|---|---|
| 10 | 53.6% |
| 11 | 53.5% |
| 12 | 51.7% |

Generally, examples of the action mechanism of the damp-dry malodor inhibitor includes sterilization of microorganisms that cling into a fabric product, prevention of the conversion of sweat, sebum or the like that remains in a fabric product to a damp-dry malodor-causing substance, decomposition or conversion of a damp-dry malodor-causing substance into an odorless substance, and masking of a damp-dry malodor. The action mechanism of the damp-dry malodor inhibitor in the present invention is related to prevention of the conversion of sweat, sebum, or the like that remains in a fabric product into a damp-dry malodor-causing substance.

By an activation of the fatty acid desaturase in microorganisms which produce damp-dry malodor-causing substances, desaturation of fatty acids as a precursor of damp-dry malodor-causing substances is caused. Moreover, from the unsaturated fatty acids produced by the reaction, damp-dry malodor-causing substances are generated in accordance with β oxidation reaction by the β oxidation-related enzyme.

As an example, the mechanism for producing damp-dry malodor-causing substances (4M3H) from 16-methyloctadecanoic acid as a substrate, which is one kind of anteiso-fatty acid, by microorganisms which produce damp-dry malodor-causing substances is described below.

(b) described above, an oligonucleotide pair containing the oligonucleotides (c) and (d) described above, an oligonucleotide pair containing the oligonucleotides (e) and (f) described above, an oligonucleotide pair containing the oligonucleotides (g) and (h) described above, an oligonucleotide pair containing the oligonucleotides (i) and (j) described above, an oligonucleotide pair containing the oligonucleotides (k) and (l) described above, an oligonucleotide pair containing the oligonucleotides (m) and (n) described above, an oligonucleotide pair containing the oligonucleotides (o) and (p) described above, an oligonucleotide pair containing the oligonucleotides (q) and (r) described above, an oligonucleotide pair containing the oligonucleotides (s) and (t) described above, an oligonucleotide pair containing the oligonucleotides (u) and (v) described above, an oligonucleotide pair containing the oligonucleotides (w) and (x) described above, an oligonucleotide pair containing the oligonucleotides (y) and (z) described above, an oligonucleotide pair containing the oligonucleotides (a1) and (b1) described above, and an oligonucleotide pair containing the oligonucleotides (c1) and (d1) described above.

In the present invention, the fatty acid desaturase gene is preferably the Δ9desaturase gene. In the case of detecting the Δ9desaturase gene, it is preferably that at least one kind of oligonucleotide pair selected from a pair of the above-described oligonucleotides (a) and (b), a pair of the above-described oligonucleotides (c) and (d), a pair of the above-described oligonucleotides (e) and (f), a pair of the above-described oligonucleotides (g) and (h), a pair of the above-described oligonucleotides (i) and (j), and a pair of the above-described oligonucleotides (k) and (l) is used.

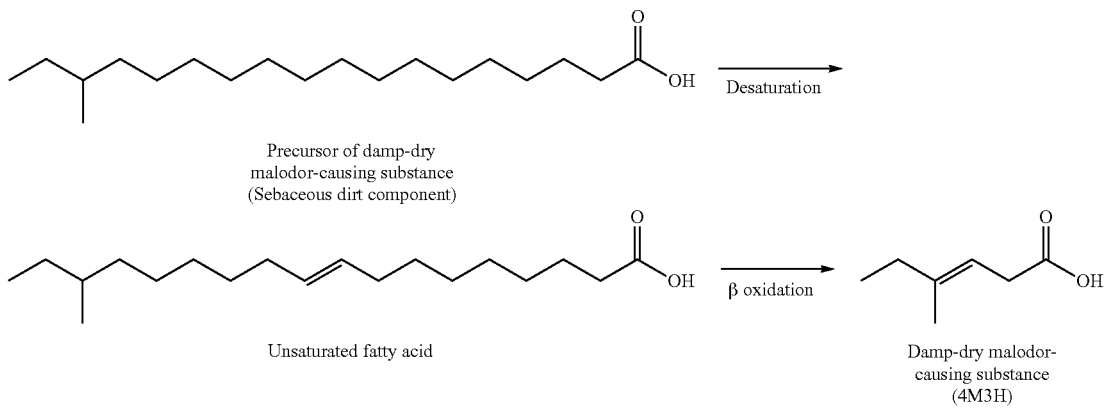

In the present invention, expression of the fatty acid desaturase gene and the β oxidation-related enzyme gene can be detected by an ordinary method. For example, by carrying out a polymerase chain reaction (PCR) using nucleic acid primers for detecting the fatty acid desaturase gene and the β oxidation-related enzyme gene, and determining the presence or absence of an amplified product, the gene expression can be detected. Alternatively, it is also possible that real time PCR is carried out using the same primer and the gene expression amount is quantitatively determined to detect the gene expression.

In the present invention, the detection of at least one kind of gene selected from the fatty acid desaturase gene and the β oxidation-related enzyme gene is performed by using at least one kind of oligonucleotide pair selected from an oligonucleotide pair containing the oligonucleotides (a) and The oligonucleotides (a) to (l) are preferably an oligonucleotide having the base sequence set forth in any one of SEQ ID NOS: 13 to 24. Further, in the present invention, an oligonucleotide preferably usable for detection of the fatty acid desaturase gene (in particular, the Δ9desaturase gene) may have sequence similarity of 70% or more with the base sequence set forth in any one of SEQ ID NOS: 13 to 24 as long as it can be used for detection of the fatty acid desaturase gene (preferably, the Δ9desaturase gene). The sequence similarity is preferable 75% or more, more preferably 80% or more, still more preferably 85% or more, even more preferably 90% or more, and particularly preferably 95% or more. Further, the oligonucleotide preferably usable for detection of the fatty acid desaturase gene (preferably, the Δ9desaturase gene) includes an oligonucleotide which has a base sequence set forth in any one of SEQ ID NOS: 13 to 24 with a deletion, a substitution, an insertion, or an addition of 1 to several bases (preferably 1 to 5 bases, more preferably 1 to 4 bases, still more preferably 1 to 3 bases, even still more preferably 1 or 2 bases, and particularly preferably 1 base), and is usable for detection of the fatty acid desaturase gene (preferably, the Δ9desaturase gene). Moreover, an appropriate base sequence may be added to the base sequence set forth in any one of SEQ ID NOS: 13 to 24.

The base sequence similarity is calculated, for example, by Lipman-Pearson method (Science, 227, p. 1435 (1985)). Specifically, it can be calculated by performing analysis using a homology analysis (Search homology) program of genetic information processing software Genetyx-Win (Software Development) while the unit size to compare (ktup) parameter is set to 2.

To a nucleic acid having the base sequence set forth in SEQ ID NO: 1 or a base sequence having sequence similarity of 70% or more with the base sequence set forth in SEQ ID NO: 1, an oligonucleotide having the base sequence set forth in any one of SEQ ID NOS: 13 to 24 hybridizes under stringent conditions. Regions to which the oligonucleotide having the base sequence set forth in any one of SEQ ID NOS: 13 to 24 hybridizes in the base sequence set forth in SEQ ID NO: 1 are shown in Table 4, for example. As shown in Table 4, the oligonucleotide having the base sequence set forth in any one of SEQ ID NOS: 13 to 24 can hybridize under stringent conditions to the fatty acid desaturase gene of microorganisms which produce damp-dry malodor-causing substances. Thus, when an amplification reaction is carried out by using, as nucleic acid primers, at least one oligonucleotide pair selected from an oligonucleotide pair containing the oligonucleotides (a) and (b) described above, an oligonucleotide pair containing the oligonucleotides (c) and (d) described above, an oligonucleotide pair containing the oligonucleotides (e) and (f) described above, an oligonucleotide pair containing the oligonucleotides (g) and (h) described above, an oligonucleotide pair containing the oligonucleotides (i) and (j) described above, and an oligonucleotide pair containing the oligonucleotides (k) and (l) described above, an amplification product of the fatty acid desaturase gene is obtained. For such reasons, without performing base sequence analysis, it becomes possible to identify the amplification product obtained by performing the amplification reaction using the above oligonucleotide pair as nucleic acid primers with an amplification product of the fatty acid desaturase gene. As a result, expression of the fatty acid desaturase gene of microorganisms which product damp-dry malodor-causing substances can be easily detected.

It should be note that, in this description, the "stringent conditions" includes, for example, the method described in Molecular Cloning-A LABORATORY MANUAL THIRD EDITION [Joseph Sambrook, David W. Russell. Cold Spring Harbor Laboratory Press], and examples thereof include conditions where hybridization is performed by incubating a solution containing 6×SSC (composition of 1×SSC: 0.15M sodium chloride, 0.015M sodium citrate, pH7.0), 0.5% SDS, 5×Denhardt and 100 mg/mL herring sperm DNA together with a probe at 65° C. for 8 to 16 hours.

TABLE 4

| | SEQ ID NO: | SEQ ID NO: 1 |
|---|---|---|
| (a) | 13 | From 618-position to 637-position |
| (b) | 14 | From 750-position to 768-position |
| (c) | 15 | From 532-position to 554-position |

TABLE 4-continued

| | SEQ ID NO: | SEQ ID NO: 1 |
|---|---|---|
| (d) | 16 | From 633-position to 655-position |
| (e) | 17 | From 639-position to 661-position |
| (f) | 18 | From 741-position to 763-position |
| (g) | 19 | From 638-position to 660-position |
| (h) | 20 | From 741-position to 763-position |
| (i) | 21 | From 532-position to 554-position |
| (j) | 22 | From 631-position to 653-position |
| (k) | 23 | From 280-position to 302-position |
| (l) | 24 | From 387-position to 409-position |

In the present invention, the β oxidation-related enzyme gene is preferably fadB gene or fadD gene.

In the case of detecting the fadB gene, it is preferably that at least one kind of oligonucleotide pair selected from a pair of the above-described oligonucleotides (m) and (n), a pair of the above-described oligonucleotides (o) and (p), a pair of the above-described oligonucleotides (q) and (r), and a pair of the above-described oligonucleotides (s) and (t) is used. In the case of detecting the fadD gene, it is preferably that at least one kind of oligonucleotide pair selected from a pair of the above-described oligonucleotides (u) and (v), and a pair of the above-described oligonucleotides (w) and (x), and a pair of the above-described oligonucleotides (y) and (z), and a pair of the above-described oligonucleotides (a1) and (b1), and a pair of the above-described oligonucleotides (c1) and (d1) is used.

The oligonucleotides (m) to (z) and (a1) to (d1) are preferably an oligonucleotide having the base sequence set forth in any one of SEQ ID NOS: 25 to 42. Further, in the present invention, an oligonucleotide preferably usable for detection of the β oxidation-related enzyme gene (in particular, the fadB gene or the fadD gene) may have sequence similarity of 70% or more with the base sequence set forth in any one of SEQ ID NOS: 25 to 42 as long as it can be used for detection of the 1 oxidation-related enzyme gene (in particular, the fadB gene or the fadD gene). The sequence similarity is preferable 75% or more, more preferably 80% or more, still more preferably 85% or more, even more preferably 90% or more, and particularly preferably 95% or more. Further, the oligonucleotide preferably usable for detection of the β oxidation-related enzyme gene (in particular, the fadB gene or the fadD gene) includes an oligonucleotide which has a base sequence set forth in any one of SEQ ID NOS: 25 to 42 with a deletion, a substitution, an insertion, or an addition of 1 to several bases (preferably 1 to 5 bases, more preferably 1 to 4 bases, still more preferably 1 to 3 bases, even still more preferably 1 or 2 bases, and particularly preferably 1 base), and is usable for detection of the β oxidation-related enzyme gene (in particular, the fadB gene or the fadD gene). Moreover, an appropriate base sequence may be added to the base sequence set forth in any one of SEQ ID NOS: 25 to 42.

The base sequence similarity is calculated, for example, by Lipman-Pearson method (Science, 227, p. 1435 (1985)). Specifically, it can be calculated by performing analysis using a homology analysis (Search homology) program of genetic information processing software Genetyx-Win (Software Development) while the unit size to compare (ktup) parameter is set to 2.

To a nucleic acid having the base sequence set forth in SEQ ID NO: 5 or a base sequence having sequence similarity of 70% or more with the base sequence set forth in SEQ ID NO: 5, an oligonucleotide having the base sequence set forth in any one of SEQ ID NOS: 25 to 32 hybridizes under stringent conditions. Regions to which the oligonucleotide having the base sequence set forth in any one of SEQ ID NOS: 25 to 32 hybridizes in the base sequence set forth in SEQ ID NO: 5 are shown in Table 5, for example. As shown in Table 5, the oligonucleotide having the base sequence set forth in any one of SEQ ID NOS: 25 to 32 can hybridize under stringent conditions to the β oxidation-related enzyme gene of microorganisms which produce damp-dry malodor-causing substances. Thus, when an amplification reaction is carried out by using, as nucleic acid primers, at least one oligonucleotide pair selected from an oligonucleotide pair containing the oligonucleotides (m) and (n) described above, an oligonucleotide pair containing the oligonucleotides (o) and (p) described above, an oligonucleotide pair containing the oligonucleotides (q) and (r) described above, and an oligonucleotide pair containing the oligonucleotides (s) and (t) described above, an amplification product of the β oxidation-related enzyme (fadB) gene is obtained. For such reasons, without performing base sequence analysis, it becomes possible to identify the amplification product obtained by performing the amplification reaction using the above oligonucleotide pair as nucleic acid primers with an amplification product of the β oxidation-related enzyme (fadB) gene. As a result, expression of the β oxidation-related enzyme (fadB) gene of microorganisms which product damp-dry malodor-causing substances can be easily detected.

TABLE 5

|  | SEQ ID NO: | SEQ ID NO: 5 |
| --- | --- | --- |
| (m) | 25 | From 1914-position to 1936-position |
| (n) | 26 | From 2091-position to 2113-position |
| (o) | 27 | From 1430-position to 1452-position |
| (p) | 28 | From 1604-position to 1626-position |
| (q) | 29 | From 1136-position to 1158-position |
| (r) | 30 | From 1311-position to 1333-position |
| (s) | 31 | From 284-position to 306-position |
| (t) | 32 | From 461-position to 483-position |

To a nucleic acid having the base sequence set forth in SEQ ID NO: 9 or a base sequence having sequence similarity of 70% or more with the base sequence set forth in SEQ ID NO: 9, an oligonucleotide having the base sequence set forth in any one of SEQ ID NOS: 33 to 42 hybridizes under stringent conditions. Regions to which the oligonucleotide having the base sequence set forth in any one of SEQ ID NOS: 33 to 42 hybridizes in the base sequence set forth in SEQ ID NO: 9 are shown in Table 6, for example. As shown in Table 6, the oligonucleotide having the base sequence set forth in any one of SEQ ID NOS: 33 to 42 can hybridize under stringent conditions to the β oxidation-related enzyme gene of microorganisms which produce damp-dry malodor-causing substances. Thus, when an amplification reaction is carried out by using, as nucleic acid primers, at least one oligonucleotide pair selected from an oligonucleotide pair containing the oligonucleotides (u) and (v) described above, an oligonucleotide pair containing the oligonucleotides (w) and (x) described above, an oligonucleotide pair containing the oligonucleotides (y) and (z) described above, an oligonucleotide pair containing the oligonucleotides (a1) and (b1) described above, and an oligonucleotide pair containing the oligonucleotides (c1) and (d1) described above, an amplification product of the β oxidation-related enzyme (fadD) gene is obtained. For such reasons, without performing base sequence analysis, it becomes possible to identify the amplification product obtained by performing the amplification reaction using the above oligonucleotide pair as nucleic acid primers with an amplification product of the 13 oxidation-related enzyme (fadD) gene. As a result, expression of the $3 oxidation-related enzyme (fadD) gene of microorganisms which product damp-dry malodor-causing substances can be easily detected.

TABLE 6

|  | SEQ ID NO: | SEQ ID NO: 9 |
| --- | --- | --- |
| (u) | 33 | From 46-position to 68-position |
| (v) | 34 | From 152-position to 174-position |
| (w) | 35 | From 46-position to 68-position |
| (x) | 36 | From 153-position to 175-position |
| (y) | 37 | From 124-position to 146-position |
| (z) | 38 | From 224-position to 246-position |
| (a1) | 39 | From 521-position to 543-position |
| (b1) | 40 | From 624-position to 646-position |
| (c1) | 41 | From 115-position to 137-position |
| (d1) | 42 | From 223-position to 245-position |

The bonding pattern of the oligonucleotide includes not only a phosphodiester bond present in a natural nucleic acid but also a phosphoroamidate bond and a phosphorothioate bond, for example.

The oligonucleotide can be prepared by an ordinary synthetic method such as chemical synthesis using an automatic DNA synthesizer or the like. Alternatively, it is also possible that it is directly cut from the Δ9desaturase gene, the fadB gene, or the fadD gene using a restriction enzyme or the like, or after isolation and purification following gene cloning, it may be prepared by digestion using a restriction enzyme or the like. From the viewpoint of easiness of operation and obtaining an oligonucleotide with constant quality in large amount at low cost, preparation is preferably carried out by chemical synthesis.

The medium-chain branched fatty acids such as 4M3H are the damp-dry malodor-causing substances. These are produced by involvement of the fatty acid desaturase and the β oxidation-related enzyme derived from microorganisms which produce damp-dry malodor-causing substances, utilizing a sebaceous dirt component as a substrate. That is, in accordance with a decrease in expression amount of at least one of the fatty acid desaturase gene and the β oxidation-related enzyme gene, production of the medium-chain branched fatty acids, such as 4M3H, that are the damp-dry malodor-causing substances, is suppressed. Thus, by analyzing a change in expression amount of at least one of the fatty acid desaturase gene and the β oxidation-related enzyme gene derived from microorganisms in the presence of a test substance, evaluation of inhibitory effect on damp-dry malodor and screening of a damp-dry malodor inhibitor can be achieved. For example, microorganisms which produce damp-dry malodor-causing substances are brought into contact with a test substance in the presence of a sebaceous dirt component (for example, on a fabric product such as clothes not washed after use or a fabric product such as clothes washed after use, which contains a sebaceous dirt components, microorganisms which produce damp-dry malodor-causing substances and a test substance are brought into contact with each other). After incubating the microorganisms with the test substance, PCR or real time PCR is carried out by using nucleic acid primers designed based on the fatty acid desaturase gene or the β oxidation-related enzyme gene. Then, presence or absence of an amplified product or expression amount of the gene is analyzed. Compared to the gene expression amount for a case in which the same procedures are carried out in the absence of the test substance, when no amplified product is found or the gene expression amount is reduced, it can be evaluated that the test substance has inhibitory effect on damp-dry malodor, and the test substance can be selected as a damp-dry malodor inhibitor.

In the method of detecting microorganisms which produce damp-dry malodor-causing substances, the detection of the microorganisms which produce damp-dry malodor-causing substances is performed by using at least one kind of oligonucleotide pair selected from an oligonucleotide pair containing the oligonucleotides (a) and (b) described above, an oligonucleotide pair containing the oligonucleotides (c) and (d) described above, an oligonucleotide pair containing the oligonucleotides (e) and (f) described above, an oligonucleotide pair containing the oligonucleotides (g) and (h) described above, an oligonucleotide pair containing the oligonucleotides (i) and (j) described above, an oligonucleotide pair containing the oligonucleotides (k) and (l) described above, an oligonucleotide pair containing the oligonucleotides (m) and (n) described above, an oligonucleotide pair containing the oligonucleotides (o) and (p) described above, an oligonucleotide pair containing the oligonucleotides (q) and (r) described above, an oligonucleotide pair containing the oligonucleotides (s) and (t) described above, an oligonucleotide pair containing the oligonucleotides (u) and (v) described above, an oligonucleotide pair containing the oligonucleotides (w) and (x) described above, an oligonucleotide pair containing the oligonucleotides (y) and (z) described above, an oligonucleotide pair containing the oligonucleotides (a1) and (b1) described above, and an oligonucleotide pair containing the oligonucleotides (c1) and (d1) described above. Thus, without being bound to separation and identification of microorganisms which produce damp-dry malodor-causing substances using the oligonucleotide pair, microorganisms which produce damp-dry malodor-causing substances can be quickly and accurately detected. Further, as used herein, the term "detect" includes "identify" used in taxonomy.

The kind of microorganisms that are detected by the detection method of the present invention include the microorganisms to be used for the evaluation method of the present invention.

Each oligonucleotide pair used for the method of detecting microorganisms which produce damp-dry malodor-causing substances of the present invention are the same as the oligonucleotide pair used for the method of screening a damp-dry malodor inhibitor and the method of evaluating inhibitory effect on damp-dry malodor of the present invention that are described above.

In the method of detecting microorganisms which produce damp-dry malodor-causing substances of the present invention, amplification of a fragment of at least one kind of gene selected from the fatty acid desaturase gene and the β oxidation-related enzyme gene is performed using the above-described oligonucleotide pair. Moreover, for both the method of screening a damp-dry malodor inhibitor and the method of evaluating inhibitory effect on damp-dry malodor of the present invention, in order to detect expression of at least one kind of gene selected from the fatty acid desaturase gene and the β oxidation-related enzyme gene, it is preferable to perform amplification of a fragment of at least one kind of gene selected from the expressed fatty acid desaturase gene and the expressed β oxidation-related enzyme gene by using the oligonucleotide pair described above. When an amplification reaction is carried out by using the oligonucleotide pair of the present invention, an amplified product is obtained when at least one kind of gene selected from the fatty acid desaturase gene and the β oxidation-related enzyme gene is present. Thus, obtainment of an amplified product indicates presence of at least one kind of gene selected from the fatty acid desaturase gene and the β oxidation-related enzyme. For such reasons, without performing the base sequence analysis of an amplified product, it is possible to detect at least one kind of gene selected from the fatty acid desaturase gene and the β oxidation-related enzyme gene, or to detect microorganisms having at least one kind of gene selected from the fatty acid desaturase gene and the β oxidation-related enzyme gene, that is, microorganisms which produce damp-dry malodor-causing substances.

An ordinary method such as PCR method, the real time PCR method, LCR (ligase chain reaction) method, SDA (strand displacement amplification) method, NASBA (nucleic acid sequence-based amplification) method, RCA (rolling-circle amplification) method, or LAMP (loop mediated isothermal amplification) method may be used to amplify a fragment of at least one kind of gene selected from the fatty acid desaturase gene and the β oxidation-related enzyme gene. However, in the present invention, the PCR method is preferably used.

Hereinafter, a specific example of the method of amplifying a gene fragment by PCR in the present invention will be described in more.

In the present invention, for amplifying a fragment of the fatty acid desaturase gene (in particular, the Δ9desaturase gene), it is preferable that PCR is performed by using, as nucleic acid primers, at least one kind of oligonucleotide pair selected from an oligonucleotide pair containing the oligonucleotides (a) and (b) described above, an oligonucleotide pair containing the oligonucleotides (c) and (d) described above, an oligonucleotide pair containing the oligonucleotides (e) and (f) described above, an oligonucleotide pair containing the oligonucleotides (g) and (h) described above, an oligonucleotide pair containing the oligonucleotides (i) and (j) described above, and an oligonucleotide pair containing the oligonucleotides (k) and (l) described above, and amplifying a part of the nucleic acid of the fatty acid desaturase gene of the microorganisms which produce damp-dry malodor-causing substances.

The oligonucleotides (a) and (b) described above, the oligonucleotides (c) and (d) described above, the oligonucleotides (e) and (f) described above, the oligonucleotides (g) and (h) described above, the oligonucleotides (i) and (j) described above, and the oligonucleotides (k) and (l) described above are useful for amplifying, by PCR, a fragment (part) of the fatty acid desaturase gene (in particular, the Δ9desaturase gene) of the microorganisms which produce damp-dry malodor-causing substances. As described above, the fatty acid desaturase is related to production of the damp-dry malodor-causing substances such as 4M3H. Thus, an oligonucleotide pair containing the oligonucleotides (a) and (b) described above, an oligonucleotide pair containing oligonucleotides (c) and (d) described above, an oligonucleotide pair containing oligonucleotides (e) and (f) described above, an oligonucleotide pair containing oligonucleotides (g) and (h) described above, an oligonucleotide pair containing oligonucleotides (i) and (j) described above, and an oligonucleotide pair containing oligonucleotides (k) and (l) described above can be preferably used for detection of the expression of the fatty acid desaturase gene or detection of microorganisms which produce damp-dry malodor-causing substances in the method of evaluating inhibitory effect on damp-dry malodor or a method of screening a damp-dry malodor inhibitor.

In the present invention, for amplifying a fragment of the β oxidation-related enzyme gene (in particular, the fadB gene or the fadD gene), it is preferable that PCR is performed by using, as nucleic acid primers, at least one kind of oligonucleotide pair selected from an oligonucleotide pair containing the oligonucleotides (m) and (n) described above, an oligonucleotide pair containing the oligonucleotides (o) and (p) described above, an oligonucleotide pair containing the oligonucleotides (q) and (r) described above, an oligonucleotide pair containing the oligonucleotides (s) and (t) described above, an oligonucleotide pair containing the oligonucleotides (u) and (v) described above, an oligonucleotide pair containing the oligonucleotides (w) and (x) described above, an oligonucleotide pair containing the oligonucleotides (y) and (z) described above, an oligonucleotide pair containing the oligonucleotides (a1) and (b1) described above, and an oligonucleotide pair containing the oligonucleotides (c1) and (d1) described above, and amplifying a part of the nucleic acid of the β oxidation-related enzyme gene of the microorganisms which produce damp-dry malodor-causing substances.

The oligonucleotides (m) and (n) described above, the oligonucleotides (o) and (p) described above, the oligonucleotides (q) and (r) described above, and the oligonucleotides (s) and (t) described above are useful for amplifying, by PCR, a fragment (part) of the β oxidation-related enzyme gene (in particular, the fadB gene) of the microorganisms which produce damp-dry malodor-causing substances. Further, the oligonucleotides (u) and (v) described above, the oligonucleotides (w) and (x) described above, the oligonucleotides (y) and (z) described above, the oligonucleotides (a1) and (b1) described above, and the oligonucleotides (c1) and (d1) described above are useful for amplifying, by PCR, a fragment (part) of the β oxidation-related enzyme gene (in particular, the fadD gene) of the microorganisms which produce damp-dry malodor-causing substances. As described above, the β oxidation-related enzyme is related to production of the damp-dry malodor-causing substances such as 4M3H. Thus, an oligonucleotide pair containing the oligonucleotides (m) and (n) described above, an oligonucleotide pair containing the oligonucleotides (o) and (p) described above, an oligonucleotide pair containing the oligonucleotides (q) and (r) described above, an oligonucleotide pair containing the oligonucleotides (s) and (t) described above, an oligonucleotide pair containing the oligonucleotides (u) and (v) described above, an oligonucleotide pair containing the oligonucleotides (w) and (x) described above, an oligonucleotide pair containing the oligonucleotides (y) and (z) described above, an oligonucleotide pair containing the oligonucleotides (a1) and (b1) described above, and an oligonucleotide pair containing the oligonucleotides (c1) and (d1) described above can be preferably used for detection of the expression of the β oxidation-related enzyme gene or detection of microorganisms which produce damp-dry malodor-causing substances in the method of evaluating inhibitory effect on damp-dry malodor or a method of screening a damp-dry malodor inhibitor.

Conditions of the PCR reaction can be appropriately determined so that a DNA fragment of interest can be amplified to a detectable degree.

For example, when PCR is carried out by using, as nucleic acid primers, the at least one kind of oligonucleotide pair, thermal denaturation for about 5 sec (preferably 5 sec) or more and about 60 sec (preferably 60 sec) or less at the temperature of 95° C. or more and 98° C. or less for converting the double stranded DNA to the single stranded DNA is performed. Next, an annealing reaction for hybridizing the primer pair to the single stranded DNA is performed for about 5 sec (preferably 5 sec) or more and about 60 sec (preferably 60 sec) or less at the temperature of 55° C. or more (preferably 59° C. or more) and 65° C. or less (preferably 62° C.), and more preferably for 60 sec at 61° C. Next, an elongation reaction for an action of DNA polymerase is performed for about 10 sec (preferably 10 sec) or more and about 60 sec (preferably 60 sec) or less at the temperature of about 72° C. By having the above steps as one cycle, about 30 cycles (preferably 30 cycles) or more and about 35 cycles (preferably 35 cycles) or less are performed.

In the method of detecting microorganisms which produce damp-dry malodor-causing substances, identification of the gene fragment can be carried out by an ordinary method. For example, a method of confirming presence or absence of a band with a size corresponding to the amplified gene by performing electrophoresis of the amplified product, and a method of measuring an amount of the amplified product over time can be mentioned. In the present invention, a method of confirming presence or absence of a band with a size corresponding to the amplified gene by performing electrophoresis after the gene amplification is preferable. Moreover, identification of the amplified product can be performed by on ordinary method. Examples thereof include a method of incorporating a nucleotide labeled with a radioactive substance or the like during amplification, a method of using a primer labeled with a fluorescent material or the like, and a method of inserting, between two DNA strands, a fluorescent material such as ethidium bromide for enhancing fluorescence intensity based on binding to DNA. In the present invention, a method of inserting, between two DNA strands, a fluorescent material for enhancing fluorescence intensity which binds to DNA is preferable.

When microorganisms to be detected are included in a sample, by performing PCR using the oligonucleotide pair of the present invention as a primer set and performing electrophoresis of an obtained PCR product, a DNA fragment with specific size can be identified.

By carrying out those processes, it is possible to identify whether or not the microorganisms as a detection subject are contained in a sample.

As the sample to be used in the present invention, any sample, such as fibers, fabric, soil, plastic, paper, plant, mixed microbes, isolated microbes, and cultured microbes, can be used. A method of preparing DNA from a sample may be any method so that DNA can be obtained at a sufficient purification degree and in a sufficient amount for detecting microorganisms which produce damp-dry malodor-causing substances. The sample may be used without purification. Alternatively, the sample may be subjected to a pre-treatment such as separation, extraction, concentration, or purification before use. For example, the sample may be purified by phenol and chloroform extraction or may be purified using a commercially available extraction kit, to increase the purity of the nucleic acid before use. Moreover, DNA obtained by reverse transcription of RNA in a sample may be used.

Examples of the microorganisms to be detected by the method of detecting microorganisms which produce damp-dry malodor-causing substances of the present invention include bacteria of genus *Moraxella* such as *Moraxella osloensis* and *Moraxella* sp.

The kit for evaluating inhibitory effect on damp-dry malodor and the kit for screening a damp-dry malodor inhibitor of the present invention contains microorganisms which produce damp-dry malodor-causing substances and a sebaceous dirt component such as an anteiso fatty acid. The microorganisms which produce damp-dry malodor-causing substances and the sebaceous dirt component such as an anteiso fatty acid are as described above. The kits may further contain a fabric product to be contacted with microorganisms which produce damp-dry malodor-causing substances and a test substance (for example, cotton fabric product after use) or a liquid to be contacted with microorganisms which produce damp-dry malodor-causing substances and a test substance (for example, physiological saline, buffer solution, and liquid medium). Moreover, for detection of the damp-dry malodor-causing substances such as 4M3H, a commercially available gas chromatography or the like may be used.

Further, the kit for evaluating inhibitory effect on damp-dry malodor, the kit for screening of a damp-dry malodor inhibitor, and the kit for detecting microorganisms which produce damp-dry malodor-causing substances each contains at least one kind of oligonucleotide selected from the above-described oligonucleotides (a) to (z) and (a1) to (d1); or at least one kind of oligonucleotide pair selected from a pair of the above-described oligonucleotides (a) and (b), a pair of the above-described oligonucleotides (c) and (d), a pair of the following oligonucleotides (e) and (f), a pair of the above-described oligonucleotides (g) and (h), a pair of the above-described oligonucleotides (i) and (j), a pair of the above-described oligonucleotides (k) and (l), a pair of the above-described oligonucleotides (m) and (n), a pair of the above-described oligonucleotides (o) and (p), a pair of the above-described oligonucleotides (q) and (r), a pair of the above-described oligonucleotides (s) and (t), a pair of the above-described oligonucleotides (u) and (v), a pair of the above-described oligonucleotides (w) and (x), a pair of the above-described oligonucleotides (y) and (z), a pair of the above-described oligonucleotides (a1) and (b1), and a pair of the above-described oligonucleotides (c1) and (d1).

The kits of the present invention may contain, depending on purpose, substances which are ordinary used for amplifying a gene fragment, such as a label-detecting substance, a buffer, a nucleic acid synthetase (such as a DNA polymerase, an RNA polymerase, or a reverse transcriptase), and an enzyme substrate (such as dNTP or rNTP). Further, the kits of the present invention may contain a positive control for confirming that a detection reaction can be made using the oligonucleotide or oligonucleotide pair of the present invention. The positive control is, for example, DNA including a region which is amplified by the method of the present invention.

With regard to the embodiments described above, also disclosed by the present invention includes a method of evaluating inhibitory effect on damp-dry malodor described below, a method of screening a damp-dry malodor inhibitor described below, an oligonucleotide or an oligonucleotide pair described below, a kit for evaluating inhibitory effect on damp-dry malodor or a kit for screening a damp-dry malodor inhibitor described below, use described below, a method described below, and a kit for detecting microorganisms which produce damp-dry malodor-causing substances described below.

<1> A method of evaluating inhibitory effect on damp-dry malodor, containing the steps of:

bringing microorganisms which produce damp-dry malodor-causing substances and a test substance into contact with each other in the presence of a sebaceous dirt component;

detecting expression of at least one kind of gene selected from a fatty acid desaturase gene and a β oxidation-related enzyme gene derived from the microorganisms; and thereby evaluating a damp-dry malodor inhibitory function of the test substance based on a change in expression amount of the at least one kind of gene; wherein the expression of the at least one kind of gene is detected by using at least one kind of oligonucleotide pair selected from an oligonucleotide pair containing oligonucleotides (a) and (b) described below, an oligonucleotide pair containing oligonucleotides (c) and (d) described below, an oligonucleotide pair containing oligonucleotides (e) and (f) described below, an oligonucleotide pair containing oligonucleotides (g) and (h) described below, an oligonucleotide pair containing oligonucleotides (i) and (j) described below, an oligonucleotide pair containing oligonucleotides (k) and (l) described below, an oligonucleotide pair containing oligonucleotides (m) and (n) described below, an oligonucleotide pair containing oligonucleotides (o) and (p) described below, an oligonucleotide pair containing oligonucleotides (q) and (r) described below, an oligonucleotide pair containing oligonucleotides (s) and (t) described below, an oligonucleotide pair containing oligonucleotides (u) and (v) described below, an oligonucleotide pair containing oligonucleotides (w) and (x) described below, an oligonucleotide pair containing oligonucleotides (y) and (z) described below, an oligonucleotide pair containing oligonucleotides (a1) and (b1) described below, and an oligonucleotide pair containing oligonucleotides (c1) and (d1) described below:

(a) an oligonucleotide having the base sequence set forth in SEQ ID NO: 13, an oligonucleotide having a base sequence set forth in SEQ ID NO: 13 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the fatty acid desaturase gene, or an oligonucleotide having a base sequence which has 80% or more (preferably 85% or more, more preferably 90% or more, and further preferably 95% or more) sequence similarity to the base sequence set forth in SEQ ID NO: 13 and can be used for detecting the fatty acid desaturase gene;

(b) an oligonucleotide having the base sequence set forth in SEQ ID NO: 14, an oligonucleotide having a base sequence set forth in SEQ ID NO: 14 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the fatty acid desaturase gene, or an oligonucleotide having a base sequence which has 80% or more (preferably 85% or more, more preferably 90% or more, and further preferably 95% or more) sequence similarity to the base sequence set forth in SEQ ID NO: 14 and can be used for detecting the fatty acid desaturase gene;

(c) an oligonucleotide having the base sequence set forth in SEQ ID NO: 15, an oligonucleotide having a base sequence set forth in SEQ ID NO: 15 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the fatty acid desaturase gene, or an oligonucleotide having a base sequence which has 80% or more (preferably 85% or more, more preferably 90% or more, and further preferably 95% or more) sequence similarity to the base sequence set forth in SEQ ID NO: 15 and can be used for detecting the fatty acid desaturase gene;
(d) an oligonucleotide having the base sequence set forth in SEQ ID NO: 16, an oligonucleotide having a base sequence set forth in SEQ ID NO: 16 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the fatty acid desaturase gene, or an oligonucleotide having a base sequence which has 80% or more (preferably 85% or more, more preferably 90% or more, and further preferably 95% or more) sequence similarity to the base sequence set forth in SEQ ID NO: 16 and can be used for detecting the fatty acid desaturase gene;
(e) an oligonucleotide having the base sequence set forth in SEQ ID NO: 17, an oligonucleotide having a base sequence set forth in SEQ ID NO: 17 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the fatty acid desaturase gene, or an oligonucleotide having a base sequence which has 80% or more (preferably 85% or more, more preferably 90% or more, and further preferably 95% or more) sequence similarity to the base sequence set forth in SEQ ID NO: 17 and can be used for detecting the fatty acid desaturase gene;
(f) an oligonucleotide having the base sequence set forth in SEQ ID NO: 18, an oligonucleotide having a base sequence set forth in SEQ ID NO: 18 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the fatty acid desaturase gene, or an oligonucleotide having a base sequence which has 80% or more (preferably 85% or more, more preferably 90% or more, and further preferably 95% or more) sequence similarity to the base sequence set forth in SEQ ID NO: 18 and can be used for detecting the fatty acid desaturase gene;
(g) an oligonucleotide having the base sequence set forth in SEQ ID NO: 19, an oligonucleotide having a base sequence set forth in SEQ ID NO: 19 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the fatty acid desaturase gene, or an oligonucleotide having a base sequence which has 80% or more (preferably 85% or more, more preferably 90% or more, and further preferably 95% or more) sequence similarity to the base sequence set forth in SEQ ID NO: 19 and can be used for detecting the fatty acid desaturase gene;
(h) an oligonucleotide having the base sequence set forth in SEQ ID NO: 20, an oligonucleotide having a base sequence set forth in SEQ ID NO: 20 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the fatty acid desaturase gene, or an oligonucleotide having a base sequence which has 80% or more (preferably 85% or more, more preferably 90% or more, and further preferably 95% or more) sequence similarity to the base sequence set forth in SEQ ID NO: 20 and can be used for detecting the fatty acid desaturase gene;
(i) an oligonucleotide having the base sequence set forth in SEQ ID NO: 21, an oligonucleotide having a base sequence set forth in SEQ ID NO: 21 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the fatty acid desaturase gene, or an oligonucleotide having a base sequence which has 80% or more (preferably 85% or more, more preferably 90% or more, and further preferably 95% or more) sequence similarity to the base sequence set forth in SEQ ID NO: 21 and can be used for detecting the fatty acid desaturase gene;
(j) an oligonucleotide having the base sequence set forth in SEQ ID NO: 22, an oligonucleotide having a base sequence set forth in SEQ ID NO: 22 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the fatty acid desaturase gene, or an oligonucleotide having a base sequence which has 80% or more (preferably 85% or more, more preferably 90% or more, and further preferably 95% or more) sequence similarity to the base sequence set forth in SEQ ID NO: 22 and can be used for detecting the fatty acid desaturase gene;
(k) an oligonucleotide having the base sequence set forth in SEQ ID NO: 23, an oligonucleotide having a base sequence set forth in SEQ ID NO: 23 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the fatty acid desaturase gene, or an oligonucleotide having a base sequence which has 80% or more (preferably 85% or more, more preferably 90% or more, and further preferably 95% or more) sequence similarity to the base sequence set forth in SEQ ID NO: 23 and can be used for detecting the fatty acid desaturase gene;
(l) an oligonucleotide having the base sequence set forth in SEQ ID NO: 24, an oligonucleotide having a base sequence set forth in SEQ ID NO: 24 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the fatty acid desaturase gene, or an oligonucleotide having a base sequence which has 80% or more (preferably 85% or more, more preferably 90% or more, and further preferably 95% or more) sequence similarity to the base sequence set forth in SEQ ID NO: 24 and can be used for detecting the fatty acid desaturase gene;
(m) an oligonucleotide having the base sequence set forth in SEQ ID NO: 25, an oligonucleotide having a base sequence set forth in SEQ ID NO: 25 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide)

which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 25 and can be used for detecting the β oxidation-related enzyme gene;

(n) an oligonucleotide having the base sequence set forth in SEQ ID NO: 26, an oligonucleotide having a base sequence set forth in SEQ ID NO: 26 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 26 and can be used for detecting the β oxidation-related enzyme gene;

(o) an oligonucleotide having the base sequence set forth in SEQ ID NO: 27, an oligonucleotide having a base sequence set forth in SEQ ID NO: 27 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 27 and can be used for detecting the β oxidation-related enzyme gene;

(p) an oligonucleotide having the base sequence set forth in SEQ ID NO: 28, an oligonucleotide having a base sequence set forth in SEQ ID NO: 28 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 28 and can be used for detecting the β oxidation-related enzyme gene;

(q) an oligonucleotide having the base sequence set forth in SEQ ID NO: 29, an oligonucleotide having a base sequence set forth in SEQ ID NO: 29 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 29 and can be used for detecting the β oxidation-related enzyme gene;

(r) an oligonucleotide having the base sequence set forth in SEQ ID NO: 30, an oligonucleotide having a base sequence set forth in SEQ ID NO: 30 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 30 and can be used for detecting the β oxidation-related enzyme gene;

(s) an oligonucleotide having the base sequence set forth in SEQ ID NO: 31, an oligonucleotide having a base sequence set forth in SEQ ID NO: 31 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 31 and can be used for detecting the β oxidation-related enzyme gene;

(t) an oligonucleotide having the base sequence set forth in SEQ ID NO: 32, an oligonucleotide having a base sequence set forth in SEQ ID NO: 32 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 32 and can be used for detecting the β oxidation-related enzyme gene;

(u) an oligonucleotide having the base sequence set forth in SEQ ID NO: 33, an oligonucleotide having a base sequence set forth in SEQ ID NO: 33 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 33 and can be used for detecting the β oxidation-related enzyme gene;

(v) an oligonucleotide having the base sequence set forth in SEQ ID NO: 34, an oligonucleotide having a base sequence set forth in SEQ ID NO: 34 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 34 and can be used for detecting the β oxidation-related enzyme gene;

(w) an oligonucleotide having the base sequence set forth in SEQ ID NO: 35, an oligonucleotide having a base sequence set forth in SEQ ID NO: 35 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 35 and can be used for detecting the β oxidation-related enzyme gene;

(x) an oligonucleotide having the base sequence set forth in SEQ ID NO: 36, an oligonucleotide having a base sequence set forth in SEQ ID NO: 36 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 36 and can be used for detecting the β oxidation-related enzyme gene;

(y) an oligonucleotide having the base sequence set forth in SEQ ID NO: 37, an oligonucleotide having a base sequence set forth in SEQ ID NO: 37 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 37 and can be used for detecting the β oxidation-related enzyme gene;

(z) an oligonucleotide having the base sequence set forth in SEQ ID NO: 38, an oligonucleotide having a base sequence set forth in SEQ ID NO: 38 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 38 and can be used for detecting the β oxidation-related enzyme gene;

(a1) an oligonucleotide having the base sequence set forth in SEQ ID NO: 39, an oligonucleotide having a base sequence set forth in SEQ ID NO: 39 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 39 and can be used for detecting the β oxidation-related enzyme gene;

(b1) an oligonucleotide having the base sequence set forth in SEQ ID NO: 40, an oligonucleotide having a base sequence set forth in SEQ ID NO: 40 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 40 and can be used for detecting the β oxidation-related enzyme gene;

(c1) an oligonucleotide having the base sequence set forth in SEQ ID NO: 41, an oligonucleotide having a base sequence set forth in SEQ ID NO: 41 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 41 and can be used for detecting the β oxidation-related enzyme gene; and (d1) an oligonucleotide having the base sequence set forth in SEQ ID NO: 42, an oligonucleotide having a base sequence set forth in SEQ ID NO: 42 with a substitution, deletion, insertion, or addition of 1 or several nucleotides (preferably 1 to 5 nucleotides, more preferably 1 to 4 nucleotides, further preferably 1 to 3 nucleotides, furthermore preferably 1 or 2 nucleotides, and particularly preferably 1 nucleotide) which can be used for detecting the β oxidation-related enzyme gene, or an oligonucleotide having a base sequence which has 80% or more (preferably 85% or more, more preferably 90% or more, and further preferably 95% or more) sequence similarity to the base sequence set forth in SEQ ID NO: 42 and can be used for detecting the β oxidation-related enzyme gene.

<2> The method described in the above item <1>, wherein the damp-dry malodor-causing substances are at least one kind of compound selected from 4M3H, 4-methyl-3-hexanoic acid, 5-methyl-2-hexanoic acid and 5-methyl-2-hexenoic acid; preferably 4M3H.

<3> The method described in the above item <1> or <2>, wherein the sebaceous dirt component is an anteiso fatty acid; preferably an anteiso fatty acid having 9 or more carbon atoms (preferably 11 or more carbon atoms, more preferably 17 or more carbon atoms) and 21 or less carbon atoms (preferably 19 or less carbon atoms); more preferably at least one kind of compound selected from 6-methyloctanoic acid, 8-methyldecanoic acid, 12-methyltetradecanoic acid, 14-methylhexadecanoic acid, 16-methyloctadecanoic acid, 14-methylhexadecenoic acid and 16-methyloctadecenoic acid, salts of these acids, and esters of these acids; and further preferably at least one kind of compound selected from 14-methylhexadecanoic acid and 16-methyloctadecanoic acid.

<4> The method described in any one of the above items <1> to <3>, wherein the fatty acid desaturase gene is at least one kind of gene selected from Δ9desaturase gene, Δ5desaturase gene and Δ6desaturase gene; and preferably Δ9desaturase gene.

<5> The method described in the above item <4>, wherein the base sequence of the Δ9desaturase gene is the base sequence set forth in SEQ ID NO: 1; a base sequence which has 70% or more (preferably 80% or more, more preferably 90% or more, still more preferably 95% or more, even more preferably 96.1% or more, even more preferably 97% or more, and particularly preferably 99% or more) sequence similarity to the base sequence set forth in SEQ ID NO: 1; a base sequence set forth in SEQ ID NO: 1 with a deletion, a substitution, an insertion, or an addition of 1 to 351 bases (preferably 1 to 234 bases, more preferably 1 to 117 bases, and particularly preferably 1 to 59 bases); or a complementary sequence thereof.

<6> The method described in the above item <4> or <5>, wherein the expression of the Δ9desaturase gene is detected by using at least one kind of oligonucleotide pair selected from the oligonucleotide pair containing the oligonucleotides (a) and (b), the oligonucleotide pair containing the oligonucleotides (c) and (d), the oligonucleotide pair containing the oligonucleotides (e) and (f), the oligonucleotide pair containing the oligonucleotides (g) and (h), the oligonucleotide pair containing the oligonucleotides (i) and (j), and the oligonucleotide pair containing the oligonucleotides (k) and (l).

<7> The method described in any one of the above items <1> to <3>, wherein the oxidation-related enzyme gene is at least one kind of gene selected from fadD gene, fadE gene, fadB gene and fadA gene; and preferably at least one kind of gene selected from fadB gene and fadD gene.

<8> The method described in the above item <7>, wherein the base sequence of the fadB gene is the base sequence set forth in SEQ ID NO: 5; a base sequence which has 70% or more (preferably 80% or more, more preferably 90% or more, still more preferably 95% or more, even more preferably 95.2% or more, even more preferably 97% or more, and particularly preferably 99% or more) sequence similarity to the base sequence set forth in SEQ ID NO: 5; a base sequence set forth in SEQ ID NO: 5 with a deletion, a substitution, an insertion, or an addition of 1 to 647 bases (preferably 1 to 431 bases, more preferably 1 to 216 bases, and particularly preferably 1 to 108 bases); or a complementary sequence thereof.

<9> The method described in the above item <7> or <8>, wherein the expression of the fadB gene is detected by using at least one kind of oligonucleotide pair selected from the oligonucleotide pair containing the oligonucleotides (m) and (n), the oligonucleotide pair containing the oligonucleotides (o) and (p), the oligonucleotide pair containing the oligonucleotides (q) and (r), and the oligonucleotide pair containing the oligonucleotides (s) and (t).

<10> The method described in the above item <7>, wherein the base sequence of the fadD gene is the base sequence set forth in SEQ ID NO: 9; a base sequence which has 70% or more (preferably 80% or more, more preferably 90% or more, still more preferably 95% or more, even more preferably 95.4% or more, even more preferably 97% or more, and particularly preferably 99% or more) sequence similarity to the base sequence set forth in SEQ ID NO: 9; a base sequence set forth in SEQ ID NO: 9 with a deletion, a substitution, an insertion, or an addition of 1 to 506 bases (preferably 1 to 377 bases, more preferably 1 to 169 bases, and particularly preferably 1 to 84 bases); or a complementary sequence thereof.

<11> The method described in the above item <7> or <10>, wherein the expression of the fadD gene is detected by using at least one kind of oligonucleotide pair selected from the oligonucleotide pair containing the oligonucleotides (u) and (v), the oligonucleotide pair containing the oligonucleotides (w) and (x), the oligonucleotide pair containing the oligonucleotides (y) and (z), the oligonucleotide pair containing the oligonucleotides (a1) and (b1), and the oligonucleotide pair containing the oligonucleotides (c1) and (d1).

<12> The method described in any one of the above items <1> to <11>, wherein the microorganisms are at least one kind of microbial strain selected from species of *Moraxella* sp. and *Moraxella osloensis*.

<13> The method described in the above item <12>, wherein the *Moraxella* sp. are microorganisms having 16S rRNA gene in which the base sequence of the 16S rRNA has a sequence similarity of 95% or more (preferably 97% or more, further preferably 98% or more, furthermore preferably 99% or more, and particularly preferably 99.2% or more) with the base sequence of SEQ ID NO: 43 or 44; or microorganisms which have 16S rRNA gene having a base sequence set forth in SEQ ID NO: 43 or 44 with a deletion, substitution, insertion, or addition of 1 to 75 bases (preferably 1 to 45 bases, more preferably 1 to 30 bases, and further preferably 1 to 15 bases).

<14> The method described in any one of the above items <1> to <13>, wherein the microorganisms and the test substance are added to a fabric product to which the sebaceous dirt component is clung, to bring the microorganisms and the test substance into contact with each other.

<15> The method described in the above item <14>, wherein the sebaceous dirt component is clung to the fabric product having a size of 2×2 cm at a proportion of from 0.1 mg or more and 1 mg or less.

<16> The method described in the above item <14> or <15>, wherein a microorganism suspension is added to a fabric product to obtain a microbial population of $10^2$ CFU/cm$^2$ or more and $10^5$ CFU/cm$^2$ or less.

<17> The method described in any one of the above items <14> to <16>, wherein the material of the fabric product is any one of wool, silk, cotton, polyester, polyamide and combinations thereof; preferably cotton.

<18> A method of screening a damp-dry malodor inhibitor, which contains selecting a test substance capable of reducing the expression amount of the at least one kind of gene, based on the method described in any one of the above items <1> to <17>.

<19> A method of detecting microorganisms which produce damp-dry malodor-causing substances, containing the steps of:

amplifying at least one kind of fragment of gene selected from a fatty acid desaturase gene and a β oxidation-related enzyme gene that are derived from microorganisms which produce damp-dry malodor-causing substances;

determining the presence or absence of an amplified fragment; and thereby detecting the microorganisms which produce damp-dry malodor-causing substances, wherein the detection of the microorganisms which produce damp-dry malodor-causing substances is performed by using at least one kind of oligonucleotide pair selected from an oligonucleotide pair containing the oligonucleotides (a) and (b) described above, an oligonucleotide pair containing the oligonucleotides (c) and (d) described above, an oligonucleotide pair containing the oligonucleotides (e) and (f) described above, an oligonucleotide pair containing the oligonucleotides (g) and (h) described above, an oligonucleotide pair containing the oligonucleotides (i) and (j) described above, an oligonucleotide pair containing the oligonucleotides (k) and (l) described above, an oligonucleotide pair containing the oligonucleotides (m) and (n) described above, an oligonucleotide pair containing the oligonucleotides (o) and (p) described above, an oligonucleotide pair containing the oligonucleotides (q) and (r) described above, an oligonucleotide pair containing the oligonucleotides (s) and (t) described above, an oligonucleotide pair containing the oligonucleotides (u) and (v) described above, an oligonucleotide pair containing the oligonucleotides (w) and (x) described above, an oligonucleotide pair containing the oligonucleotides (y) and (z) described above, an oligonucleotide pair containing the oligonucleotides (a1) and (b1) described above, and an oligonucleotide pair containing the oligonucleotides (c1) and (d1) described above.

<20> The method described in the above item <19>, wherein the damp-dry malodor-causing substances are at least one kind of compound selected from 4M3H, 4-methyl-3-hexanoic acid, 5-methyl-2-hexanoic acid and 5-methyl-2-hexenoic acid; preferably 4M3H.

<21> The method described in the above item <19> or <20>, wherein the fatty acid desaturase gene is at least one kind of gene selected from Δ9desaturase gene, Δ5desaturase gene and Δ6desaturase gene; and preferably Δ9desaturase gene.

<22> The method described in the above item <21>, wherein the base sequence of the Δ9desaturase gene is the base sequence set forth in SEQ ID NO: 1; a base sequence which has 70% or more (preferably 80% or more, more preferably 90% or more, still more preferably 95% or more, even more preferably 96.1% or more, even more preferably 97% or more, and particularly preferably 99% or more) sequence similarity to the base sequence set forth in SEQ ID NO: 1; a base sequence set forth in SEQ ID NO: 1 with a deletion, a substitution, an insertion, or an addition of 1 to 351 bases (preferably 1 to 234 bases, more preferably 1 to 117 bases, and particularly preferably 1 to 59 bases); or a complementary sequence thereof.

<23> The method described in the above item <21> or <22>, wherein a fragment of the Δ9desaturase gene is amplified by using at least one kind of oligonucleotide pair selected from the oligonucleotide pair containing the oligonucleotides (a) and (b), the oligonucleotide pair containing the oligonucleotides (c) and (d), the oligonucleotide pair containing the oligonucleotides (e) and (f), the oligonucleotide pair containing the oligonucleotides (g) and (h), the oligonucleotide pair containing the oligonucleotides (i) and (j), and the oligonucleotide pair containing the oligonucleotides (k) and (l).

<24> The method described in the above item <19> or <20>, wherein the β oxidation-related enzyme gene is at least one kind of gene selected from fadD gene, fadE gene, fadB gene and fadA gene; and preferably at least one kind of gene selected from fadB gene and fadD gene.

<25> The method described in the above item <24>, wherein the base sequence of the fadB gene is the base sequence set forth in SEQ ID NO: 5; a base sequence which has 70% or more (preferably 80% or more, more preferably 90% or more, still more preferably 95% or more, even more preferably 95.2% or more, even more preferably 97% or more, and particularly preferably 99% or more) sequence similarity to the base sequence set forth in SEQ ID NO: 5; a base sequence set forth in SEQ ID NO: 5 with a deletion, a substitution, an insertion, or an addition of 1 to 647 bases (preferably 1 to 431 bases, more preferably 1 to 216 bases, and particularly preferably 1 to 108 bases); or a complementary sequence thereof.

<26> The method described in the above item <24> or <25>, wherein a fragment of the fadB gene is amplified by using at least one kind of oligonucleotide pair selected from the oligonucleotide pair containing the oligonucleotides (m) and (n), the oligonucleotide pair containing the oligonucleotides (o) and (p), the oligonucleotide pair containing the oligonucleotides (q) and (r), and the oligonucleotide pair containing the oligonucleotides (s) and (t).

<27> The method described in the above item <24>, wherein the base sequence of the fadD gene is the base sequence set forth in SEQ ID NO: 9; a base sequence which has 70% or more (preferably 80% or more, more preferably 90% or more, still more preferably 95% or more, even more preferably 95.4% or more, even more preferably 97% or more, and particularly preferably 99% or more) sequence similarity to the base sequence set forth in SEQ ID NO: 9; a base sequence set forth in SEQ ID NO: 9 with a deletion, a substitution, an insertion, or an addition of 1 to 506 bases (preferably 1 to 377 bases, more preferably 1 to 169 bases, and particularly preferably 1 to 84 bases); or a complementary sequence thereof <28> The method described in the above item <24> or <27>, wherein a fragment of the fadD gene is amplified by using at least one kind of oligonucleotide pair selected from the oligonucleotide pair containing the oligonucleotides (u) and (v), the oligonucleotide pair containing the oligonucleotides (w) and (x), the oligonucleotide pair containing the oligonucleotides (y) and (z), the oligonucleotide pair containing the oligonucleotides (a1) and (b1), and the oligonucleotide pair containing the oligonucleotides (c1) and (d1).

<29> The method described in any one of the above items <19> to <28>, wherein the microorganisms are at least one kind of microbial strain selected from species of *Moraxella* sp. and *Moraxella osloensis*.

<30> The method described in the above item <29>, wherein the *Moraxella* sp. are microorganisms having 16S rRNA gene in which the base sequence of the 16S rRNA has a sequence similarity of 95% or more (preferably 97% or more, further preferably 98% or more, further preferably 99% or more, and particularly preferably 99.2% or more) with the base sequence of SEQ ID NO: 43 or 44; or microorganisms which have 16S rRNA gene having a base sequence set forth in SEQ ID NO: 43 or 44 with a deletion, substitution, insertion, or addition of 1 to 75 bases (preferably 1 to 45 bases, more preferably 1 to 30 bases, and further preferably 1 to 15 bases).

<31> An oligonucleotide selected from the above-described oligonucleotides (a) to (z) and (a1) to (d1); or an oligonucleotide pair selected from a pair of the above-described oligonucleotides (a) and (b), a pair of the above-described oligonucleotides (c) and (d), a pair of the above-described oligonucleotides (e) and (f), a pair of the above-described oligonucleotides (g) and (h), a pair of the above-described oligonucleotides (i) and (j), a pair of the above-described oligonucleotides (k) and (l), a pair of the above-described oligonucleotides (m) and (n), a pair of the above-described oligonucleotides (o) and (p), a pair of the above-described oligonucleotides (q) and (r), a pair of the above-described oligonucleotides (s) and (t), a pair of the above-described oligonucleotides (u) and (v), a pair of the above-described oligonucleotides (w) and (x), a pair of the above-described oligonucleotides (y) and (z), a pair of the above-described oligonucleotides (a1) and (b1), and a pair of the above-described oligonucleotides (c1) and (d1).

<32> The oligonucleotide or the oligonucleotide pair described in the above item <31>, wherein the oligonucleotide is a nucleic acid primer.

<33> The oligonucleotide or oligonucleotide pair described in the above item <32>, wherein the oligonucleotides (a) and (b), the oligonucleotides (c) and (d), the oligonucleotides (e) and (f), the oligonucleotides (g) and (h), the oligonucleotides (i) and (j), and the oligonucleotides (k) and (l) can function as nucleic acid primers for detecting expression of the fatty acid desaturase gene derived from microorganisms which produce damp-dry malodor-causing substances or for amplifying a gene fragment thereof by polymerase chain reaction (PCR).

<34> The oligonucleotide or the oligonucleotide pair described in the above item <33>, wherein the fatty acid desaturase gene is Δ9desaturase gene.

<35> The oligonucleotide or the oligonucleotide pair described in the above item <34>, wherein the base sequence of the Δ9desaturase gene is the base sequence set forth in SEQ ID NO: 1; a base sequence which has 70% or more (preferably 80% or more, more preferably 90% or more, still more preferably 95% or more, even more preferably 96.1% or more, even more preferably 97% or more, and particularly preferably 99% or more) sequence similarity to the base sequence set forth in SEQ ID NO: 1; a base sequence set forth in SEQ ID NO: 1 with a deletion, a substitution, an insertion, or an addition of 1 to 351 bases (preferably 1 to 234 bases, more preferably 1 to 117 bases, and particularly preferably 1 to 59 bases); or a complementary sequence thereof.

<36> The oligonucleotide or oligonucleotide pair described in the above item <32>, wherein the oligonucleotides (m) and (n), the oligonucleotides (o) and (p), the oligonucleotides (q) and (r), and the oligonucleotides (s) and (t) can function as nucleic acid primers for detecting expression of the β oxidation-related enzyme gene derived from microorganisms which produce damp-dry malodor-causing substances or for amplifying a gene fragment thereof by polymerase chain reaction (PCR).

<37> The oligonucleotide or the oligonucleotide pair described in the above item <36>, wherein the β oxidation-related enzyme gene is fadB gene.

<38> The oligonucleotide or the oligonucleotide pair described in the above item <37>, wherein the base sequence of the fadB gene is the base sequence set forth in SEQ ID NO: 5; a base sequence which has 70% or more (preferably 80% or more, more preferably 90% or more, still more preferably 95% or more, even more preferably 95.2% or more, even more preferably 97% or more, and particularly preferably 99% or more) sequence similarity to the base sequence set forth in SEQ ID NO: 5; a base sequence set forth in SEQ ID NO: 5 with a deletion, a substitution, an insertion, or an addition of 1 to 647 bases (preferably 1 to 431 bases, more preferably 1 to 216 bases, and particularly preferably 1 to 108 bases); or a complementary sequence thereof.

<39> The oligonucleotide or oligonucleotide pair described in the above item <32>, wherein the oligonucleotides (u) and (v), the oligonucleotides (w) and (x), the oligonucleotides (y) and (z), the oligonucleotides (a1) and (b1), and the oligonucleotides (c1) and (d1) can function as nucleic acid primers for detecting expression of the β oxidation-related enzyme gene derived from microorganisms which produce damp-dry malodor-causing substances or for amplifying a gene fragment thereof by polymerase chain reaction (PCR).

<40> The oligonucleotide or the oligonucleotide pair described in the above item <39>, wherein the β oxidation-related enzyme gene is fadD gene.

<41> The oligonucleotide or the oligonucleotide pair described in the above item <40>, wherein the base sequence of the fadD gene is the base sequence set forth in SEQ ID NO: 9; a base sequence which has 70% or more (preferably 80% or more, more preferably 90% or more, still more preferably 95% or more, even more preferably 95.4% or more, even more preferably 97% or more, and particularly preferably 99% or more) sequence similarity to the base sequence set forth in SEQ ID NO: 9; a base sequence set forth in SEQ ID NO: 9 with a deletion, a substitution, an insertion, or an addition of 1 to 506 bases (preferably 1 to 377 bases, more preferably 1 to 169 bases, and particularly preferably 1 to 84 bases); or a complementary sequence thereof.

<42> Use of the oligonucleotide pair containing any one of the oligonucleotides (a) and (b), the oligonucleotides (c) and (d), the oligonucleotides (e) and (f), the oligonucleotides (g) and (h), the oligonucleotides (i) and (j), and the oligonucleotides (k) and (l) as nucleic acid primers for detecting expression of the fatty acid desaturase gene derived from microorganisms which produce damp-dry malodor-causing substances or for amplifying a gene fragment thereof.

<43> Use of the oligonucleotide pair containing any one of the oligonucleotides (a) and (b), the oligonucleotides (c) and (d), the oligonucleotides (e) and (f), the oligonucleotides (g) and (h), the oligonucleotides (i) and (j), and the oligonucleotides (k) and (l) in the manufacture of nucleic acid primers for detecting expression of the fatty acid desaturase gene derived from microorganisms which produce damp-dry malodor-causing substances or for amplifying a gene fragment thereof.

<44> A method of using the oligonucleotide pair containing any one of the oligonucleotides (a) and (b), the oligonucleotides (c) and (d), the oligonucleotides (e) and (f), the oligonucleotides (g) and (h), the oligonucleotides (i) and (j), and the oligonucleotides (k) and (l) as nucleic acid primers for detecting expression of the fatty acid desaturase gene derived from microorganisms which produce damp-dry malodor-causing substances or for amplifying a gene fragment thereof.

<45> The use or method described in any one of the above items <42> to <44>, wherein the fatty acid desaturase gene is Δ9desaturase gene.

<46> The use or method described in the above item <45>, wherein the base sequence of the Δ9desaturase gene is the base sequence set forth in SEQ ID NO: 1; a base sequence which has 70% or more (preferably 80% or more, more preferably 90% or more, still more preferably 95% or more, even more preferably 96.1% or more, even more preferably 97% or more, and particularly preferably 99% or more) sequence similarity to the base sequence set forth in SEQ ID NO: 1; a base sequence set forth in SEQ ID NO: 1 with a deletion, a substitution, an insertion, or an addition of 1 to 351 bases (preferably 1 to 234 bases, more preferably 1 to 117 bases, and particularly preferably 1 to 59 bases); or a complementary sequence thereof.

<47> Use of the oligonucleotide pair containing any one of the oligonucleotides (m) and (n), the oligonucleotides (o) and (p), the oligonucleotides (q) and (r), and the oligonucleotides (s) and (t) as nucleic acid primers for detecting expression of the β oxidation-related enzyme gene derived from microorganisms which produce damp-dry malodor-causing substances or for amplifying a gene fragment thereof.

<48> Use of the oligonucleotide pair containing any one of the oligonucleotides (m) and (n), the oligonucleotides (o) and (p), the oligonucleotides (q) and (r), and the oligonucleotides (s) and (t) in the manufacture of nucleic acid primers for detecting expression of the β oxidation-related enzyme gene derived from microorganisms which produce damp-dry malodor-causing substances or for amplifying a gene fragment thereof.

<49> A method of using the oligonucleotide pair containing any one of the oligonucleotides (m) and (n), the oligonucleotides (o) and (p), the oligonucleotides (q) and (r), and the oligonucleotides (s) and (t) as nucleic acid primers for detecting expression of the β oxidation-related enzyme gene derived from microorganisms which produce damp-dry malodor-causing substances or for amplifying a gene fragment thereof.

<50> The use or method described in any one of the above items <47> to <49>, wherein the β oxidation-related enzyme gene is fadB gene.

<51> The use or method described in the above item <50>, wherein the base sequence of the fadB gene is the base sequence set forth in SEQ ID NO: 5; a base sequence which has 70% or more (preferably 80% or more, more preferably 90% or more, still more preferably 95% or more, even more preferably 95.2% or more, even more preferably 97% or more, and particularly preferably 99% or more) sequence similarity to the base sequence set forth in SEQ ID NO: 5; a base sequence set forth in SEQ ID NO: 5 with a deletion, a substitution, an insertion, or an addition of 1 to 647 bases (preferably 1 to 431 bases, more preferably 1 to 216 bases, and particularly preferably 1 to 108 bases); or a complementary sequence thereof.

<52> Use of the oligonucleotide pair containing any one of the oligonucleotides (u) and (v), the oligonucleotides (w) and (x), the oligonucleotides (y) and (z), the oligonucleotides (a1) and (b1), and the oligonucleotides (c1) and (d1) as nucleic acid primers for detecting expression of the β oxidation-related enzyme gene derived from microorganisms which produce damp-dry malodor-causing substances or for amplifying a gene fragment thereof.

<53> Use of the oligonucleotide pair containing any one of the oligonucleotides (u) and (v), the oligonucleotides (w) and (x), the oligonucleotides (y) and (z), the oligonucleotides (a1) and (b1), and the oligonucleotides (c1) and (d1) in the manufacture of nucleic acid primers for detecting expression of the β oxidation-related enzyme gene derived from microorganisms which produce damp-dry malodor-causing substances or for amplifying a gene fragment thereof.

<54> A method of using the oligonucleotide pair containing any one of the oligonucleotides (u) and (v), the oligonucleotides (w) and (x), the oligonucleotides (y) and (z), the oligonucleotides (a1) and (b1), and the oligonucleotides (c1) and (d1) as nucleic acid primers for detecting expression of the β oxidation-related enzyme gene derived from microorganisms which produce damp-dry malodor-causing substances or for amplifying a gene fragment thereof.

<55> The use or method described in any one of the above items <52> to <54>, wherein the β oxidation-related enzyme gene is fadD gene.

<56> The use or method described in the above item <55>, wherein the base sequence of the fadD gene is the base sequence set forth in SEQ ID NO: 9; a base sequence which has 70% or more (preferably 80% or more, more preferably 90% or more, still more preferably 95% or more, even more preferably 95.4% or more, even more preferably 97% or more, and particularly preferably 99% or more) sequence similarity to the base sequence set forth in SEQ ID NO: 9; a base sequence set forth in SEQ ID NO: 9 with a deletion, a substitution, an insertion, or an addition of 1 to 506 bases (preferably 1 to 377 bases, more preferably 1 to 169 bases, and particularly preferably 1 to 84 bases); or a complementary sequence thereof.

<57> A kit for evaluating inhibitory effect on damp-dry malodor or a kit for screening of a damp-dry malodor inhibitor, containing microorganisms which produce damp-dry malodor-causing substances, a sebaceous dirt component, and the oligonucleotide or the oligonucleotide pair described in any one of the above items <31> to <41>.

<58> A kit for detecting microorganisms which produce damp-dry malodor-causing substances, containing at least one kind of oligonucleotide or oligonucleotide pair described in any one of the above items <31> to <41>.

EXAMPLES

Hereinafter, the present invention will be described more in detail with reference to Examples, but it should be understood that the technological scope of the present invention is not particularly limited by the following Examples.

Production Example

14-Methylhexadecanoic acid was synthesized by a two-step reaction such as described below, according to JP-A-2009-149546.

Step (a)

11.9 g (60.0 mmol) of 12edodecanolide and 24.3 g (96.0 mmol, 1.6 equivalents) of a 32% (hydrogen bromide)/(acetic acid) solution were introduced into a 100-mL autoclave protected with Teflon (registered trademark), and the autoclave was purged with nitrogen and then sealed. The content in the autoclave was stirred with a magnetic stirrer for 16 hours by using an oil bath at 60° C. After cooling the mixture, 14 mL of water was added thereto, and the mixture was transferred into a separatory funnel by using 200 mL of hot hexane. The mixture was washed with ion-exchanged water, dried over magnesium sulfate, filtered, and crystallized from n-hexane. Thus, 14.4 g (yield: 86%) of 12-bromododecanoic acid was obtained.

Step (b)

Subsequently, in a 100-mL four-necked flask equipped with a refluxing cooling tube, a 50-mL separatory funnel, a magnetic stirrer, and a temperature sensor, 5.0 g (17.9 mmol) of 12-bromododecanoic acid and 28.2 mg (0.006 eq) of triphenylphosphine (manufactured by Kanto Chemical Co., Inc.) were introduced, and the mixture was dried under reduced pressure. In an argon atmosphere, 77.1 mg (0.03 equivalents) of copper(I) bromide (manufactured by Sigma-Aldrich Co.) and 10 mL of anhydrous tetrahydrofuran were added thereto. 39.5 mL (3 equivalents, 1.36N tetrahydrofuran solution) of 2-methylbutylmagnesium bromide was added dropwise thereto over one hour at room temperature. The mixture was stirred for one hour, and then 50 mL of a 1N aqueous solution of hydrochloric acid was added to the mixture, and the mixture was extracted two times with 100 mL of hexane. The extract was washed two times with 50 mL of ion-exchanged water, and then was dried over magnesium sulfate. The resultant was filtered and concentrated under reduced pressure, and 3.9 g of a crude product was obtained.

The crude product was quantitatively determined by gas chromatography (column: manufactured by Agilent Technologies, Inc., trade name: Ultra-2, 30 m×0.2 mm×0.33 μm, DET300° C., INJ300° C., column temperature: 100° C.→300° C., 10° C./min) using octadecane as an internal standard. As a result, the yield was found to be 79%.

In this manner, 14-methylhexadecanoic acid was obtained from 12-dodecanolide at a total yield of 68%. The purity was 98%.

16-Methyloctadecanoic acid was synthesized by the same operation, except that in the step (a) of the synthesis process for 14-methylhexadecanoic acid described above, 12-dodecanolide was changed to 15-pentadodecanolide, and in the step (b), 2-methylbutylmagnesium bromide was changed to sec-butylmagnesium bromide. Thus, 16-methyloctadecanoic acid was obtained from 15-pentadodecanolide at a total yield of 84%. The purity was 95%.

Test Example

Change in Expression of Δ9Desaturase Gene, fadB Gene and fadD Gene in the Presence of Sebaceous Dirt Component One platinum loop of precultured *Moraxella* sp. KMC4-1 was inoculated into 4 mL SCD liquid medium (manufactured by NIHON PHARMACEUTICAL CO., LTD) and cultured for 24 hours at 35° C. while shaking (160 rpm). To the cell liquid cultured for 24 hours, 10 mg of 16-methyloctadecanoic acid was added as a sebaceous dirt component. After culturing again for 6 hours at 35° C., the cells were collected. As a control, a system not added with a sebaceous dirt component was also cultured and cells were collected therefrom.

After RNA was stabilized by using RNA Protect Bacteria Reagent (manufactured by Qiagen), RNA was extracted from the collected cells using Rneasy Mini Kit (manufactured by Qiagen). DNase was removed from the extracted RNA using Dnase I (manufactured by Takara Bio Inc.), RNA concentration was adjusted to 20 ng/L, and reverse transcription was performed by using SupersprictIII (manufactured by Invitrogen) to prepare a template.

Based on the base sequence of the Δ9desaturase gene set forth in SEQ ID NO: 1, each of the primers having the nucleotide set forth in any one of SEQ ID NOS: 13 to 24 described in Table 7 was synthesized followed by purification by desalting.

TABLE 7

| Primer Name | SEQ ID NO: | Base sequence |
|---|---|---|
| des_F1 | SEQ ID NO: 13 | cgctgtgccatatgtttggt |
| des_R1 | SEQ ID NO: 14 | tgccaccatttgacgccat |
| des_F2 | SEQ ID NO: 15 | gatggtgggtgatattgcaggta |
| des_R2 | SEQ ID NO: 16 | atcggtataaggacgggtaccaa |
| des_F3 | SEQ ID NO: 17 | cccgtccttataccgataccaac |

TABLE 7-continued

| Primer Name | SEQ ID NO: | Base sequence |
|---|---|---|
| des_R3 | SEQ ID NO: 18 | ccattttacccattgcgatagt |
| des_F4 | SEQ ID NO: 19 | acccgtccttataccgataccaa |
| des_R4 | SEQ ID NO: 20 | ccattttacccattgcgatagt |
| des_F5 | SEQ ID NO: 21 | gatggtgggtgatattgcaggta |
| des_R5 | SEQ ID NO: 22 | cggtataaggacgggtaccaaac |
| des_F6 | SEQ ID NO: 23 | ggtatttgactggtgtgcaggac |
| des_R6 | SEQ ID NO: 24 | gcttgggtagttttgagcatcc |

Based on the base sequence of the β oxidation-related enzyme gene, the fadB gene set forth in SEQ ID NO: 5, and the base sequence of the β oxidation-related enzyme gene, the fadD gene set forth in SEQ ID NO: 9, each of the primers having the nucleotide set forth in any one of SEQ ID NOS: 25 to 32 (that is, for detection of the fadB gene) and the primers having the nucleotide set forth in any one of SEQ ID NOS: 33 to 42 (that is, for detection of the fadD gene) described in Table 8 was synthesized followed by purification by desalting.

TABLE 8

| Primer Name | SEQ ID NO: | Base sequence |
|---|---|---|
| fadB_F6 | SEQ ID NO: 25 | tgaaacggttcgctgtttagaag |
| fadB_R6 | SEQ ID NO: 26 | gaatcatttgtggcgcttcatag |
| fadB_F7 | SEQ ID NO: 27 | cgactacggtagcgttagcagaa |
| fadB_R7 | SEQ ID NO: 28 | catcaagtaagcaggacccattg |
| fadB_F8 | SEQ ID NO: 29 | ctttaagccgtatccgtcctacg |
| fadB_R8 | SEQ ID NO: 30 | ggcgctctagtaccgaagctaag |
| fadB_F9 | SEQ ID NO: 31 | cattcaaccgttttgaagacctg |
| fadB_R9 | SEQ ID NO: 32 | gataccgatgatacgtggcaaac |
| fadD_F1 | SEQ ID NO: 33 | cacattcccgctttaacagatca |
| fadD_R1 | SEQ ID NO: 34 | tgcgacgttatccacttctttgt |
| fadD_F2 | SEQ ID NO: 35 | cacattcccgctttaacagatca |
| fadD_R2 | SEQ ID NO: 36 | gtgcgacgttatccacttctttg |
| fadD_F3 | SEQ ID NO: 37 | accagcaatatggagcgagctat |
| fadD_R3 | SEQ ID NO: 38 | attaggcagcatgatagcgacac |
| fadD_F4 | SEQ ID NO: 39 | cgccttaccaaattgaccaaaag |
| fadD_R4 | SEQ ID NO: 40 | cggtgtattggataaaggcaaca |
| fadD_F5 | SEQ ID NO: 41 | cgagaattcaccagcaatatgga |
| fadD_R5 | SEQ ID NO: 42 | ttaggcagcatgatagcgacact |

By mixing 2 μL solution of the prepared template diluted ×20 with distilled sterile water, 12.5 μL of TaKaRa SYBR Premix EX Taq (trade name, manufactured by Takara Bio Inc.), 0.5 μL of the primer (des_F1, 20 pmol/L) containing the oligonucleotide having the base sequence set forth in SEQ ID NO: 13, 0.5 µL of the primer (des_R1, 20 pmol/L) containing the oligonucleotide having the base sequence set forth in SEQ ID NO: 14 and 9.5 µL of distilled sterile water, 25 µL reaction solution for real time PCR was prepared.

As a negative control, a PCR reaction solution, in which distilled sterile water was added instead of the DNA template, was prepared in the same manner as above.

Reaction solutions for real time PCR were prepared in the same manner as above, except that, instead of the primer set including the primer containing the oligonucleotide having the base sequence set forth in SEQ ID NO: 13 and the primer containing the oligonucleotide having the base sequence set forth in SEQ ID NO: 14, the primer set described in Tables 9 and 10 was used.

The reaction solutions for real time PCR each were subjected to a gene amplification by using an automatic gene amplification thermal cycler DICE Real time system II (manufactured by Takara Bio Inc.), and then the expression amount of each of the fatty acid desaturase gene (the Δ9desaturase gene) and the β oxidation-relating enzyme genes (the fadB gene and the fadD gene) was measured. PCR reaction conditions were 40 cycles of (i) a thermal denaturation reaction at 95° C. for 20 seconds, and (ii) an annealing reaction and an elongation reaction at 60° C. for 30 seconds.

For all primer sets tested, the change in gene expression amount when added with a sebaceous dirt component based on gene expression amount when not added with any sebaceous dirt component was calculated using 16S rRNA gene expression as an internal standard. A sample, in which the gene expression amount was at least two times the reference value, was rated as "A"; a sample, in which the gene expression amount was at least ½ times and less than two times the reference value, was rated as "B"; and a sample, in which the gene expression amount was less than ½ times the reference value, was rated as "C". The results are shown in Tables 9 and 10.

Further, the microbial cells obtained after culture were centrifuged (8000×g, 10 minutes), the supernatant was removed, and then the microbial cells were suspended in 5 mL of physiological saline. The suspension was centrifuged again (8000×g, 10 minutes), subsequently the supernatant was removed, and a microbial suspension was prepared by using physiological saline such that the $OD_{600}$ would be 1.0.

On a plain-woven cotton fabric which had been cut to a square having a size of 2 cm×2 cm, a solution prepared by dissolving 0.5 mg of 16-methyloctadecanoic acid that had been synthesized in the above production example in 0.1 mL of methanol was applied, and thereafter, methanol was dried to solid.

0.1 mL each of the various microbial suspensions described above was inoculated into the plain-woven cotton fabric described above, and the samples were left to stand still under humidified conditions at 37° C. for 24 hours. Sensory test of damp-dry malodor was performed by a professional panel who can distinguish different subjects based on damp-dry malodor.

In regard to the evaluation criteria, a sample from which a damp-dry malodor was perceived was rated as "A"; a sample from which a slight damp-dry malodor was perceived was rated as "B"; and a sample from which no damp-dry malodor was perceived was rated as "C". The results are shown in Tables 9 and 10.

TABLE 9

| | Combination of oligonucleotides (Upper row: Forward primer, Lower row: Reverse primer) | | | | | |
|---|---|---|---|---|---|---|
| | SEQ ID NO: 13 SEQ ID NO: 14 | SEQ ID NO: 15 SEQ ID NO: 16 | SEQ ID NO: 17 SEQ ID NO: 18 | SEQ ID NO: 19 SEQ ID NO: 20 | SEQ ID NO: 21 SEQ ID NO: 22 | SEQ ID NO: 23 SEQ ID NO: 24 |
| Sensory evaluation of damp-dry malodor | A | A | A | A | A | A |
| Change in gene expression amount | A | A | A | A | A | A |

TABLE 10

| | Combination of oligonucleotides (Upper row: Forward primer, Lower row: Reverse primer) | | | | |
|---|---|---|---|---|---|
| | SEQ ID NO: 25 SEQ ID NO: 26 | SEQ ID NO: 27 SEQ ID NO: 28 | SEQ ID NO: 29 SEQ ID NO: 30 | SEQ ID NO: 31 SEQ ID NO: 32 | SEQ ID NO: 33 SEQ ID NO: 34 |
| Sensory evaluation of damp-dry malodor | A | A | A | A | A |
| Change in gene expression amount | A | A | A | A | A |

| | Combination of oligonucleotides (Upper row: Forward primer, Lower row: Reverse primer) | | | |
|---|---|---|---|---|
| | SEQ ID NO: 35 SEQ ID NO: 36 | SEQ ID NO: 37 SEQ ID NO: 38 | SEQ ID NO: 39 SEQ ID NO: 40 | SEQ ID NO: 41 SEQ ID NO: 42 |
| Sensory evaluation of damp-dry malodor | A | A | A | A |
| Change in gene expression amount | A | A | A | A |

From the results shown in Tables 9 and 10, it was found that, in all primer sets for the Δ9desaturase gene, the fadB gene, and the fadD gene, each gene expression amount in a cloth having very strong damp-dry malodor increased by at least 2 times when a sebaceous dirt component was added compared to a case in which no sebaceous dirt component was added. Those results indicate that expression of each gene including the Δ9desaturase gene, the fadB gene and the fadD gene is involved with production of the damp-dry malodor-causing substances. Thus, by evaluating a change in gene expression amount of the Δ9desaturase gene, the fadB gene and the fadD gene, it is possible to perform evaluation of inhibitory effect on damp-dry malodor and screening of a damp-dry malodor inhibitor.

Example 1: Determination of Change in Expression of Δ9Desaturase Gene, fadB Gene and fadD Gene, Growth-Inhibitory and Bactericidal Effect, in the Presence of Test Substance The substances (1) to (7) described below each were added to 4 mL SCD liquid medium (manufactured by NIHON PHARMACEUTICAL CO., LTD). As a control, a medium system not added with any test substance was also prepared. To these medium, one platinum loop of precultured *Moraxella* sp. KMC4-1 was inoculated and cultured for 24 hours at 35 C while shaking (160 rpm).

To the cell liquid cultured for 24 hours, 10 mg of 16-methyloctadecanoic acid was added as a sebaceous dirt component. After culturing again for 6 hours at 35° C., the cells were collected. As a control, a system not added with a sebaceous dirt component was also cultured and cells were collected therefrom.

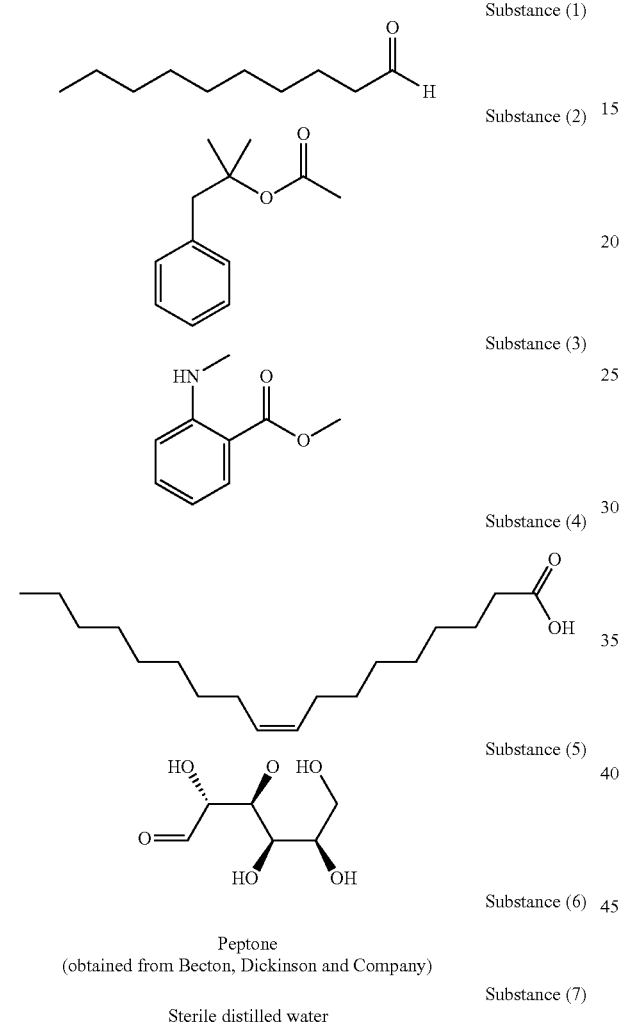

Substance (1)

Substance (2)

Substance (3)

Substance (4)

Substance (5)

Substance (6)

Peptone
(obtained from Becton, Dickinson and Company)

Substance (7)

Sterile distilled water

An RNA sample was prepared from the collected cells in the same manner as in the test example 1.

By mixing 2 μL solution of the prepared template diluted ×20 with distilled sterile water, 12.5 μL of TaKaRa SYBR Premix EX Taq (trade name, manufactured by Takara Bio Inc.), 0.5 μL of the primer (des_F1, 20 pmol/L) containing the oligonucleotide having the base sequence set forth in SEQ ID NO: 13, 0.5 μL of the primer (des_R1, 20 pmol/L) containing the oligonucleotide having the base sequence set forth in SEQ ID NO: 14 and 9.5 μL of distilled sterile water, 25 μL reaction solution for real time PCR was prepared.

As a negative control, a PCR reaction solution, in which distilled sterile water was added instead of the DNA template, was prepared in the same manner as above.

Reaction solutions for real time PCR were prepared in the same manner as above, except that, instead of the primer set including the primer containing the oligonucleotide having the base sequence set forth in SEQ ID NO: 13 and the primer containing the oligonucleotide having the base sequence set forth in SEQ ID NO: 14, the primer set described in Tables 11 to 13 was used.

The reaction solutions for real time PCR each were subjected to a gene amplification by using an automatic gene amplification thermal cycler DICE Real time system II (manufactured by Takara Bio Inc.), and then the expression amount of each of the fatty acid desaturase gene (the Δ9desaturase gene) and the β oxidation-relating enzyme genes (the fadB gene and the fadD gene) was measured. PCR reaction conditions were 40 cycles of (i) a thermal denaturation reaction at 95° C. for 20 seconds, and (ii) an annealing reaction and an elongation reaction at 60° C. for 30 seconds.

By having the gene expression of 16S rRNA as an internal standard, and having the gene expression amount when adding no sebaceous dirt component and no test substance as a reference value, change in expression amount of each gene was calculated relative to the reference value. A sample, in which the expression amount of the gene was ½ times or less the reference value, was rated as "A"; a sample, in which the expression amount of the gene was more than ½ times and ⅔ times or less the reference value, was rated as "B"; and a sample, in which the expression amount of the gene was more than ⅔ times the reference value, was rated as "C". The results are shown in Tables 11 to 13.

TABLE 11

Change in the expression amount of Δ9desaturase gene

| | Combination of oligonucleotides (Upper row: Forward primer, Lower row: Reverse primer) | | | | | |
|---|---|---|---|---|---|---|
| Test substance | SEQ ID NO: 13 SEQ ID NO: 14 | SEQ ID NO: 15 SEQ ID NO: 16 | SEQ ID NO: 17 SEQ ID NO: 18 | SEQ ID NO: 19 SEQ ID NO: 20 | SEQ ID NO: 21 SEQ ID NO: 22 | SEQ ID NO: 23 SEQ ID NO: 24 |
| Substance (1) 10 ppm | B | B | A | A | B | B |
| Substance (2) 100 ppm | C | B | B | B | C | C |
| Substance (3) 100 ppm | C | C | C | C | C | C |
| Substance (4) 500 ppm | C | C | C | C | C | C |
| Substance (5) 100 ppm | C | C | C | C | C | C |
| Substance (6) 100 ppm | C | C | C | C | C | C |
| Sterile distilled water | C | C | C | C | C | C |

TABLE 12

Change in the expression amount of fadB gene

| | Combination of oligonucleotides (Upper row: Forward primer, Lower row: Reverse primer) | | | |
|---|---|---|---|---|
| Test substance | SEQ ID NO: 25 SEQ ID NO: 26 | SEQ ID NO: 27 SEQ ID NO: 28 | SEQ ID NO: 29 SEQ ID NO: 30 | SEQ ID NO: 31 SEQ ID NO: 32 |
| Substance (1) 10 ppm | C | C | C | C |
| Substance (2) 100 ppm | A | A | A | A |

TABLE 12-continued

Change in the expression amount of fadB gene

| Test substance | Combination of oligonucleotides (Upper row: Forward primer, Lower row: Reverse primer) | | | |
|---|---|---|---|---|
| | SEQ ID NO: 25 SEQ ID NO: 26 | SEQ ID NO: 27 SEQ ID NO: 28 | SEQ ID NO: 29 SEQ ID NO: 30 | SEQ ID NO: 31 SEQ ID NO: 32 |
| Substance (3) 100 ppm | A | A | A | B |
| Substance (4) 500 ppm | A | A | A | A |
| Substance (5) 100 ppm | C | C | C | C |
| Substance (6) 100 ppm | C | C | C | C |
| Sterile distilled water | C | C | C | C |

TABLE 13

Change in the expression amount of fadD gene

| Test substance | Combination of oligonucleotides (Upper row: Forward primer, Lower row: Reverse primer) | |
|---|---|---|
| | SEQ ID NO: 35 SEQ ID NO: 36 | SEQ ID NO: 41 SEQ ID NO: 42 |
| Substance (1) 10 ppm | A | A |
| Substance (2) 100 ppm | A | A |
| Substance (3) 100 ppm | A | A |
| Substance (4) 500 ppm | C | C |
| Substance (5) 100 ppm | C | C |
| Substance (6) 100 ppm | C | C |
| Sterile distilled water | C | C |

Subsequently, by using *Moraxella* sp. KMC4-1, which is one kind of the microorganisms which produce damp-dry malodor-causing substances, sensory evaluation of the inhibitory effect on damp-dry malodor by the test substance and measurement of production amount of 4M3H as one kind of the damp-dry malodor-causing substances were carried out.

*Moraxella* sp. KMC4-1 was inoculated as a test microbe onto SCD-LP agar medium (manufactured by Wako Pure Chemical Industries, Ltd.) and cultured for 1 to 2 weeks at room temperature to give a pre-culture plate. Colony surface was scraped off from the pre-culture plate, suspended in 5 mL of physiological saline, and $OD_{600}$ was adjusted to 1.0 (about $10^8$ CFU/mL).

A cotton jersey cloth obtained in a constant state after sterilization and drying at 25° C., 40% RH (cotton jersey manufactured by Shikisensha Colo., LTD., without silket finish) was cut to a square of 2 cm×2 cm. To the cloth, a solution prepared by dissolving 0.5 mg of 14-methylhexadecanoic acid, as a sebaceous dirt component, in 0.1 mL methanol, was applied. Then, methanol was dried to solid, to give a model examination cloth.

Methanol solution was prepared for each test substance and applied at 20° C. on the model examination cloth such that applied amount of each test substance was 10 g per gram of the model examination cloth. It was then dried for 2 hours at room temperature to dry methanol. Thereafter, 0.1 mL of the microbe suspension was coated onto the model examination cloth, and cultured for 24 hours in a petri dish using an incubator at 37° C. with relative humidity of 70%, to obtain a microbe-fixed cloth.

The sensory test of the model examination cloth was evaluated by a professional panel who can distinguish different subjects based on the damp-dry malodor. A sample, in which an inhibitory effect on damp-dry malodor was confirmed, was rated as "A"; a sample, in which it was difficult to determine the inhibitory effect on damp-dry malodor or a Weak inhibitory effect on damp-dry malodor was confirmed, was rated as "B; and a sample, in which no inhibitory effect on damp-dry malodor was confirmed, was rated as "C". The results are shown in Table 14.

Further, the model examination cloth was analyzed by using LC-FL (liquid chromatography apparatus: HITACHI ELITE LaChrom (trade name, manufactured by Hitachi, Ltd.), column: Lichrosphere 100 RP-8(e) (trade name, manufactured by Agilent Technologies, Inc., 5 μm×125 mm×4 mmφ), column temperature: 40° C., eluent: a mixed solution of acetonitrile/water=7/3 (volume ratio), flow rate: 1.0 mL/min, detector: excitation wavelength (365 nm), measurement wavelength (412 nm)), and thereby quantification of 4M3H thus produced in the model examination cloth was carried out. Ratio of the produced 4M3H amount relative to the 4M3H production amount when no test substance was added was calculated, and then ratio of suppressing 4M3H production was calculated. The results are shown in Table 14.

TABLE 14

| Test substance | Sensory evaluation results | Ratio of suppressing 4M3H production |
|---|---|---|
| Substance (1) 10 ppm | A | 100% |
| Substance (2) 100 ppm | A | 100% |
| Substance (3) 100 ppm | A | 91% |
| Substance (4) 500 ppm | A | 81% |
| Substance (5) 100 ppm | C | 0% |
| Substance (6) 100 ppm | B | 0% |
| Sterile distilled water | C | 0% |

From the results shown in Table 11, it was found that, among the test substance used for the test, by contacting the substance (1) with microorganisms which produce damp-dry malodor-causing substances, the expression amount of the Δ9desaturase gene by the microorganisms was decreased. Moreover, from the results shown in Table 12, it was found that, by contacting the substance (2), the substance (3) or the substance (4) with microorganisms which produce damp-dry malodor-causing substances, the expression amount of the fadB gene by the microorganisms was decreased. Moreover, from the results shown in Table 13, it was found that, by contacting the substance (1), the substance (2) or the substance (3) with microorganisms which produce damp-dry malodor-causing substances, the expression amount of the fadD gene by the microorganisms was decreased.

Meanwhile, as shown in the results of Table 14, when the substance (1), the substance (2), the substance (3) or the substance (4) was brought into contact with *Moraxella* sp. KMC4-1, which is one kind of microorganisms which produce damp-dry malodor-causing substances, an inhibitory effect on damp-dry malodor was observed and also the 4M3H production inhibition ratio was high. Thus, it was found that, by inhibiting the gene expression of an enzyme relating to the production of the damp-dry malodor-causing substances, the production of damp-dry malodor-causing substances such as 4M3H is prevented and thus an occurrence of a damp-dry malodor is suppressed.

Based on the results shown above, it can be said that the expression of the fatty acid desaturase gene and/or the β oxidation-related enzyme gene of the microorganisms which produce damp-dry malodor-causing substances is related to an occurrence of a damp-dry malodor.

Next, growth-inhibitory and a bactericidal effect of the substances (1) to (7) against the microorganisms which produce damp-dry malodor-causing substances were determined.

(Growth-Inhibitory)

To 4 mL of SCD liquid medium (manufactured by NIHON PHARMACEUTICAL CO., LTD), the substances (1) to (7) each were added so as to be the final concentration described in Table 15. As a control, a medium system not added with any test substance was also prepared. To the medium, the precultured Moraxella sp. KMC4-1 was inoculated so as to be the initial concentration of $10^4$ CFU/mL and cultured for 24 hours at 35° C. while shaking (160 rpm). After that, it was subjected to serial dilution using LP dilution solution (NIHON PHARMACEUTICAL CO., LTD). Then, by using SCD-LP agar medium (NIHON PHARMACEUTICAL CO., LTD), the number of bacteria remained alive was determined.

(Bactericidal Test)

To 5 mL of a test solution in which the substances (1) to (7) each were added so as to be the final concentration described in Table 15, the precultured Moraxella sp. KMC4-1 was inoculated so as to be the concentration of $10^6$ CFU/mL and cultured for 2 hours at 25° C. while shaking (160 rpm). After that, it was subjected to serial dilution using LP dilution solution (NIHON PHARMACEUTICAL CO., LTD). Then, by using SCD-LP agar medium (NIHON PHARMACEUTICAL CO., LTD), the number of bacteria remained alive was determined.

As for the growth-inhibitory and the bactericidal effect, the evaluation was made as follows: compared to the control, when there was the bacteria number decrease of log 3 or more, it was rated as "A"; when there was the bacteria number decrease of log 1 or more but less than log 3, it was rated as "B"; and when there was the bacteria number decrease of less than log 1, it was rated as "C". The results are shown in Table 15.

TABLE 15

| Test substance | Growth-inhibitory effect | Bactericidal effect |
| --- | --- | --- |
| Substance (1) 10 ppm | C | C |
| Substance (2) 100 ppm | B(log2) | C |
| Substance (3) 100 ppm | C | C |
| Substance (4) 500 ppm | B(log2) | C |
| Substance (5) 100 ppm | C | C |
| Substance (6) 100 ppm | C | C |
| Sterile distilled water | C | C |

From the results shown in Table 15, it was found that the substances (1) to (4) having an effect of suppressing occurrence of a damp-dry malodor were not observed to have any one of the growth-inhibitory effect and the bactericidal effect against Moraxella sp. KMC4-1.

As shown above, according to the present invention, it is possible to perform screening or evaluation of not only a damp-dry malodor inhibitor which exhibits a growth-inhibitory effect or a bactericidal effect against the microorganisms which produce damp-dry malodor-causing substances but also a damp-dry malodor inhibitor which expresses an effect of suppressing metabolism related to production of damp-dry malodor-causing substances such as 4M3H.

Example 2 Detection of Microorganisms which Produce Damp-Dry Malodor-Causing Substances from Bacterial Cells (1) Preparation of Genomic DNA Each strain of genus Moraxella and various microbes described in Table 16 was inoculated to SCD agar medium (manufactured by NIHON PHARMACEUTICAL CO., LTD). After culture for 24 hours at 35° C., microbial cells were collected from the agar medium using a platinum loop. Genomic DNA solutions were prepared from the collected microbial cells using a genomic DNA preparation kit (Prep-Man ultra Reagent (trade name) manufactured by Applied Biosystems).

Furthermore, in regard to the Moraxella bacteria, the sequence similarity of the base sequence in the 16S rRNA gene of each bacterium with the base sequence set forth in SEQ ID NO: 43 or SEQ ID NO: 44 was determined. Meanwhile, the base sequences set forth in SEQ ID NO: 43 and SEQ ID NO: 44 represent the base sequences of the 16S rRNA gene of Moraxella sp. 4-1 and Moraxella osloensis ATCC19976, respectively. Furthermore, the sequence similarity of the base sequences was calculated by using a genetic information processing software, Clustal W.

(2) Quantification of produced 4M3H

One platinum loop of each of various microbial strains of genus Moraxella and various microbes described in Table 16 was inoculated into 5 mL of a SCD liquid medium (manufactured by Nihon Pharmaceutical Co., Ltd.), and the microbial cells were subjected to shaking culture (160 rpm) at 35° C. for 24 hours. The microbial cells obtained after culture were centrifuged (8000×g, 10 minutes), the supernatant was removed, and then the microbial cells were suspended in 5 mL of physiological saline. The suspension was centrifuged again (8000×g, 10 minutes), subsequently the supernatant was removed, and a microbial suspension was prepared by using physiological saline such that the $OD_{600}$ would be 1.0.

On a plain-woven cotton fabric which had been cut to a square having a size of 2 cm×2 cm, a solution prepared by dissolving 0.5 mg of 16-methyloctadecanoic acid in 0.1 mL of methanol was applied, and thereafter, methanol was dried to solid.

0.1 mL each of the various microbial suspensions described above was inoculated into the plain-woven cotton fabric described above, and the samples were left to stand still under humidified conditions at 37° C. for 24 hours. Thus, quantification of 4M3H was carried out in the following manner.

10 mL of methanol was added to the towel that had been left to stand still for 24 hours, and 1 mL of the methanol was mixed with 1 mL of ADAM (9-anthrydiazomethanene, manufactured by Funakoshi Corp., 0.1 w/v %). The mixture was left to stand for 60 minutes at room temperature, and thus derivatization was carried out.

Thereafter, 10 μL of the solution was analyzed by using LC-FL (liquid chromatography apparatus: HITACHI ELITE LaChrom (trade name, manufactured by Hitachi, Ltd.), column: Lichrosphere 100 RP-8(e) (trade name, manufactured by Agilent Technologies, Inc., 5 μm×125 mm×4 mmφ), column temperature: 40° C., eluent: a mixed solution of acetonitrile/water=7/3 (volume ratio), flow rate: 1.0 mL/min, detector: excitation wavelength (365 nm), measurement wavelength (412 nm)), and thereby quantification of 4M3H thus produced was carried out. In regard to the amount of the produced 4M3H, a sample, in which the produced 4M3H amount was more than 1 μg, was rated as "A"; a sample, in which the produced 4M3H amount was more than 0.1 μg and 1 μg or less, was rated as "B"; a sample, in which the produced 4M3H amount was more than 0 μg and 0.1 μg or less, was rated as "C"; and a sample, in which no 4M3H was detected, was rated as "D". The results are shown in Table 16.

denaturation reaction at 98° C. for 10 seconds, (ii) an annealing reaction at 60° C. for 30 seconds, and (iii) an elongation reaction at 72° C. for 1 minute.

(4) Agarose Gel Electrophoresis

After PCR, the reaction solution was applied to 2% agarose gel and electrophoresed for 30 minutes with 100 V in TBA buffer. Gel was then taken out and immersed for 30 minutes in a SYBR safe DNA gel stain in 1×TAE solution

TABLE 16

| No. | Microbial strain | | Sequence similarity with the base sequence set forth in SEQ ID NO: 43 | | Sequence similarity with the base sequence set forth in SEQ ID NO: 44 | | Produced 4M3H amount |
|---|---|---|---|---|---|---|---|
| | | | Upstream 504 bp | 1484 bp | Upstream 504 bp | 1484 bp | |
| 4-2 | Moraxella osloensis | ATCC19976 | 99.2 | 99.3 | 100 | 100 | A |
| 4-8 | Moraxella sp. | KMC4-1 (isolated strain) | 100 | 100 | 99.2 | 99.3 | A |
| 4-9 | Moraxella sp. | KMC4-3 (isolated strain) | 100 | — | 99.2 | — | A |
| 4-10 | Moraxella sp. | KMC4-4 (isolated strain) | 99.2 | 99.7 | 100 | 99.7 | A |
| 4-11 | Moraxella sp. | KMC4-5 (isolated strain) | 100 | — | 99.4 | — | A |
| 4-12 | Moraxella sp. | KMC4-6 (isolated strain) | 100 | — | 99.8 | — | A |
| 4-13 | Moraxella sp. | KMC4-7 (isolated strain) | 99.8 | — | 99.2 | — | A |
| 4-14 | Moraxella sp. | KMC4-8 (isolated strain) | 100 | — | 99.2 | — | A |
| 4-15 | Moraxella sp. | KMC4-9 (isolated strain) | 99.8 | — | 99.8 | — | A |
| 4-16 | Moraxella sp. | KMC4-10 (isolated strain) | 100 | — | 99.4 | — | A |
| 4-17 | Moraxella sp. | KMC4-11 (isolated strain) | 100 | — | 99.4 | — | A |
| 4-18 | Moraxella sp. | KMC4-12 (isolated strain) | 100 | — | 99.2 | — | A |
| 4-19 | Pseudomonas aeruginosa | NBRC13275 | — | — | — | — | D |
| 4-20 | Enterobacter cloacae | NBRC3320 | — | — | — | — | D |

From the results shown in Table 16, 4M3H production was confirmed in all the strains of *Moraxella osloensis* and *Moraxella* sp. that are used for the test. To the contrary, no 4M3H production was confirmed in the *Pseudomonas aeruginosa* NBRC13275 and *Enterobacter cloacae* NBRC3320.

(3) PCR Reaction

By mixing 1 μL solution of the prepared genomic DNA template diluted×100 with distilled sterile water, 0.1 μL of TaKaRa EX Taq HS (trade name, manufactured by Takara Bio Inc.), 1.6 μl of the mixture of four deoxyribonucleotide triphosphate (dNTP) (dNTP mixture liquid attached to TaKaRa EX Taq Hot Start Version (trade name) manufactured by Takara Bio Inc.), 2 μL of 10× conc. reaction buffer (buffer attached to TaKaRa EX Taq Hot Start Version (trade name) manufactured by Takara Bio Inc.), 0.4 μL of the primer (des_F1, 20 pmol/L) containing the oligonucleotide having the base sequence set forth in SEQ ID NO: 13, 0.4 μL of the primer (des_R1, 20 pmol/L) containing the oligonucleotide having the base sequence set forth in SEQ ID NO: 14, and 14.5 μL of distilled sterile water, 20 μL PCR reaction solution was prepared.

As a negative control, a PCR reaction solution, in which distilled sterile water was added instead of the DNA template, was prepared in the same manner as above.

PCR reaction solutions were prepared in the same manner as above, except that, instead of the primer set of the primer containing the oligonucleotide having the base sequence set forth in SEQ ID NO: 13 and the primer containing the oligonucleotide having the base sequence set forth in SEQ ID NO: 14, the primer set described in Tables 17 to 19 was used.

The PCR reaction solution was subjected to a gene amplification treatment using an automatic gene amplification device thermal cycler DICE (TAKARA BIO INC.). PCR reaction conditions were 30 cycles of (i) a thermal (manufactured by Invitrogen) for staining DNA fragments, which were than photographed by Polaroid (registered trademark) camera under UV lamp radiation to see the presence or absence of DNA fragment having a size of about 120 bp. The DNA fragment size was determined by relative mobility compared to DNA fragments with known base pair number, which have been also electrophoresed with the DNA in interest. Determination result of a target gene fragment is shown in Tables 17 to 19.

TABLE 17

| Combination of oligonucleotides | | Results | | | | | |
|---|---|---|---|---|---|---|---|
| Forward primer | Reverse primer | Moraxella osloensis ATCC19976 | Moraxella sp. | | | | |
| | | | KMC 4-1 | KMC 4-3 | KMC 4-4 | KMC 4-5 | KMC 4-6 |
| SEQ ID NO: 13 | SEQ ID NO: 14 | Y | Y | Y | Y | Y | Y |
| SEQ ID NO: 15 | SEQ ID NO: 16 | Y | Y | Y | Y | Y | Y |
| SEQ ID NO: 17 | SEQ ID NO: 18 | Y | Y | Y | Y | Y | Y |
| SEQ ID NO: 19 | SEQ ID NO: 20 | Y | Y | Y | Y | Y | Y |
| SEQ ID NO: 21 | SEQ ID NO: 22 | Y | Y | Y | Y | Y | Y |
| SEQ ID NO: 23 | SEQ ID NO: 24 | Y | Y | Y | Y | Y | Y |
| Sterile distilled water | Sterile distilled water | N | N | N | N | N | N |

Y: Gene fragment was amplified.
N: Gene fragment was not amplified.

TABLE 18

| Combination of oligonucleotides | | Results *Moraxella* sp. | | | | | |
|---|---|---|---|---|---|---|---|
| Forward primer | Reverse primer | KMC 4-7 | KMC 4-8 | KMC 4-9 | KMC 4-10 | KMC 4-11 | KMC 4-12 |
| SEQ ID NO: 13 | SEQ ID NO: 14 | Y | Y | Y | Y | Y | Y |
| SEQ ID NO: 15 | SEQ ID NO: 16 | Y | Y | Y | Y | Y | Y |
| SEQ ID NO: 17 | SEQ ID NO: 18 | Y | Y | Y | Y | Y | Y |
| SEQ ID NO: 19 | SEQ ID NO: 20 | Y | Y | Y | Y | Y | Y |
| SEQ ID NO: 21 | SEQ ID NO: 22 | Y | Y | Y | Y | Y | Y |
| SEQ ID NO: 23 | SEQ ID NO: 24 | Y | Y | Y | Y | Y | Y |
| Sterile distilled water | Sterile distilled water | N | N | N | N | N | N |

Y: Gene fragment was amplified.
N: Gene fragment was not amplified.

TABLE 19

| Combination of oligonucleotides | | Results | |
|---|---|---|---|
| Forward primer | Reverse primer | *Pseudomonas aeruginosa* NBRC13275 | *Enterobacter cloacae* NBRC3320 |
| SEQ ID NO: 13 | SEQ ID NO: 14 | N | N |
| SEQ ID NO: 15 | SEQ ID NO: 16 | N | N |
| SEQ ID NO: 17 | SEQ ID NO: 18 | N | N |
| SEQ ID NO: 19 | SEQ ID NO: 20 | N | N |
| SEQ ID NO: 21 | SEQ ID NO: 22 | N | N |
| SEQ ID NO: 23 | SEQ ID NO: 24 | N | N |
| Sterile distilled water | Sterile distilled water | N | N |

N: Gene fragment was not amplified.

As shown in Tables 17 and 18, the Δ9desaturase gene, which is one kind of fatty acid desaturase gene, was identified in various bacterial strains of genus *Moraxella*, which is one kind of damp-dry malodor-causing bacteria. Meanwhile, as shown in Table 19, in the sample containing genomic DNA of the microorganisms which do not produce damp-dry malodor-causing substances, the gene fragment was not identified. Thus, it is found that the microorganisms which produce damp-dry malodor-causing substances can be detected quickly and accurately by using a specific oligonucleotide pair.

Further, with regard to the *Moraxella* sp. KMC4-1, the sequence similarity between base sequence of the gene fragment which has been amplified by using each primer pair and the base sequence set forth in SEQ ID NO: 1 is shown in Table 20.

TABLE 20

| Combination of oligonucleotides | | Sequence similarity to the base sequence set forth in SEQ ID NO: 1 |
|---|---|---|
| Forward primer | Reverse primer | |
| SEQ ID NO: 13 | SEQ ID NO: 14 | 96.1% |
| SEQ ID NO: 15 | SEQ ID NO: 16 | 98.4% |
| SEQ ID NO: 17 | SEQ ID NO: 18 | 98.4% |
| SEQ ID NO: 19 | SEQ ID NO: 20 | 98.4% |
| SEQ ID NO: 21 | SEQ ID NO: 22 | 98.4% |
| SEQ ID NO: 23 | SEQ ID NO: 24 | 96.9% |

As shown in Table 20, each of the base sequence of the amplified gene fragment has sequence similarity of 95% or more to the base sequence of the Δ9desaturase gene set forth in SEQ ID NO: 1.

Based on these results, it was found that the fatty acid desaturase gene fragments of microorganisms which produce damp-dry malodor-causing substances can be amplified by using the oligonucleotide of the present invention. Therefore, the fatty acid desaturase gene can be detected quickly and accurately.

Example 3 Detection of Microorganisms which Produce Damp-Dry Malodor-Causing Substances from Bacterial Cells (1) PCR Reaction By mixing 1 μL solution of the genomic DNA prepared in Example 2 diluted×100 with distilled sterile water, 0.1 μL of TaKaRa EX Taq HS (trade name, manufactured by Takara Bio Inc.), 1.6 μL of the mixture of four deoxyribonucleotide triphosphate (dNTP) (dNTP mixture liquid attached to TaKaRa EX Taq Hot Start Version (trade name) manufactured by Takara Bio Inc.), 2 μL of 10× conc. reaction buffer (buffer attached to TaKaRa EX Taq Hot Start Version (trade name) manufactured by Takara Bio Inc.), 0.4 μL of the primer (fadB_F6, 20 pmol/L) containing the oligonucleotide having the base sequence set forth in SEQ ID NO: 25, 0.4 μL of the primer (fadB_R6, 20 pmol/L) containing the oligonucleotide having the base sequence set forth in SEQ ID NO: 26, and 14.5 μL of distilled sterile water, 20 μL PCR reaction solution was prepared.

As a negative control, a PCR reaction solution, in which distilled sterile water was added instead of the DNA template, was prepared in the same manner as above.

PCR reaction solutions were prepared in the same manner as above, except that, instead of the primer set of the primer containing the oligonucleotide having the base sequence set forth in SEQ ID NO: 25 and the primer containing the oligonucleotide having the base sequence set forth in SEQ ID NO: 26, the primer set described in Tables 21 to 23 was used.

The PCR reaction solution was subjected to a gene amplification treatment using an automatic gene amplification device thermal cycler DICE (TAKARA BIO INC.). PCR reaction conditions were 30 cycles of (i) a thermal denaturation reaction at 98° C. for 10 seconds, (ii) an annealing reaction at 60° C. for 30 seconds, and (iii) an elongation reaction at 72° C. for 1 minute.

(2) Agarose Gel Electrophoresis

After PCR, the reaction solution was applied to 2% agarose gel and electrophoresed for 30 minutes with 100 V in TBA buffer. Gel was then taken out and immersed for 30 minutes in a SYBR safe DNA gel stain in 1×TAE solution (manufactured by Invitrogen) for staining DNA fragments, which were than photographed by Polaroid (registered trademark) camera under UV lamp radiation to see the presence or absence of DNA fragment having a size of about 150 bp. The DNA fragment size was determined by relative mobility compared to DNA fragments with known base pair number, which have been also electrophoresed with the DNA in interest. Determination result of a target gene fragment is shown in Tables 21 to 23.

TABLE 21

| Combination of oligonucleotides | | Results | |
|---|---|---|---|
| Forward primer | Reverse primer | Moraxella osloensis ATCC19976 | Moraxella sp. KMC4-1 |
| SEQ ID NO: 25 | SEQ ID NO: 26 | Y | Y |
| SEQ ID NO: 27 | SEQ ID NO: 28 | Y | Y |
| SEQ ID NO: 29 | SEQ ID NO: 30 | Y | Y |
| SEQ ID NO: 31 | SEQ ID NO: 32 | Y | Y |
| SEQ ID NO: 33 | SEQ ID NO: 34 | Y | Y |
| SEQ ID NO: 35 | SEQ ID NO: 36 | Y | Y |
| SEQ ID NO: 37 | SEQ ID NO: 38 | Y | Y |
| SEQ ID NO: 39 | SEQ ID NO: 40 | Y | Y |
| SEQ ID NO: 41 | SEQ ID NO: 42 | Y | Y |
| Sterile distilled water | Sterile distilled water | N | N |

Y: Gene fragment was amplified.
N: Gene fragment was not amplified.

TABLE 22

| Combination of oligonucleotides | | Results Moraxella sp. | | | | |
|---|---|---|---|---|---|---|
| Forward primer | Reverse primer | KMC4-3 | KMC4-4 | KMC4-5 | KMC4-6 | KMC4-7 |
| SEQ ID NO: 25 | SEQ ID NO: 26 | Y | Y | Y | Y | Y |
| SEQ ID NO: 41 | SEQ ID NO: 42 | Y | Y | Y | Y | Y |
| Sterile distilled water | Sterile distilled water | N | N | N | N | N |

| Combination of oligonucleotides | | Results Moraxella sp. | | | | |
|---|---|---|---|---|---|---|
| Forward primer | Reverse primer | KMC4-8 | KMC4-9 | KMC4-10 | KMC4-11 | KMC4-12 |
| SEQ ID NO: 25 | SEQ ID NO: 26 | Y | Y | Y | Y | Y |
| SEQ ID NO: 41 | SEQ ID NO: 42 | Y | Y | Y | Y | Y |
| Sterile distilled water | Sterile distilled water | N | N | N | N | N |

Y: Gene fragment was amplified.
N: Gene fragment was not amplified.

TABLE 23

| Combination of oligonucleotides | | Results | |
|---|---|---|---|
| Forward primer | Reverse primer | Pseudomonas aeruginosa NBRC13275 | Enterobacter cloacae NBRC3320 |
| SEQ ID NO: 25 | SEQ ID NO: 26 | N | N |
| SEQ ID NO: 27 | SEQ ID NO: 28 | N | N |
| SEQ ID NO: 29 | SEQ ID NO: 30 | N | N |
| SEQ ID NO: 31 | SEQ ID NO: 32 | N | N |
| SEQ ID NO: 33 | SEQ ID NO: 34 | N | N |
| SEQ ID NO: 35 | SEQ ID NO: 36 | N | N |
| SEQ ID NO: 37 | SEQ ID NO: 38 | N | N |
| SEQ ID NO: 39 | SEQ ID NO: 40 | N | N |
| SEQ ID NO: 41 | SEQ ID NO: 42 | N | N |
| Sterile distilled water | Sterile distilled water | N | N |

N: Gene fragment was not amplified.

As shown in Tables 21 and 22, the fadB gene and the fadD gene, each of which is one kind of β oxidation-related enzyme gene, were identified in various bacterial strains of genus *Moraxella*, which is one kind of damp-dry malodor-causing bacteria. Meanwhile, as shown in Table 23, in the sample containing genomic DNA of the microorganisms which do not produce damp-dry malodor-causing substances, the gene fragment was not identified. Thus, it is found that the microorganisms which produce damp-dry malodor-causing substances can be detected quickly and accurately by using a specific oligonucleotide pair.

Further, with regard to the *Moraxella* sp. KMC4-1, the sequence similarity between base sequence of the fadB gene fragment which has been amplified by using each primer pair and the base sequence set forth in SEQ ID NO: 5 is shown in Table 24. Further, the sequence similarity between base sequence of the fadD gene fragment which has been amplified by using each primer pair and the base sequence set forth in SEQ ID NO: 9 is shown in Table 25.

TABLE 24

| Combination of oligonucleotides | | Sequence similarity to the base sequence |
|---|---|---|
| Forward primer | Reverse primer | set forth in SEQ ID NO: 5 |
| SEQ ID NO: 25 | SEQ ID NO: 26 | 97.0% |
| SEQ ID NO: 27 | SEQ ID NO: 28 | 96.0% |
| SEQ ID NO: 29 | SEQ ID NO: 30 | 95.2% |
| SEQ ID NO: 31 | SEQ ID NO: 32 | 96.9% |

TABLE 25

| Combination of oligonucleotides | | Sequence similarity to the base sequence |
|---|---|---|
| Forward primer | Reverse primer | set forth in SEQ ID NO: 9 |
| SEQ ID NO: 35 | SEQ ID NO: 36 | 97.7% |
| SEQ ID NO: 41 | SEQ ID NO: 42 | 95.4% |

As shown in Table 24, each of the base sequence of the amplified gene fragment has sequence similarity of 95% or more to the base sequence of the fadB gene set forth in SEQ ID NO: 5.

Further, as shown in Table 25, each of the base sequence of the amplified gene fragment has sequence similarity of 95% or more to the base sequence of the fadD gene set forth in SEQ ID NO: 9.

Based on these results, it was found that the β oxidation-related enzyme gene fragments of microorganisms which produce damp-dry malodor-causing substances can be amplified by using the oligonucleotide of the present invention. Therefore, the β oxidation-related enzyme gene can be detected quickly and accurately.

Example 4 Detection of Microorganisms which Produce Damp-Dry Malodor-Causing Substances from Environment (1) Preparation of Genomic DNA Three towels T1 to T3 having damp-dry malodor and new towel (T4) having no such malodor were cut into pieces. By using a kit for preparing genomic DNA (trade name: PrepMan Ultra Reagent, manufactured by Applied Biosystems), a solution of genomic DNA was prepared from these towels.

(2) PCR Reaction

By mixing 5 μL solution of the genomic DNA prepared above diluted ×100 with distilled sterile water, 0.1 μL of TaKaRa EX Taq HS (trade name, manufactured by Takara Bio Inc.), 1.6 μL of the mixture of four deoxyribonucleotide triphosphate (dNTP) (dNTP mixture liquid attached to TaKaRa EX Taq Hot Start Version (trade name) manufactured by Takara Bio Inc.), 2 μL of 10× conc. reaction buffer (buffer attached to TaKaRa EX Taq Hot Start Version (trade name) manufactured by Takara Bio Inc.), 0.4 μL of the primer (des_F2, 20 pmol/L) containing the oligonucleotide having the base sequence set forth in SEQ ID NO: 15, 0.4 μL of the primer (des_R2, 20 pmol/L) containing the oligonucleotide having the base sequence set forth in SEQ ID NO: 16, and 10.5 μL of distilled sterile water, 20 μL PCR reaction solution was prepared.

As a negative control, a PCR reaction solution, in which distilled sterile water was added instead of the DNA template, was prepared in the same manner as above.

PCR reaction solutions were prepared in the same manner as above, except that, instead of the primer set of the primer containing the oligonucleotide having the base sequence set forth in SEQ ID NO: 15 and the primer containing the oligonucleotide having the base sequence set forth in SEQ ID NO: 16, the primer set described in Table 26 was used.

The PCR reaction solution was subjected to a gene amplification treatment using an automatic gene amplification device thermal cycler DICE (TAKARA BIO INC.). PCR reaction conditions were 40 cycles of (i) a thermal denaturation reaction at 98° C. for 10 seconds, and (ii) an annealing reaction and an elongation reaction at 68° C. for 1 minute.

(3) Agarose Gel Electrophoresis

After PCR, the reaction solution was applied to 2% agarose gel and electrophoresed for 30 minutes with 100 V in TBA buffer. Gel was then taken out and immersed for 30 minutes in a SYBR safe DNA gel stain in 1×TAE solution (manufactured by Invitrogen) for staining DNA fragments, which were than photographed by Polaroid (registered trademark) camera under UV lamp radiation to see the presence or absence of DNA fragment having a size of about 150 bp. The DNA fragment size was determined by relative mobility compared to DNA fragments with known base pair number, which have been also electrophoresed with the DNA in interest. Determination result of a target gene fragment is shown in Table 26.

TABLE 26

| Combination of oligonucleotides | | Results | | | |
|---|---|---|---|---|---|
| Forward primer | Reverse primer | Towel T1 | Towel T2 | Towel T3 | Towel T4 |
| SEQ ID NO: 15 | SEQ ID NO: 16 | Y | Y | Y | N |
| SEQ ID NO: 25 | SEQ ID NO: 26 | Y | Y | Y | N |
| SEQ ID NO: 27 | SEQ ID NO: 28 | Y | Y | Y | N |
| SEQ ID NO: 35 | SEQ ID NO: 36 | Y | Y | Y | N |
| SEQ ID NO: 41 | SEQ ID NO: 42 | Y | Y | Y | N |

Y: Gene fragment was amplified.
N: Gene fragment was not amplified.

From all of the three towels having damp-dry malodor (that is, T1 to T3), an amplified DNA fragment was detected at the size location of about 150 bp on the gel. Further, *Moraxella* sp. was isolated by an isolation method from all of the three towels having damp-dry malodor. On the other hand, amplification of the gene fragment was not identified from the new towel (that is, T4) having no damp-dry malodor.

Based on these results described above, it was found that, even from an environmental sample containing various bacterial strains with different types, the microorganisms which produce damp-dry malodor-causing substances can be detected by using the oligonucleotide of the present invention.

As described above, by bringing microorganisms which produce damp-dry malodor-causing substances and a test substance into contact with each other, detecting expression of the fatty acid desaturase gene and/or the β oxidation-related enzyme gene derived from the microorganisms by using the oligonucleotide or oligonucleotide pair of the present invention, and evaluating the expression on the basis of change in gene expression amount, it is possible to evaluate conveniently the damp-dry malodor inhibitory function of the test substance with high accuracy. Further, according to the method of evaluating inhibitory effect on damp-dry malodor of the present invention, it is possible to screen a damp-dry malodor inhibitor by selecting a test substance which decreases expression amount of the fatty acid desaturase gene and/or the β oxidation-related enzyme gene. Still further, by amplifying a fragment of the fatty acid desaturase gene and/or the β oxidation-related enzyme gene by using the oligonucleotide or oligonucleotide pair of the present invention and determining the presence or absence of an amplified fragment, microorganisms which produce damp-dry malodor-causing substances, that are present in a fabric product including towel and clothes, an environment or the like, can be detected quickly and accurately.

Having described our invention as related to the present embodiments, it is our intention that the invention not be limited by any of the details of the description, unless otherwise specified, but rather be construed broadly within its spirit and scope as set out in the accompanying claims.

This non-provisional application Claims priority under 35 U.S.C. §119 (a) on Patent Application No. 2012-122032 filed in Japan on May 29, 2012, and Patent Application No. 2013-109303 filed in Japan on May 23, 2013, each of which is entirely herein incorporated by reference.

What is claimed is:

1. A method of evaluating an inhibitory effect on damp-dry malodor, comprising the steps of:
bringing microorganisms which produce damp-dry malodor-causing substances and a test substance into contact with each other in the presence of a sebaceous dirt component;
detecting expression of at least one gene selected from the group consisting of a fatty acid desaturase gene and a β oxidation-related enzyme gene derived from the microorganisms; and thereby
evaluating a damp-dry malodor inhibitory function of the test substance based on a change in expression amount of the at least one gene;
wherein the expression of the at least one gene is detected by using at least one oligonucleotide pair selected from the group consisting of:
an oligonucleotide pair containing oligonucleotides (a) and (b) as described below,
an oligonucleotide pair containing oligonucleotides (c) and (d) as described below,
an oligonucleotide pair containing oligonucleotides (e) and (f) as described below,
an oligonucleotide pair containing oligonucleotides (g) and (h) as described below,
an oligonucleotide pair containing oligonucleotides (i) and (j) as described below,
an oligonucleotide pair containing oligonucleotides (k) and (l) as described below,
an oligonucleotide pair containing oligonucleotides (m) and (n) as described below,
an oligonucleotide pair containing oligonucleotides (o) and (p) as described below,
an oligonucleotide pair containing oligonucleotides (q) and (r) as described below,
an oligonucleotide pair containing oligonucleotides (s) and (t) as described below,
an oligonucleotide pair containing oligonucleotides (u) and (v) as described below,
an oligonucleotide pair containing oligonucleotides (w) and (x) as described below,
an oligonucleotide pair containing oligonucleotides (y) and (z) as described below,
an oligonucleotide pair containing oligonucleotides (a1) and (b1) as described below, and
an oligonucleotide pair containing oligonucleotides (c1) and (d1) as described below:
wherein
oligonucleotide (a) is an oligonucleotide having the base sequence set forth in SEQ ID NO: 13, or an oligonucleotide having a base sequence set forth in SEQ ID NO: 13 with a substitution, deletion, insertion, or addition of 1 to 3 nucleotides which can be used for detecting the fatty acid desaturase gene;
oligonucleotide (b) is an oligonucleotide having the base sequence set forth in SEQ ID NO: 14, or an oligonucleotide having a base sequence set forth in SEQ ID NO: 14 with a substitution, deletion, insertion, or addition of 1 to 3 nucleotides which can be used for detecting the fatty acid desaturase gene;
oligonucleotide (c) is an oligonucleotide having the base sequence set forth in SEQ ID NO: 15, or an oligonucleotide having a base sequence set forth in SEQ ID NO: 15 with a substitution, deletion, insertion, or addition of 1 to 3 nucleotides which can be used for detecting the fatty acid desaturase gene;
oligonucleotide (d) is an oligonucleotide having the base sequence set forth in SEQ ID NO: 16, or an oligonucleotide having a base sequence set forth in SEQ ID NO: 16 with a substitution, deletion, insertion, or addition of 1 to 3 nucleotides which can be used for detecting the fatty acid desaturase gene;
oligonucleotide (e) is an oligonucleotide having the base sequence set forth in SEQ ID NO: 17, or an oligonucleotide having a base sequence set forth in SEQ ID NO: 17 with a substitution, deletion, insertion, or addition of 1 to 3 nucleotides which can be used for detecting the fatty acid desaturase gene;
oligonucleotide (f) is an oligonucleotide having the base sequence set forth in SEQ ID NO: 18, or an oligonucleotide having a base sequence set forth in SEQ ID NO: 18 with a substitution, deletion, insertion, or addition of 1 to 3 nucleotides which can be used for detecting the fatty acid desaturase gene;
oligonucleotide (g) is an oligonucleotide having the base sequence set forth in SEQ ID NO: 19, or an oligonucleotide having a base sequence set forth in SEQ ID NO: 19 with a substitution, deletion, insertion, or addition of 1 to 3 nucleotides which can be used for detecting the fatty acid desaturase gene;
oligonucleotide (h) is an oligonucleotide having the base sequence set forth in SEQ ID NO: 20, or an oligonucleotide having a base sequence set forth in SEQ ID NO: 20 with a substitution, deletion, insertion, or addition of 1 to 3 nucleotides which can be used for detecting the fatty acid desaturase gene;
oligonucleotide (i) is an oligonucleotide having the base sequence set forth in SEQ ID NO: 21, or an oligonucleotide having a base sequence set forth in SEQ ID NO: 21 with a substitution, deletion, insertion, or addition of 1 to 3 nucleotides which can be used for detecting the fatty acid desaturase gene;
oligonucleotide (j) is an oligonucleotide having the base sequence set forth in SEQ ID NO: 22, or an oligonucleotide having a base sequence set forth in SEQ ID NO: 22 with a substitution, deletion, insertion, or addition of 1 to 3 nucleotides which can be used for detecting the fatty acid desaturase gene;
oligonucleotide (k) is an oligonucleotide having the base sequence set forth in SEQ ID NO: 23, or an oligonucleotide having a base sequence set forth in SEQ ID NO: 23 with a substitution, deletion, insertion, or addition of 1 to 3 nucleotides which can be used for detecting the fatty acid desaturase gene;
oligonucleotide (l) is an oligonucleotide having the base sequence set forth in SEQ ID NO: 24, or an oligonucleotide having a base sequence set forth in SEQ ID NO: 24 with a substitution, deletion, insertion, or addition of 1 to 3 nucleotides which can be used for detecting the fatty acid desaturase gene;
oligonucleotide (m) is an oligonucleotide having the base sequence set forth in SEQ ID NO: 25, or an oligonucleotide having a base sequence set forth in SEQ ID NO: 25 with a substitution, deletion, insertion, or addition of 1 to 3 nucleotides which can be used for detecting the β oxidation-related enzyme gene;
oligonucleotide (n) is an oligonucleotide having the base sequence set forth in SEQ ID NO: 26, or an oligonucleotide having a base sequence set forth in SEQ ID NO: 26 with a substitution, deletion, insertion, or addition of 1 to 3 nucleotides which can be used for detecting the β oxidation-related enzyme gene;
oligonucleotide (o) is an oligonucleotide having the base sequence set forth in SEQ ID NO: 27, or an oligonucleotide having a base sequence set forth in SEQ ID NO: 27 with a substitution, deletion, insertion, or addition of 1 to 3 nucleotides which can be used for detecting the β oxidation-related enzyme gene;
oligonucleotide (p) is an oligonucleotide having the base sequence set forth in SEQ ID NO: 28, or an oligonucleotide having a base sequence set forth in SEQ ID NO: 28 with a substitution, deletion, insertion, or addition of 1 to 3 nucleotides which can be used for detecting the β oxidation-related enzyme gene;
oligonucleotide (q) is an oligonucleotide having the base sequence set forth in SEQ ID NO: 29, or an oligonucleotide having a base sequence set forth in SEQ ID NO: 29 with a substitution, deletion, insertion, or addition of 1 to 3 nucleotides which can be used for detecting the β oxidation-related enzyme gene;
oligonucleotide (r) is an oligonucleotide having the base sequence set forth in SEQ ID NO: 30, or an oligonucleotide having a base sequence set forth in SEQ ID NO: 30 with a substitution, deletion, insertion, or addition of 1 to 3 nucleotides which can be used for detecting the β oxidation-related enzyme gene;
oligonucleotide (s) is an oligonucleotide having the base sequence set forth in SEQ ID NO: 31, or an oligonucleotide having a base sequence set forth in SEQ ID NO: 31 with a substitution, deletion, insertion, or addition of 1 to 3 nucleotides which can be used for detecting the β oxidation-related enzyme gene;
oligonucleotide (t) is an oligonucleotide having the base sequence set forth in SEQ ID NO: 32, or an oligonucleotide having a base sequence set forth in SEQ ID NO: 32 with a substitution, deletion, insertion, or addition of 1 to 3 nucleotides which can be used for detecting the β oxidation-related enzyme gene;
oligonucleotide (u) is an oligonucleotide having the base sequence set forth in SEQ ID NO: 33, or an oligonucleotide having a base sequence set forth in SEQ ID NO: 33 with a substitution, deletion, insertion, or addition of 1 to 3 nucleotides which can be used for detecting the β oxidation-related enzyme gene;
oligonucleotide (v) is an oligonucleotide having the base sequence set forth in SEQ ID NO: 34, or an oligonucleotide having a base sequence set forth in SEQ ID NO: 34 with a substitution, deletion, insertion, or addition of 1 to 3 nucleotides which can be used for detecting the β oxidation-related enzyme gene;
oligonucleotide (w) is an oligonucleotide having the base sequence set forth in SEQ ID NO: 35, or an oligonucleotide having a base sequence set forth in SEQ ID NO: 35 with a substitution, deletion, insertion, or addition of 1 to 3 nucleotides which can be used for detecting the β oxidation-related enzyme gene;
oligonucleotide (x) is an oligonucleotide having the base sequence set forth in SEQ ID NO: 36, or an oligonucleotide having a base sequence set forth in SEQ ID NO: 36 with a substitution, deletion, insertion, or addition of 1 to 3 nucleotides which can be used for detecting the β oxidation-related enzyme gene;
oligonucleotide (y) is an oligonucleotide having the base sequence set forth in SEQ ID NO: 37, or an oligonucleotide having a base sequence set forth in SEQ ID NO: 37 with a substitution, deletion, insertion, or addition of 1 to 3 nucleotides which can be used for detecting the β oxidation-related enzyme gene;
oligonucleotide (z) is an oligonucleotide having the base sequence set forth in SEQ ID NO: 38, or an oligonucleotide having a base sequence set forth in SEQ ID NO: 38 with a substitution, deletion, insertion, or addition of 1 to 3 nucleotides which can be used for detecting the β oxidation-related enzyme gene;
oligonucleotide (a1) is an oligonucleotide having the base sequence set forth in SEQ ID NO: 39, or an oligonucleotide having a base sequence set forth in SEQ ID NO: 39 with a substitution, deletion, insertion, or addition of 1 to 3 nucleotides which can be used for detecting the β oxidation-related enzyme gene;

oligonucleotide (b1) is an oligonucleotide having the base sequence set forth in SEQ ID NO: 40, or an oligonucleotide having a base sequence set forth in SEQ ID NO: 40 with a substitution, deletion, insertion, or addition of 1 to 3 nucleotides which can be used for detecting the β oxidation-related enzyme gene;

oligonucleotide (c1) is an oligonucleotide having the base sequence set forth in SEQ ID NO: 41, or an oligonucleotide having a base sequence set forth in SEQ ID NO: 41 with a substitution, deletion, insertion, or addition of 1 to 3 nucleotides which can be used for detecting the β oxidation-related enzyme gene; and oligonucleotide (d1) is an oligonucleotide having the base sequence set forth in SEQ ID NO: 42, or an oligonucleotide having a base sequence set forth in SEQ ID NO: 42 with a substitution, deletion, insertion, or addition of 1 to 3 nucleotides which can be used for detecting the β oxidation-related enzyme gene.

2. The method according to claim 1, wherein the microorganisms produce the damp-dry malodor-causing substance 4-methyl-3-hexenoic acid.

3. The method according to claim 1, wherein the sebaceous dirt component is an anteiso fatty acid.

4. The method according to claim 1, wherein the fatty acid desaturase gene is a Δ9desaturase gene.

5. The method according to claim 4, wherein the expression of the Δ9desaturase gene is detected by using at least one oligonucleotide pair selected from the group consisting of:

the oligonucleotide pair containing the oligonucleotides (a) and (b);
the oligonucleotide pair containing the oligonucleotides (c) and (d);
the oligonucleotide pair containing the oligonucleotides (e) and (f);
the oligonucleotide pair containing the oligonucleotides (g) and (h);
the oligonucleotide pair containing the oligonucleotides (i) and (j); and
the oligonucleotide pair containing the oligonucleotides (k) and (l).

6. The method according to claim 1, wherein the β oxidation-related enzyme gene is at least one gene selected from the group consisting of a fadB gene and a fadD gene.

7. The method according to claim 6,
wherein the expression of the fadB gene is detected by using at least one oligonucleotide pair selected from the group consisting of:
the oligonucleotide pair containing the oligonucleotides (m) and (n);
the oligonucleotide pair containing the oligonucleotides (o) and (p);
the oligonucleotide pair containing the oligonucleotides (q) and (r); and
the oligonucleotide pair containing the oligonucleotides (s) and (t).

8. The method according to claim 6,
wherein the expression of the fadD gene is detected by using at least one oligonucleotide pair selected from the group consisting of:
the oligonucleotide pair containing the oligonucleotides (u) and (v);
the oligonucleotide pair containing the oligonucleotides (w) and (x);
the oligonucleotide pair containing the oligonucleotides (y) and (z);
the oligonucleotide pair containing the oligonucleotides (a1) and (b1); and
the oligonucleotide pair containing the oligonucleotides (c1) and (d1).

9. The method according to claim 1, wherein the microorganisms are at least one microbial strain selected from the group consisting of species of *Moraxella* sp. and *Moraxella osloensis*.

10. A method of screening a damp-dry malodor inhibitor, which comprises
bringing microorganisms which produce damp-dry malodor-causing substances and a test substance into contact with each other in the presence of a sebaceous dirt component;
detecting expression of at least one gene selected from the group consisting of a fatty acid desaturase gene and a β oxidation-related enzyme gene derived from the microorganisms; and thereby
selecting or evaluating a test substance that reduces the expression amount of the at least one gene as a damp-dry malodor inhibitor,
wherein the expression of the at least one gene is detected by using at least one oligonucleotide pair selected from the group consisting of:
an oligonucleotide pair containing oligonucleotides (a) and (b) as described below,
an oligonucleotide pair containing oligonucleotides (c) and (d) as described below,
an oligonucleotide pair containing oligonucleotides (e) and (f) as described below,
an oligonucleotide pair containing oligonucleotides (g) and (h) as described below,
an oligonucleotide pair containing oligonucleotides (i) and (j) as described below,
an oligonucleotide pair containing oligonucleotides (k) and (l) as described below,
an oligonucleotide pair containing oligonucleotides (m) and (n) as described below,
an oligonucleotide pair containing oligonucleotides (o) and (p) as described below,
an oligonucleotide pair containing oligonucleotides (q) and (r) as described below,
an oligonucleotide pair containing oligonucleotides (s) and (t) as described below,
an oligonucleotide pair containing oligonucleotides (u) and (v) as described below,
an oligonucleotide pair containing oligonucleotides (w) and (x) as described below,
an oligonucleotide pair containing oligonucleotides (y) and (z) as described below,
an oligonucleotide pair containing oligonucleotides (a1) and (b1) as described below, and
an oligonucleotide pair containing oligonucleotides (c1) and (d1) as described below:
wherein
oligonucleotide (a) is an oligonucleotide having the base sequence set forth in SEQ ID NO: 13, or an oligonucleotide having a base sequence set forth in SEQ ID NO: 13 with a substitution, deletion, insertion, or addition of 1 to 3 nucleotides which can be used for detecting the fatty acid desaturase gene;
oligonucleotide (b) is an oligonucleotide having the base sequence set forth in SEQ ID NO: 14, or an oligonucleotide having a base sequence set forth in SEQ ID NO:

14 with a substitution, deletion, insertion, or addition of 1 to 3 nucleotides which can be used for detecting the fatty acid desaturase gene;

oligonucleotide (c) is an oligonucleotide having the base sequence set forth in SEQ ID NO: 15, or an oligonucleotide having a base sequence set forth in SEQ ID NO: 15 with a substitution, deletion, insertion, or addition of 1 to 3 nucleotides which can be used for detecting the fatty acid desaturase gene;

oligonucleotide (d) is an oligonucleotide having the base sequence set forth in SEQ ID NO: 16, or an oligonucleotide having a base sequence set forth in SEQ ID NO: 16 with a substitution, deletion, insertion, or addition of 1 to 3 nucleotides which can be used for detecting the fatty acid desaturase gene;

oligonucleotide (e) is an oligonucleotide having the base sequence set forth in SEQ ID NO: 17, or an oligonucleotide having a base sequence set forth in SEQ ID NO: 17 with a substitution, deletion, insertion, or addition of 1 to 3 nucleotides which can be used for detecting the fatty acid desaturase gene;

oligonucleotide (f) is an oligonucleotide having the base sequence set forth in SEQ ID NO: 18, or an oligonucleotide having a base sequence set forth in SEQ ID NO: 18 with a substitution, deletion, insertion, or addition of 1 to 3 nucleotides which can be used for detecting the fatty acid desaturase gene;

oligonucleotide (g) is an oligonucleotide having the base sequence set forth in SEQ ID NO: 19, or an oligonucleotide having a base sequence set forth in SEQ ID NO: 19 with a substitution, deletion, insertion, or addition of 1 to 3 nucleotides which can be used for detecting the fatty acid desaturase gene;

oligonucleotide (h) is an oligonucleotide having the base sequence set forth in SEQ ID NO: 20, or an oligonucleotide having a base sequence set forth in SEQ ID NO: 20 with a substitution, deletion, insertion, or addition of 1 to 3 nucleotides which can be used for detecting the fatty acid desaturase gene;

oligonucleotide (i) is an oligonucleotide having the base sequence set forth in SEQ ID NO: 21, or an oligonucleotide having a base sequence set forth in SEQ ID NO: 21 with a substitution, deletion, insertion, or addition of 1 to 3 nucleotides which can be used for detecting the fatty acid desaturase gene;

oligonucleotide (j) is an oligonucleotide having the base sequence set forth in SEQ ID NO: 22, or an oligonucleotide having a base sequence set forth in SEQ ID NO: 22 with a substitution, deletion, insertion, or addition of 1 to 3 nucleotides which can be used for detecting the fatty acid desaturase gene;

oligonucleotide (k) is an oligonucleotide having the base sequence set forth in SEQ ID NO: 23, or an oligonucleotide having a base sequence set forth in SEQ ID NO: 23 with a substitution, deletion, insertion, or addition of 1 to 3 nucleotides which can be used for detecting the fatty acid desaturase gene;

oligonucleotide (l) is an oligonucleotide having the base sequence set forth in SEQ ID NO: 24, or an oligonucleotide having a base sequence set forth in SEQ ID NO: 24 with a substitution, deletion, insertion, or addition of 1 to 3 nucleotides which can be used for detecting the fatty acid desaturase gene;

oligonucleotide (m) is an oligonucleotide having the base sequence set forth in SEQ ID NO: 25, or an oligonucleotide having a base sequence set forth in SEQ ID NO: 25 with a substitution, deletion, insertion, or addition of 1 to 3 nucleotides which can be used for detecting the β oxidation-related enzyme gene;

oligonucleotide (n) is an oligonucleotide having the base sequence set forth in SEQ ID NO: 26, or an oligonucleotide having a base sequence set forth in SEQ ID NO: 26 with a substitution, deletion, insertion, or addition of 1 to 3 nucleotides which can be used for detecting the β oxidation-related enzyme gene;

oligonucleotide (o) is an oligonucleotide having the base sequence set forth in SEQ ID NO: 27, or an oligonucleotide having a base sequence set forth in SEQ ID NO: 27 with a substitution, deletion, insertion, or addition of 1 to 3 nucleotides which can be used for detecting the β oxidation-related enzyme gene;

oligonucleotide (p) is an oligonucleotide having the base sequence set forth in SEQ ID NO: 28, or an oligonucleotide having a base sequence set forth in SEQ ID NO: 28 with a substitution, deletion, insertion, or addition of 1 to 3 nucleotides which can be used for detecting the β oxidation-related enzyme gene;

oligonucleotide (q) is an oligonucleotide having the base sequence set forth in SEQ ID NO: 29, or an oligonucleotide having a base sequence set forth in SEQ ID NO: 29 with a substitution, deletion, insertion, or addition of 1 to 3 nucleotides which can be used for detecting the β oxidation-related enzyme gene;

oligonucleotide (r) is an oligonucleotide having the base sequence set forth in SEQ ID NO: 30, or an oligonucleotide having a base sequence set forth in SEQ ID NO: 30 with a substitution, deletion, insertion, or addition of 1 to 3 nucleotides which can be used for detecting the β oxidation-related enzyme gene;

oligonucleotide (s) is an oligonucleotide having the base sequence set forth in SEQ ID NO: 31, or an oligonucleotide having a base sequence set forth in SEQ ID NO: 31 with a substitution, deletion, insertion, or addition of 1 to 3 nucleotides which can be used for detecting the β oxidation-related enzyme gene;

oligonucleotide (t) is an oligonucleotide having the base sequence set forth in SEQ ID NO: 32, or an oligonucleotide having a base sequence set forth in SEQ ID NO: 32 with a substitution, deletion, insertion, or addition of 1 to 3 nucleotides which can be used for detecting the β oxidation-related enzyme gene;

oligonucleotide (u) is an oligonucleotide having the base sequence set forth in SEQ ID NO: 33, or an oligonucleotide having a base sequence set forth in SEQ ID NO: 33 with a substitution, deletion, insertion, or addition of 1 to 3 nucleotides which can be used for detecting the β oxidation-related enzyme gene;

oligonucleotide (v) is an oligonucleotide having the base sequence set forth in SEQ ID NO: 34, or an oligonucleotide having a base sequence set forth in SEQ ID NO: 34 with a substitution, deletion, insertion, or addition of 1 to 3 nucleotides which can be used for detecting the β oxidation-related enzyme gene;

oligonucleotide (w) is an oligonucleotide having the base sequence set forth in SEQ ID NO: 35, or an oligonucleotide having a base sequence set forth in SEQ ID NO: 35 with a substitution, deletion, insertion, or addition of 1 to 3 nucleotides which can be used for detecting the β oxidation-related enzyme gene;

oligonucleotide (x) is an oligonucleotide having the base sequence set forth in SEQ ID NO: 36, or an oligonucleotide having a base sequence set forth in SEQ ID NO: 36 with a substitution, deletion, insertion, or addition of 1 to 3 nucleotides which can be used for detecting the β oxidation-related enzyme gene;

oligonucleotide (y) is an oligonucleotide having the base sequence set forth in SEQ ID NO: 37, or an oligonucleotide having a base sequence set forth in SEQ ID NO: 37 with a substitution, deletion, insertion, or addition of 1 to 3 nucleotides which can be used for detecting the β oxidation-related enzyme gene;

oligonucleotide (z) is an oligonucleotide having the base sequence set forth in SEQ ID NO: 38, or an oligonucleotide having a base sequence set forth in SEQ ID NO: 38 with a substitution, deletion, insertion, or addition of 1 to 3 nucleotides which can be used for detecting the β oxidation-related enzyme gene;

oligonucleotide (a1) is an oligonucleotide having the base sequence set forth in SEQ ID NO: 39, or an oligonucleotide having a base sequence set forth in SEQ ID NO: 39 with a substitution, deletion, insertion, or addition of 1 to 3 nucleotides which can be used for detecting the β oxidation-related enzyme gene;

oligonucleotide (b1) is an oligonucleotide having the base sequence set forth in SEQ ID NO: 40, or an oligonucleotide having a base sequence set forth in SEQ ID NO: 40 with a substitution, deletion, insertion, or addition of 1 to 3 nucleotides which can be used for detecting the β oxidation-related enzyme gene;

oligonucleotide (c1) is an oligonucleotide having the base sequence set forth in SEQ ID NO: 41, or an oligonucleotide having a base sequence set forth in SEQ ID NO: 41 with a substitution, deletion, insertion, or addition of 1 to 3 nucleotides which can be used for detecting the β oxidation-related enzyme gene; and oligonucleotide (d1) is an oligonucleotide having the base sequence set forth in SEQ ID NO: 42, or an oligonucleotide having a base sequence set forth in SEQ ID NO: 42 with a substitution, deletion, insertion, or addition of 1 to 3 nucleotides which can be used for detecting the β oxidation-related enzyme gene.

11. A method of detecting microorganisms which produce damp-dry malodor-causing substances, comprising the steps of:

amplifying at least one fragment of a gene selected from the group consisting of a Δ9desaturase gene, an fadB gene and an fadD gene derived from microorganisms which produce damp-dry malodor-causing substances;

determining the presence or absence of an amplified fragment; and thereby detecting the microorganisms which produce damp-dry malodor-causing substances, wherein the detection of the microorganisms which produce damp-dry malodor-causing substances is performed by using at least one oligonucleotide pair selected from the group consisting of:

an oligonucleotide pair containing oligonucleotides (c) and (d) as described below, an oligonucleotide pair containing oligonucleotides (e) and (f) as described below, an oligonucleotide pair containing oligonucleotides (g) and (h) as described below, an oligonucleotide pair containing oligonucleotides (i) and (j) as described below, an oligonucleotide pair containing oligonucleotides (k) and (l) as described below, an oligonucleotide pair containing oligonucleotides (m) and (n) as described below, an oligonucleotide pair containing oligonucleotides (o) and (p) as described below, an oligonucleotide pair containing oligonucleotides (q) and (r) as described below, an oligonucleotide pair containing oligonucleotides (s) and (t) as described below, an oligonucleotide pair containing oligonucleotides (u) and (v) as described below, an oligonucleotide pair containing oligonucleotides (w) and (x) as described below, an oligonucleotide pair containing oligonucleotides (y) and (z) as described below, an oligonucleotide pair containing oligonucleotides (a1) and (b1) as described below, and an oligonucleotide pair containing oligonucleotides (c1) and (d1) as described below:

wherein oligonucleotide (c) is an oligonucleotide having the base sequence set forth in SEQ ID NO: 15, or an oligonucleotide having a base sequence set forth in SEQ ID NO: 15 with a substitution, deletion, insertion, or addition of 1 to 3 nucleotides which can be used for detecting the fatty acid desaturase gene;

oligonucleotide (d) is an oligonucleotide having the base sequence set forth in SEQ ID NO: 16, or an oligonucleotide having a base sequence set forth in SEQ ID NO: 16 with a substitution, deletion, insertion, or addition of 1 to 3 nucleotides which can be used for detecting the fatty acid desaturase gene;

oligonucleotide (e) is an oligonucleotide having the base sequence set forth in SEQ ID NO: 17, or an oligonucleotide having a base sequence set forth in SEQ ID NO: 17 with a substitution, deletion, insertion, or addition of 1 to 3 nucleotides which can be used for detecting the fatty acid desaturase gene;

oligonucleotide (f) is an oligonucleotide having the base sequence set forth in SEQ ID NO: 18, or an oligonucleotide having a base sequence set forth in SEQ ID NO: 18 with a substitution, deletion, insertion, or addition of 1 to 3 nucleotides which can be used for detecting the fatty acid desaturase gene;

oligonucleotide (g) is an oligonucleotide having the base sequence set forth in SEQ ID NO: 19, or an oligonucleotide having a base sequence set forth in SEQ ID NO: 19 with a substitution, deletion, insertion, or addition of 1 to 3 nucleotides which can be used for detecting the fatty acid desaturase gene;

oligonucleotide (h) is an oligonucleotide having the base sequence set forth in SEQ ID NO: 20, or an oligonucleotide having a base sequence set forth in SEQ ID NO: 20 with a substitution, deletion, insertion, or addition of 1 to 3 nucleotides which can be used for detecting the fatty acid desaturase gene;

oligonucleotide (i) is an oligonucleotide having the base sequence set forth in SEQ ID NO: 21, or an oligonucleotide having a base sequence set forth in SEQ ID NO: 21 with a substitution, deletion, insertion, or addition of 1 to 3 nucleotides which can be used for detecting the fatty acid desaturase gene;

oligonucleotide (j) is an oligonucleotide having the base sequence set forth in SEQ ID NO: 22, or an oligonucleotide having a base sequence set forth in SEQ ID NO: 22 with a substitution, deletion, insertion, or addition of 1 to 3 nucleotides which can be used for detecting the fatty acid desaturase gene;

oligonucleotide (k) is an oligonucleotide having the base sequence set forth in SEQ ID NO: 23, or an oligonucleotide having a base sequence set forth in SEQ ID NO: 23 with a substitution, deletion, insertion, or addition of 1 to 3 nucleotides which can be used for detecting the fatty acid desaturase gene;

oligonucleotide (l) is an oligonucleotide having the base sequence set forth in SEQ ID NO: 24, or an oligonucleotide having a base sequence set forth in SEQ ID NO: 24 with a substitution, deletion, insertion, or addition of 1 to 3 nucleotides which can be used for detecting the fatty acid desaturase gene;

oligonucleotide (m) is an oligonucleotide having the base sequence set forth in SEQ ID NO: 25, or an oligonucleotide having a base sequence set forth in SEQ ID NO: 25 with a substitution, deletion, insertion, or addition of 1 to 3 nucleotides which can be used for detecting the β oxidation-related enzyme gene;

oligonucleotide (n) is an oligonucleotide having the base sequence set forth in SEQ ID NO: 26, or an oligonucleotide having a base sequence set forth in SEQ ID NO: 26 with a substitution, deletion, insertion, or addition of 1 to 3 nucleotides which can be used for detecting the β oxidation-related enzyme gene;

oligonucleotide (o) is an oligonucleotide having the base sequence set forth in SEQ ID NO: 27, or an oligonucleotide having a base sequence set forth in SEQ ID NO: 27 with a substitution, deletion, insertion, or addition of 1 to 3 nucleotides which can be used for detecting the β oxidation-related enzyme gene;

oligonucleotide (p) is an oligonucleotide having the base sequence set forth in SEQ ID NO: 28, or an oligonucleotide having a base sequence set forth in SEQ ID NO: 28 with a substitution, deletion, insertion, or addition of 1 to 3 nucleotides which can be used for detecting the β oxidation-related enzyme gene;

oligonucleotide (q) is an oligonucleotide having the base sequence set forth in SEQ ID NO: 29, or an oligonucleotide having a base sequence set forth in SEQ ID NO: 29 with a substitution, deletion, insertion, or addition of 1 to 3 nucleotides which can be used for detecting the β oxidation-related enzyme gene;

oligonucleotide (r) is an oligonucleotide having the base sequence set forth in SEQ ID NO: 30, or an oligonucleotide having a base sequence set forth in SEQ ID NO: 30 with a substitution, deletion, insertion, or addition of 1 to 3 nucleotides which can be used for detecting the β oxidation-related enzyme gene;

oligonucleotide (s) is an oligonucleotide having the base sequence set forth in SEQ ID NO: 31, or an oligonucleotide having a base sequence set forth in SEQ ID NO: 31 with a substitution, deletion, insertion, or addition of 1 to 3 nucleotides which can be used for detecting the β oxidation-related enzyme gene;

oligonucleotide (t) is an oligonucleotide having the base sequence set forth in SEQ ID NO: 32, or an oligonucleotide having a base sequence set forth in SEQ ID NO: 32 with a substitution, deletion, insertion, or addition of 1 to 3 nucleotides which can be used for detecting the β oxidation-related enzyme gene;

oligonucleotide (u) is an oligonucleotide having the base sequence set forth in SEQ ID NO: 33, or an oligonucleotide having a base sequence set forth in SEQ ID NO: 33 with a substitution, deletion, insertion, or addition of 1 to 3 nucleotides which can be used for detecting the β oxidation-related enzyme gene;

oligonucleotide (v) is an oligonucleotide having the base sequence set forth in SEQ ID NO: 34, or an oligonucleotide having a base sequence set forth in SEQ ID NO: 34 with a substitution, deletion, insertion, or addition of 1 to 3 nucleotides which can be used for detecting the β oxidation-related enzyme gene;

oligonucleotide (w) is an oligonucleotide having the base sequence set forth in SEQ ID NO: 35, or an oligonucleotide having a base sequence set forth in SEQ ID NO: 35 with a substitution, deletion, insertion, or addition of 1 to 3 nucleotides which can be used for detecting the β oxidation-related enzyme gene;

oligonucleotide (x) is an oligonucleotide having the base sequence set forth in SEQ ID NO: 36, or an oligonucleotide having a base sequence set forth in SEQ ID NO: 36 with a substitution, deletion, insertion, or addition of 1 to 3 nucleotides which can be used for detecting the β oxidation-related enzyme gene;

oligonucleotide (y) is an oligonucleotide having the base sequence set forth in SEQ ID NO: 37, or an oligonucleotide having a base sequence set forth in SEQ ID NO: 37 with a substitution, deletion, insertion, or addition of 1 to 3 nucleotides which can be used for detecting the β oxidation-related enzyme gene;

oligonucleotide (z) is an oligonucleotide having the base sequence set forth in SEQ ID NO: 38, or an oligonucleotide having a base sequence set forth in SEQ ID NO: 38 with a substitution, deletion, insertion, or addition of 1 to 3 nucleotides which can be used for detecting the β oxidation-related enzyme gene;

oligonucleotide (a1) is an oligonucleotide having the base sequence set forth in SEQ ID NO: 39, or an oligonucleotide having a base sequence set forth in SEQ ID NO: 39 with a substitution, deletion, insertion, or addition of 1 to 3 nucleotides which can be used for detecting the β oxidation-related enzyme gene;

oligonucleotide (b1) is an oligonucleotide having the base sequence set forth in SEQ ID NO: 40, or an oligonucleotide having a base sequence set forth in SEQ ID NO: 40 with a substitution, deletion, insertion, or addition of 1 to 3 nucleotides which can be used for detecting the β oxidation-related enzyme gene;

oligonucleotide (c1) is an oligonucleotide having the base sequence set forth in SEQ ID NO: 41, or an oligonucleotide having a base sequence set forth in SEQ ID NO: 41 with a substitution, deletion, insertion, or addition of 1 to 3 nucleotides which can be used for detecting the β oxidation-related enzyme gene; and oligonucleotide (d1) is an oligonucleotide having the base sequence set forth in SEQ ID NO: 42, or an oligonucleotide having a base sequence set forth in SEQ ID NO: 42 with a substitution, deletion, insertion, or addition of 1 to 3 nucleotides which can be used for detecting the β oxidation-related enzyme gene.

12. The method according to claim 11, wherein the microorganisms produce the damp-dry malodor-causing substance 4-methyl-3-hexenoic acid.

13. The method according to claim 11, wherein the gene is the Δ9desaturase gene.

14. The method according to claim 13, wherein a fragment of the Δ9desaturase gene is amplified by using at least one oligonucleotide pair selected from the group consisting of:
the oligonucleotide pair containing the oligonucleotides (c) and (d);
the oligonucleotide pair containing the oligonucleotides (e) and (f);
the oligonucleotide pair containing the oligonucleotides (g) and (h);
the oligonucleotide pair containing the oligonucleotides (i) and (j); and
the oligonucleotide pair containing the oligonucleotides (k) and (l).

15. The method according to claim 11, wherein gene is the fadB gene.

16. The method described in according to claim 15, wherein a fragment of the fadB gene is amplified by using at least one oligonucleotide pair selected from the group consisting of:
the oligonucleotide pair containing the oligonucleotides (m) and (n);
the oligonucleotide pair containing the oligonucleotides (o) and (p);
the oligonucleotide pair containing the oligonucleotides (q) and (r); and
the oligonucleotide pair containing the oligonucleotides (s) and (t).

17. The method according to claim 11, wherein the gene is the fadD gene.

18. The method according to claim 11, wherein the microorganisms are at least one microbial strain selected from the group consisting of species *Moraxella* sp. and *Moraxella osloensis*.

19. A kit for evaluating an inhibitory effect on damp-dry malodor or a kit for screening for a damp-dry malodor inhibitor, comprising:
microorganisms that produce damp-dry malodor-causing substances due to expression of the microorganisms' Δ9desaturase gene, fadB gene or fadD gene;
a sebaceous dirt component; and
an oligonucleotide selected from the group consisting of the following oligonucleotides (c) to (z) and (a1) to (d1); or an oligonucleotide pair selected from the group consisting of:
a pair of the following oligonucleotides (c) and (d),
a pair of the following oligonucleotides (e) and (f),
a pair of the following oligonucleotides (g) and (h),
a pair of the following oligonucleotides (i) and (j),
a pair of the following oligonucleotides (k) and (l),
a pair of the following oligonucleotides (m) and (n),
a pair of the following oligonucleotides (o) and (p),
a pair of the following oligonucleotides (q) and (r),
a pair of the following oligonucleotides (s) and (t),
a pair of the following oligonucleotides (u) and (v),
a pair of the following oligonucleotides (w) and (x),
a pair of the following oligonucleotides (y) and (z), a pair of the following oligonucleotides (a1) and (b1), and
a pair of the following oligonucleotides (c1) and (d1):
wherein
oligonucleotide (c) is an oligonucleotide having the base sequence set forth in SEQ ID NO: 15, or an oligonucleotide having a base sequence set forth in SEQ ID NO: 15 with a substitution, deletion, insertion, or addition of 1 to 3 nucleotides which can be used for detecting the fatty acid desaturase gene;
oligonucleotide (d) is an oligonucleotide having the base sequence set forth in SEQ ID NO: 16, or an oligonucleotide having a base sequence set forth in SEQ ID NO: 16 with a substitution, deletion, insertion, or addition of 1 to 3 nucleotides which can be used for detecting the fatty acid desaturase gene;
oligonucleotide (e) is an oligonucleotide having the base sequence set forth in SEQ ID NO: 17, or an oligonucleotide having a base sequence set forth in SEQ ID NO: 17 with a substitution, deletion, insertion, or addition of 1 to 3 nucleotides which can be used for detecting the fatty acid desaturase gene;
oligonucleotide (f) is an oligonucleotide having the base sequence set forth in SEQ ID NO: 18, or an oligonucleotide having a base sequence set forth in SEQ ID NO: 18 with a substitution, deletion, insertion, or addition of 1 to 3 nucleotides which can be used for detecting the fatty acid desaturase gene;
oligonucleotide (g) is an oligonucleotide having the base sequence set forth in SEQ ID NO: 19, or an oligonucleotide having a base sequence set forth in SEQ ID NO: 19 with a substitution, deletion, insertion, or addition of 1 to 3 nucleotides which can be used for detecting the fatty acid desaturase gene;
oligonucleotide (h) is an oligonucleotide having the base sequence set forth in SEQ ID NO: 20, or an oligonucleotide having a base sequence set forth in SEQ ID NO: 20 with a substitution, deletion, insertion, or addition of 1 to 3 nucleotides which can be used for detecting the fatty acid desaturase gene;
oligonucleotide (i) is an oligonucleotide having the base sequence set forth in SEQ ID NO: 21, or an oligonucleotide having a base sequence set forth in SEQ ID NO: 21 with a substitution, deletion, insertion, or addition of 1 to 3 nucleotides which can be used for detecting the fatty acid desaturase gene;
oligonucleotide (j) is an oligonucleotide having the base sequence set forth in SEQ ID NO: 22, or an oligonucleotide having a base sequence set forth in SEQ ID NO: 22 with a substitution, deletion, insertion, or addition of 1 to 3 nucleotides which can be used for detecting the fatty acid desaturase gene;
oligonucleotide (k) is an oligonucleotide having the base sequence set forth in SEQ ID NO: 23, or an oligonucleotide having a base sequence set forth in SEQ ID NO: 23 with a substitution, deletion, insertion, or addition of 1 to 3 nucleotides which can be used for detecting the fatty acid desaturase gene;
oligonucleotide (l) is an oligonucleotide having the base sequence set forth in SEQ ID NO: 24, or an oligonucleotide having a base sequence set forth in SEQ ID NO: 24 with a substitution, deletion, insertion, or addition of 1 to 3 nucleotides which can be used for detecting the fatty acid desaturase gene;
oligonucleotide (m) is an oligonucleotide having the base sequence set forth in SEQ ID NO: 25, or an oligonucleotide having a base sequence set forth in SEQ ID NO: 25 with a substitution, deletion, insertion, or addition of 1 to 3 nucleotides which can be used for detecting the β oxidation-related enzyme gene;
oligonucleotide (n) is an oligonucleotide having the base sequence set forth in SEQ ID NO: 26, or an oligonucleotide having a base sequence set forth in SEQ ID NO: 26 with a substitution, deletion, insertion, or addition of 1 to 3 nucleotides which can be used for detecting the β oxidation-related enzyme gene;

oligonucleotide (o) is an oligonucleotide having the base sequence set forth in SEQ ID NO: 27, or an oligonucleotide having a base sequence set forth in SEQ ID NO: 27 with a substitution, deletion, insertion, or addition of 1 to 3 nucleotides which can be used for detecting the β oxidation-related enzyme gene;

oligonucleotide (p) is an oligonucleotide having the base sequence set forth in SEQ ID NO: 28, or an oligonucleotide having a base sequence set forth in SEQ ID NO: 28 with a substitution, deletion, insertion, or addition of 1 to 3 nucleotides which can be used for detecting the β oxidation-related enzyme gene;

oligonucleotide (q) is an oligonucleotide having the base sequence set forth in SEQ ID NO: 29, or an oligonucleotide having a base sequence set forth in SEQ ID NO: 29 with a substitution, deletion, insertion, or addition of 1 to 3 nucleotides which can be used for detecting the β oxidation-related enzyme gene;

oligonucleotide (r) is an oligonucleotide having the base sequence set forth in SEQ ID NO: 30, or an oligonucleotide having a base sequence set forth in SEQ ID NO: 30 with a substitution, deletion, insertion, or addition of 1 to 3 nucleotides which can be used for detecting the β oxidation-related enzyme gene;

oligonucleotide (s) is an oligonucleotide having the base sequence set forth in SEQ ID NO: 31, or an oligonucleotide having a base sequence set forth in SEQ ID NO: 31 with a substitution, deletion, insertion, or addition of 1 to 3 nucleotides which can be used for detecting the β oxidation-related enzyme gene;

oligonucleotide (t) is an oligonucleotide having the base sequence set forth in SEQ ID NO: 32, or an oligonucleotide having a base sequence set forth in SEQ ID NO: 32 with a substitution, deletion, insertion, or addition of 1 to 3 nucleotides which can be used for detecting the β oxidation-related enzyme gene;

oligonucleotide (u) is an oligonucleotide having the base sequence set forth in SEQ ID NO: 33, or an oligonucleotide having a base sequence set forth in SEQ ID NO: 33 with a substitution, deletion, insertion, or addition of 1 to 3 nucleotides which can be used for detecting the β oxidation-related enzyme gene;

oligonucleotide (v) is an oligonucleotide having the base sequence set forth in SEQ ID NO: 34, or an oligonucleotide having a base sequence set forth in SEQ ID NO: 34 with a substitution, deletion, insertion, or addition of 1 to 3 nucleotides which can be used for detecting the β oxidation-related enzyme gene;

oligonucleotide (w) is an oligonucleotide having the base sequence set forth in SEQ ID NO: 35, or an oligonucleotide having a base sequence set forth in SEQ ID NO: 35 with a substitution, deletion, insertion, or addition of 1 to 3 nucleotides which can be used for detecting the β oxidation-related enzyme gene;

oligonucleotide (x) is an oligonucleotide having the base sequence set forth in SEQ ID NO: 36, or an oligonucleotide having a base sequence set forth in SEQ ID NO: 36 with a substitution, deletion, insertion, or addition of 1 to 3 nucleotides which can be used for detecting the β oxidation-related enzyme gene;

oligonucleotide (y) is an oligonucleotide having the base sequence set forth in SEQ ID NO: 37, or an oligonucleotide having a base sequence set forth in SEQ ID NO: 37 with a substitution, deletion, insertion, or addition of 1 to 3 nucleotides which can be used for detecting the β oxidation-related enzyme gene;

oligonucleotide (z) is an oligonucleotide having the base sequence set forth in SEQ ID NO: 38, or an oligonucleotide having a base sequence set forth in SEQ ID NO: 38 with a substitution, deletion, insertion, or addition of 1 to 3 nucleotides which can be used for detecting the β oxidation-related enzyme gene;

oligonucleotide (a1) is an oligonucleotide having the base sequence set forth in SEQ ID NO: 39, or an oligonucleotide having a base sequence set forth in SEQ ID NO: 39 with a substitution, deletion, insertion, or addition of 1 to 3 nucleotides which can be used for detecting the β oxidation-related enzyme gene;

oligonucleotide (b1) is an oligonucleotide having the base sequence set forth in SEQ ID NO: 40, or an oligonucleotide having a base sequence set forth in SEQ ID NO: 40 with a substitution, deletion, insertion, or addition of 1 to 3 nucleotides which can be used for detecting the β oxidation-related enzyme gene;

oligonucleotide (c1) is an oligonucleotide having the base sequence set forth in SEQ ID NO: 41, or an oligonucleotide having a base sequence set forth in SEQ ID NO: 41 with a substitution, deletion, insertion, or addition of 1 to 3 nucleotides which can be used for detecting the β oxidation-related enzyme gene; and oligonucleotide (d1) is an oligonucleotide having the base sequence set forth in SEQ ID NO: 42, or an oligonucleotide having a base sequence set forth in SEQ ID NO: 42 with a substitution, deletion, insertion, or addition of 1 to 3 nucleotides which can be used for detecting the β oxidation-related enzyme gene.

20. The kit according to claim 19, wherein the oligonucleotide is a nucleic acid primer.

21. The kit according to claim 20, wherein the kit comprises the oligonucleotides (c) and (d), the oligonucleotides (e) and (f), the oligonucleotides (g) and (h), the oligonucleotides (i) and (j), or the oligonucleotides (k) and (l).

22. The kit according to claim 21, wherein the gene is the Δ9desaturase gene.

23. The kit according to claim 20, wherein the kit comprises oligonucleotides (m) and (n), the oligonucleotides (o) and (p), the oligonucleotides (q) and (r), or the oligonucleotides (s) and (t).

24. The kit according to claim 23, wherein the gene is the fadB gene.

25. The kit according to claim 20, wherein the kit comprises oligonucleotides (u) and (v), the oligonucleotides (w) and (x), the oligonucleotides (y) and (z), the oligonucleotides (a1) and (b1), or the oligonucleotides (c1) and (d1).

26. The kit according to claim 25, wherein the gene is the fadD gene.

27. The method according to claim 17,
wherein a fragment of the fadD gene is amplified by using at least one oligonucleotide pair selected from the group consisting of:
the oligonucleotide pair containing the oligonucleotides (u) and (v);
the oligonucleotide pair containing the oligonucleotides (w) and (x);
the oligonucleotide pair containing the oligonucleotides (y) and (z);
the oligonucleotide pair containing the oligonucleotides (a1) and (b1); and
the oligonucleotide pair containing the oligonucleotides (c1) and (d1).

28. The method according to claim 10, wherein the microorganisms produce the damp-dry malodor-causing substance 4-methyl-3-hexenoic acid.

29. The method according to claim 10, wherein the sebaceous dirt component is an anteiso fatty acid.

30. The method according to claim 10, wherein the fatty acid desaturase gene is a Δ9desaturase gene.

31. The method according to claim 30, wherein the expression of the Δ9desaturase gene is detected by using at least one oligonucleotide pair selected from the group consisting of:
the oligonucleotide pair containing the oligonucleotides (a) and (b);
the oligonucleotide pair containing the oligonucleotides (c) and (d);
the oligonucleotide pair containing the oligonucleotides (e) and (f);
the oligonucleotide pair containing the oligonucleotides (g) and (h);
the oligonucleotide pair containing the oligonucleotides (i) and (j); and
the oligonucleotide pair containing the oligonucleotides (k) and (l).

32. The method according to claim 10, wherein the β oxidation-related enzyme gene is at least one gene selected from the group consisting of a fadB gene and a fadD gene.

33. The method according to claim 32,
wherein the expression of the fadB gene is detected by using at least one oligonucleotide pair selected from the group consisting of:
the oligonucleotide pair containing the oligonucleotides (m) and (n);
the oligonucleotide pair containing the oligonucleotides (o) and (p);
the oligonucleotide pair containing the oligonucleotides (q) and (r); and
the oligonucleotide pair containing the oligonucleotides (s) and (t).

34. The method according to claim 32,
wherein the expression of the fadD gene is detected by using at least one oligonucleotide pair selected from the group consisting of:
the oligonucleotide pair containing the oligonucleotides (u) and (v);
the oligonucleotide pair containing the oligonucleotides (w) and (x);
the oligonucleotide pair containing the oligonucleotides (y) and (z);
the oligonucleotide pair containing the oligonucleotides (a1) and (b1); and
the oligonucleotide pair containing the oligonucleotides (c1) and (d1).

35. The method according to claim 10, wherein the microorganisms are at least one microbial strain selected from the group consisting of species of *Moraxella* sp. and *Moraxella osloensis*.

* * * * *